United States Patent
Xu et al.

(10) Patent No.: US 11,725,024 B2
(45) Date of Patent: Aug. 15, 2023

(54) ANTIBODY DRUG CONJUGATES

(71) Applicant: Takeda Pharmaceutical Company Limited, Osaka (JP)

(72) Inventors: He Xu, North Andover, MA (US); Hong Myung Lee, Cambridge, MA (US); Christopher Arendt, Boston, MA (US)

(73) Assignee: Takeda Pharmaceutical Company Limited, Osaka (JP)

(*) Notice: Subject to any disclaimer, the term of this patent is extended or adjusted under 35 U.S.C. 154(b) by 0 days.

(21) Appl. No.: 17/730,924

(22) Filed: Apr. 27, 2022

(65) Prior Publication Data

US 2022/0249536 A1 Aug. 11, 2022

Related U.S. Application Data

(63) Continuation of application No. 17/522,623, filed on Nov. 9, 2021.

(60) Provisional application No. 63/250,358, filed on Sep. 30, 2021, provisional application No. 63/232,935, filed on Aug. 13, 2021, provisional application No. 63/111,478, filed on Nov. 9, 2020.

(51) Int. Cl.
| | |
|---|---|
| *C07H 21/00* | (2006.01) |
| *A61K 47/68* | (2017.01) |
| *A61K 31/7084* | (2006.01) |
| *A61P 35/00* | (2006.01) |

(52) U.S. Cl.
CPC ......... *C07H 21/00* (2013.01); *A61K 31/7084* (2013.01); *A61K 47/6849* (2017.08); *A61K 47/6889* (2017.08); *A61P 35/00* (2018.01)

(58) Field of Classification Search
None
See application file for complete search history.

(56) References Cited

U.S. PATENT DOCUMENTS

| | | | |
|---|---|---|---|
| 5,547,941 | A | 8/1996 | Battistini et al. |
| 7,053,202 | B2 | 5/2006 | O'Keeefe et al. |
| 7,473,421 | B2* | 1/2009 | La ............... C07K 14/7158 |
| | | | 435/69.6 |
| 7,569,555 | B2 | 8/2009 | Karaolis |
| 7,592,326 | B2 | 9/2009 | Karaolis |
| 7,709,458 | B2 | 5/2010 | Karaolis |
| 7,947,839 | B2 | 5/2011 | Gazzard et al. |
| 8,367,716 | B2 | 2/2013 | Karaolis |

(Continued)

FOREIGN PATENT DOCUMENTS

| | | |
|---|---|---|
| CN | 106667914 A | 5/2017 |
| EP | 1740192 B1 | 6/2012 |

(Continued)

OTHER PUBLICATIONS

U.S. Appl. No. 17/610,391, filed Nov. 2021, England et al.*

(Continued)

*Primary Examiner* — Eric Olson

(74) *Attorney, Agent, or Firm* — Sterne, Kessler, Goldstein & Fox P.L.L.C.

(57) ABSTRACT

The present disclosure provides antibody drug conjugates comprising STING modulators. Also provided are compositions comprising the antibody drug conjugates. The compounds and compositions are useful for stimulating an immune response in a subject in need thereof.

14 Claims, 9 Drawing Sheets

Specification includes a Sequence Listing.

— interchain disulfide bonds

(56) References Cited

U.S. PATENT DOCUMENTS

| | | | |
|---|---|---|---|
| 8,450,293 | B2 | 5/2013 | Jones et al. |
| 8,753,828 | B2 | 6/2014 | O'Keeefe et al. |
| 9,090,646 | B2 | 7/2015 | Jones et al. |
| 9,549,944 | B2 | 1/2017 | Dubensky et al. |
| 9,597,391 | B2 | 3/2017 | Ebenson et al. |
| 9,695,212 | B2 | 7/2017 | Dubensky et al. |
| 9,718,848 | B2 | 8/2017 | Adams et al. |
| 9,724,408 | B2 | 8/2017 | Dubensky et al. |
| 9,770,467 | B2 | 9/2017 | Dubensky et al. |
| 9,840,533 | B2 | 12/2017 | Patel et al. |
| 10,980,825 | B2 * | 4/2021 | Yoshikawa ............ C07H 21/00 |
| 11,001,605 | B2 | 5/2021 | Genieser et al. |
| 2006/0167241 | A1 | 7/2006 | Hayakawa et al. |
| 2014/0341976 | A1 | 11/2014 | Dubensky et al. |
| 2015/0056224 | A1 | 2/2015 | Dubensky et al. |
| 2017/0044206 | A1 | 2/2017 | Altman et al. |
| 2017/0146519 | A1 | 5/2017 | Defilippis et al. |
| 2017/0298139 | A1 * | 10/2017 | Thompson ......... C07K 16/2878 |
| 2018/0093964 | A1 | 4/2018 | Altman et al. |
| 2020/0071417 | A1 | 3/2020 | Loew et al. |
| 2021/0015915 | A1 * | 1/2021 | Ciavarri ................. C07F 9/094 |
| 2021/0106607 | A1 | 4/2021 | Yoshikawa et al. |
| 2021/0171565 | A1 | 6/2021 | Vyskocil et al. |
| 2021/0353760 | A1 * | 11/2021 | Lioux .................. A61K 47/643 |
| 2022/0168330 | A1 * | 6/2022 | Xu ...................... A61K 47/6851 |

FOREIGN PATENT DOCUMENTS

| | | |
|---|---|---|
| EP | 1729781 B1 | 10/2012 |
| WO | WO-01057226 A1 | 8/2001 |
| WO | WO-02088172 A2 | 11/2002 |
| WO | WO-2005089777 A1 | 9/2005 |
| WO | WO-2006045041 A2 | 4/2006 |
| WO | WO-2007054279 A2 | 5/2007 |
| WO | WO-2009133560 A1 | 11/2009 |
| WO | WO-2011003025 A1 | 1/2011 |
| WO | WO-2013185052 A1 | 12/2013 |
| WO | WO-2014093936 A1 | 6/2014 |
| WO | WO-2014099824 A1 | 6/2014 |
| WO | WO-2014109256 A1 | 7/2014 |
| WO | WO-2014179335 A1 | 11/2014 |
| WO | WO-2014179760 A1 | 11/2014 |
| WO | WO-2014189805 A1 | 11/2014 |
| WO | WO-2014189806 A1 | 11/2014 |
| WO | WO-2015017652 A1 | 2/2015 |
| WO | WO-2015074145 A1 | 5/2015 |
| WO | WO-2015077354 A1 | 5/2015 |
| WO | WO-2015185565 A1 | 12/2015 |
| WO | WO-2016096174 A1 | 6/2016 |
| WO | WO-2016096577 A1 | 6/2016 |
| WO | WO-2017123657 A1 | 7/2016 |
| WO | WO-2016120305 A1 | 8/2016 |
| WO | WO-2016145102 A1 | 9/2016 |
| WO | WO-2017011444 A1 | 1/2017 |
| WO | WO-2017011622 A1 | 1/2017 |
| WO | WO-2017019896 A1 | 2/2017 |
| WO | WO-2017027645 A1 | 2/2017 |
| WO | WO-2017027646 A1 | 2/2017 |
| WO | WO-2017075477 A1 | 5/2017 |
| WO | WO-2017093933 A1 | 6/2017 |
| WO | WO-2017100305 A2 | 6/2017 |
| WO | WO-2017106740 A1 | 6/2017 |
| WO | WO-2017123669 A1 | 7/2017 |
| WO | WO-2017161349 A1 | 9/2017 |
| WO | WO-2017165506 A1 | 9/2017 |
| WO | WO-2018172206 A1 | 9/2017 |
| WO | WO-2017175147 A1 | 10/2017 |
| WO | WO-2017175156 A1 | 10/2017 |
| WO | WO-2017186711 A1 | 11/2017 |
| WO | WO-2018009466 A1 | 1/2018 |
| WO | WO-2018009648 A1 | 1/2018 |
| WO | WO-2018009652 A1 | 1/2018 |
| WO | WO-2018013887 A1 | 1/2018 |
| WO | WO-2018013908 A1 | 1/2018 |
| WO | WO-2018198076 A1 | 1/2018 |
| WO | WO-2018198084 A1 | 1/2018 |
| WO | WO-2018045204 A1 | 3/2018 |
| WO | WO-2018060323 A1 | 4/2018 |
| WO | WO-2018065360 A1 | 4/2018 |
| WO | WO-2018098203 A1 | 5/2018 |
| WO | WO-2018100558 A2 | 6/2018 |
| WO | WO-2018118664 A1 | 6/2018 |
| WO | WO-2018118665 A1 | 6/2018 |
| WO | WO-2018119117 A1 | 6/2018 |
| WO | WO-201813 8684 A1 | 8/2018 |
| WO | WO-2018138685 A2 | 8/2018 |
| WO | WO-2018140831 A1 | 8/2018 |
| WO | WO-2018152450 A1 | 8/2018 |
| WO | WO-2018152453 A1 | 8/2018 |
| WO | WO-2018156625 A1 | 8/2018 |
| WO | WO-2018195283 A1 | 10/2018 |
| WO | WO-2018200812 A1 | 11/2018 |
| WO | WO-2019043634 A2 | 3/2019 |
| WO | WO-2019046496 A1 | 3/2019 |
| WO | WO-2019046500 A1 | 3/2019 |
| WO | WO-2019055750 A1 | 3/2019 |
| WO | WO-2020229982 A1 | 11/2020 |
| WO | WO-2021206160 A1 | 10/2021 |

OTHER PUBLICATIONS

Ito et al., "A Stable and Cleavable O-Linked Spacer for Drug Delivery Systems" Chem Pharm Bull vol. 68 pp. 212-215 (Year: 2020).*

Clivio, P., et al., "(3'-5')-Cyclic dinucleotides: synthetic strategies and biological potential," Chemical Reviews 113(10):7354-7401, American Chemical Society, United States (Oct. 2013).

Corrales, L., et al., "Direct Activation of STING in the Tumor Microenvironment Leads to Potent and Systemic Tumor Regression and Immunity," Cell Reports 11(7): 1018-1030, Cell Press, United States (May 2015).

Danilchanka, O., and Mekalanos, J. J., "Cyclic dinucleotides and the innate immune response," Cell 154(5):962-970, Elsevier, Netherlands (Aug. 2013).

Ertem, G., and Ferris, J. P., "Synthesis of RNA oligomers on heterogeneous templates," Nature 379(6562):238-40, Nature Publishing Group, United Kingdom (Jan. 1996).

Fu, J., et al., "STING agonist formulated cancer vaccines can cure established tumors resistant to PD-1 blockade," Science Translational Medicine 283(7): 1-11, American Association for the Advancement of Science, United States (Apr. 2015).

Gaffney, B. L., et al., "One-flask Syntheses of c-di-GMP and the [Rp, Sp] and [Rp, Sp] Thiophosphate Analogs," Organic Letters 12(14):3269-3271, American Chemical Society, United States (Jul. 2010).

Ishikawa, H., and Barber, G. N., "STING is an endoplasmic reticulum adaptor that facilitates innate immune signalling," Nature 455(7213):674-78, Macmillan Publishers, United Kingdom (Oct. 2008).

International Search Report and Written Opinion for International Application No. PCT/US2018/029570, European Patent Office, Netherlands, dated Aug. 17, 2018, 12 pages.

Karaolis, D. K. R., et al., "3',5'-Cyclic diguanylic acid (c-di-GMP) inhibits basal and growth factor-stimulated human colon cancer cell proliferation," Biochemical and Biophysical Research Communications 329(1):40-45, Elsevier, Netherlands (Apr. 2005).

Lioux, T. et al., "Design, Synthesis, and Biological Evaluation of Novel Cyclic Adenosine-Inosine Monophosphate (cAIMP) Analogs That Activate Stimulator of Interferon Genes (STING)," Journal of Medicinal Chemistry 59(22):10253-10267, American Chemical Society, United States (Nov. 2016).

Sawai, H., et al., "Synthesis of 2'-5' linked Oligouridylates in aqueous medium using the $Pd^{2+}$ Ion," Chem Pharm Bull 29(8):2237-2245, Pharmaceutical Society of Japan, Japan (Sep. 1981).

Sawai, H., et al., "Preparation and properties of Oligocytidylates with 2'-5' Intemucleotide linkage," Bull Chem Soc Jpn 58:361-66, The Chemical Society of Japan, Japan (Jan. 1985).

Schwede, F., et al., "The Chemistry of the Noncanonical Cyclic Dinucleotide 2'3'-cGAMP and its analogs," in the Handbook of

(56) References Cited

OTHER PUBLICATIONS

Experimental Pharmacology 238:359-384, Seifert, R., Ed., Springer International Publishing, Switzerland (2015, published online Jul. 2016).
Shanahan, C. A., et al., "Differential Analogue Binding by two classes of c-di-GMP riboswitches," J Am Chem Soc 133(39):15578-92, American Chemical Society, United States (Oct. 2011).
Shi, H., et al., "Molecular basis for the specific recognition of the metazoan cyclic GMP-AMP by the innate immune adaptor protein STING," Proc Natl Acad Sci USA 112(29)8947-52, United States National Academy of Sciences, United States (Jul. 2015).
Steinberger, O., et al., "Elevated expression of the CD4 receptor and cell cycle arrest are induced in Jurkat cells by treatment with the novel cyclic dinucleotide 3',5'-cyclic diguanylic acid," FEBS Letters 44(1):125-29, Elsevier, Netherlands (Feb. 1999).
Zhao, J., et al., "Thiophosphate analogs of c-di-GMP: Impact on polymorphism," Nucleosides Nucleotides Nucleic Acids 28(5):352-378, Taylor and Francis, United Kingdom (May 2010).
Yan, H., et al., "Synthesis and immunostimulatory properties of the phosphorothioate analogues of cdiGMP," Bioorganic & Medicinal Chem Lett 18(20):5631-34, Elsevier, Netherlands (published on line Aug. 2008, published in print Oct. 2008).
International Search Report and Written Opinion for International Application No. PCT/IB2017/057588, European Patent Office, Netherlands, dated Jun. 6, 2018, 21 pages.
Baird, J. R., et al., "Radiotherapy Combined with Novel STING-Targeting Oligonucleotides Results in Regression of Established Tumors," Cancer Res 76(1):50-61, American Association for Cancer Research, United States (2016).
Cheng, N., et al., "A nanoparticle-incorporated STING activator enhances antitumor immunity in PD-L1-insensitive models of triple-negative breast cancer," JCI insight 3(22):e120638, 20 pages, American Society for Clinical Investigation, United States (2018).
Dialer, C. R., et al., "A Click-Chemistry Linked 2'3'-cGAMP Analogue," Chemistry 25(8):2089-2095, Wiley-VCH, Germany (Feb. 2019).
Hanson, M. C., et al., "Nanoparticulate STING agonists are potent lymph node-targeted vaccine adjuvants," J Clin Invest 125(6): 2532-46, American Society for Clinical Investigation, United States (Jun. 2015).
Koshy, S. T., et al., "Liposomal Delivery Enhances Immune Activation by STING Agonists for Cancer Immunotherapy," Adv Biosyst 1(1-2):1600013, 24 pages, Wiley-Liss, United States (Feb. 2017).
Leach, D. G., et al., "STINGel: Controlled release of a cyclic dinucleotide for enhanced cancer immunotherapy," Biomaterials 163:67-75, Elsevier, Netherlands (May 2018).
Miyabe, H., et al., "A new adjuvant delivery system 'cyclic di-GMP/YSK05 liposome' for cancer immunotherapy," Journal of Controlled Release 184:20-27, Elsevier, Netherlands (Jun. 2014).
Nakamura, T., et al., "Liposomes loaded with a STING pathway ligand, cyclic di-GMP, enhance cancer immunotherapy against metastatic melanoma," Journal of Controlled Release 216:149-157, Elsevier, Netherlands (Oct. 2015).
Ramanjulu, J. M., et al., "Design of amidobenzimidazole STING receptor agonists with systemic activity," Nature 564(7736):439-443, Springer Nature Limited, Germany (Dec. 2018).

Sato, Y., et al., "A pH-sensitive cationic lipid facilitates the delivery of liposomal siRNA and gene silencing activity in vitro and in vivo," Journal of Controlled Release 163(3):267-276, Elsevier, Netherlands (Nov. 2012).
Liang, H., et al., "Host STING-dependent MDSC mobilization drives extrinsic radiation resistance," Nat Commun 8:1736, Springer Nature Limited, Netherlands (2017).
Seela, F., et al., "7-Functionalized 7-deazapurine β-d and β-1-ribonucleosides related to tubercidin and 7-deazainosine: glycosylation of pyrrolo[2,3-d]pyrimidines with 1-O-acetyl-2,3,5-tri-O-benzoyl-β-d or β-1-ribofuranose," Tetrahedron 63(39):9850-9861, Elsevier, Netherlands (Sep. 2007).
Sercombe, L., et al., "Advances and Challenges of Liposome Assisted Drug Delivery," Frontiers in Pharmacology 6:286, Frontiers Media, Switzerland (Dec. 2015).
Third Party Observation in International Application No. PCT/IB2017/057588, filed Dec. 1, 2017, Takeda Pharmaceutical Company Limited, Date of Submission: Mar. 29, 2019, 2 pages.
Wilson, D. R., et al., "Biodegradable STING agonist nanoparticles for enhanced cancer immunotherapy," Nanomedicine 14(2):237-46, Elsevier, Netherlands (Feb. 2018).
Yang, J., et al., "Preclinical characterization of GSK532, a novel STING agonist with potent anti-tumor activity," Cancer Research 78(13):Abstract 5554, Proceedings of AACR Annual Meeting, April 14-18, American Association for Cancer Research, United States (Jul. 2018).
Seela, F., et al., "7-Halogenated 7-deazapurine 2'-C-methylribonucleosides," Collect Czech Chem Commun 76(12):1413-1431, Institute of Organic Chemistry and Biochemistry, Czechia (Nov. 2011).
Miles, D. L., et al., "Interferon induction: a conformational hypothesis," Proc Natl Acad Sci USA 76(3):1018-1021, National Academy of Sciences, United States (Mar. 1979).
International Search Report and Written Opinion for International Application No. PCT/IB2020/054400, European Patent Office, Netherlands, dated Aug. 24, 2020, 17 pages.
International Search Report and Written Opinion for International Application No. PCT/IB2021/060356, European Patent Office, Netherlands, dated Mar. 14, 2022, 16 pages.
Grether, U. and Waldmann, H., "An Enzyme-Labile Safety Catch Linker for Combinatorial Synthesis on a Soluble Polymeric Support," Angew. Chem. Int. Ed. 39(9):1629-1632, Wiley-VCH Verlag GmbH, Germany (2000).
Grether, U. and Waldmann, H., "An Enzyme-Labile Safety Catch Linker for Synthesis on a Soluble Polymeric Support," Chem. Eur. J. 7(5):959-971, Wiley-VCH Verlag GmbH, Germany (2001).
Tsuchilkama, K., and An, Z., "Antibody-drug conjugates: recent advances in conjugation and linker chemistries," Protein Cell 9(1):33-46, Springer Science+Business Media, Germany (2016).
Cetinbas, N.M., et al., "Tumor Targeting of a STING Agonist with an Antibody-Drug Conjugate Elicits Potent Anti-Tumor Immune Responses," Poster #P695, Mersana Therapeutics, Cambridge, MA (2017).
Ding, A.S., et al., "Targeting Myeloid Cells in Combination Treatments for Glioma and Other Tumors," Frontiers in Immunology 10(1715):1-24, Frontiers Media SA., Switzerland (2019).
Hagerling, C., et al., "Immune effector monocyte-neutrophil cooperation induced by the primary tumor prevents metastatic progression of breast cancer," PNAS 116(43):21704-21714, National Academy of Science, United States (2019).

* cited by examiner

ANTIBODY DRUG CONJUGATES

CROSS-REFERENCE TO RELATED APPLICATIONS

This application is a continuation application of U.S. application Ser. No. 17/522,623, filed Nov. 9, 2021, which claims priority to U.S. Provisional Application No. 63/111,478, filed Nov. 9, 2020; U.S. Provisional Application No. 63/232,935, filed Aug. 13, 2021; and U.S. Provisional Application No. 63/250,358, filed Sep. 30, 2021, all of which are incorporated herein by reference in their entireties.

REFERENCE TO SEQUENCE LISTING SUBMITTED ELECTRONICALLY

The content of the electronically submitted sequence listing in ASCII text file (Name 3817_0740005_SEQ_1; Size: 14,458 bytes; and Date of Creation: Apr. 27, 2022) filed with the application is incorporated herein by reference in its entirety.

FIELD

The present disclosure provides antibody drug conjugates comprising STING modulators. Also provided are compositions comprising the antibody drug conjugates. The compounds and compositions are useful for stimulating an immune response in a subject in need thereof.

BACKGROUND

Antibody drug conjugates (ADCs), a rapidly growing class of targeted therapeutics, represent a promising new approach toward improving the selectivity and cytotoxic activity of drugs. These therapeutic agents are comprised of an antibody (or antibody fragment) that can be linked to a payload drug to form an immunoconjugate. The antibody directs the ADC to bind to the targeted cell. The ADC can then be internalized and release its payload which provides treatment for the cell. As the ADC is directed to its targeted cell, the side effects of conjugated drugs may be lower than those encountered when systematically administering the same agent.

The adaptor protein STING (Stimulator of Interferon Genes) has been shown to play a role in the innate immune system. Activation of the STING pathway triggers an immune response that results in generation of specific killer T-cells that shrink tumors and can provide long-lasting immunity so the tumors do not recur. The activated STING pathway also contributes to the antiviral response by producing antiviral and pro-inflammatory cytokines that fight the virus and mobilize both the innate and adaptive immune systems, ultimately resulting in long-lasting immunity against the pathogenic virus. The potential therapeutic benefits of enhancing both innate and adaptive immune responses make STING an attractive target for drug discovery. Cyclic dinucleotides may function as STING agonists and are being tested in clinical trials. However, their anionic properties make them poorly membrane permeable, which may limit their ability to engage STING inside the cell, often resulting in unwanted distribution of these compounds within the bloodstream.

There is still a need for new STING agonists as well as improved methods for delivering them to the targeted cell.

SUMMARY

In a first aspect, the present disclosure provides a compound of formula (I):

or a pharmaceutically acceptable salt thereof, wherein:
a is an integer from 1 to 20;
Ab is an anti-CCR2 antibody, anti-CCR2 antibody fragment, or an anti-CCR2 antigen-binding fragment;
D is a modulator of STING activity comprising an amino group on a guanine base, a guanine base derivative, an adenine base, or an adenine base derivative; and
L is a linker that, is covalently bonded to Ab; and is also covalently bonded to said amino group on D.

In a first embodiment of the first aspect, the present disclosure provides a compound of formula (I), or a pharmaceutically acceptable salt thereof, wherein D-L is represented by the formula (Ia):

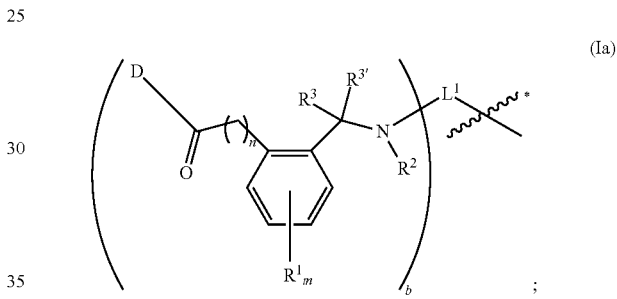

wherein:
⁓ denotes the point of attachment to Ab;
b is an integer from 1 to 20;
m is 0, 1, 2, 3, or 4;
n is 0 or 1;
each $R^1$ is independently selected from $C_1$-$C_4$alkyl, O—$C_1$-$C_4$alkyl, and halogen;
$R^2$ is selected from $C_1$-$C_4$alkyl and —$(CH_2CH_2O)_s$—$CH_3$; wherein s is an integer from 1 to 10;
$R^3$ and $R^{3'}$ are each independently selected from hydrogen and $C_1$-$C_3$alkyl; and
$L^1$ is a cleavable linker fragment.

In a second embodiment of the first aspect, the present disclosure provides a compound of formula (I), or a pharmaceutically acceptable salt thereof, wherein D-L is represented by the formula (Ia), wherein:
a is an integer from 1 to 8;
b is an integer from 1 to 10; and
m is 0.

In a third embodiment of the first aspect, the present disclosure provides a compound of formula (I), or a pharmaceutically acceptable salt thereof, wherein D-L is represented by the formula (Ia), wherein:
m is 0;
n is 0; and
$R^3$ and $R^{3'}$ are each hydrogen.

In a third embodiment of the first aspect, the present disclosure provides a compound of formula (I), or a pharmaceutically acceptable salt thereof, wherein D-L is represented by the formula (Ia), wherein $L^1$ is

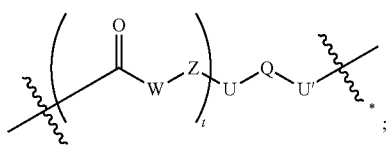

wherein:

⸸ is the point of attachment to the nitrogen atom of formula (Ia);

⁎ is the point of attachment to Ab;

t is an integer from 1 and 10;

W is absent or a self-immolative group;

Z is absent or a peptide of 2 to 5 amino acids;

U and U' are independently absent or a spacer; and

Q is a heterobifunctional group;

provided that W and Z are not both absent.

In a fourth embodiment of the first aspect, W is a self-immolative group selected from

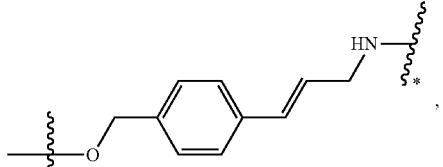

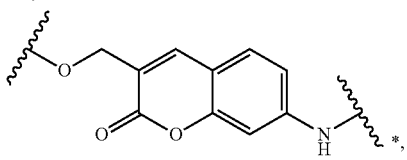

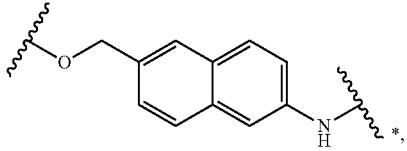

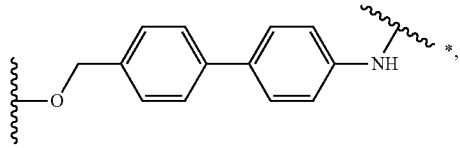

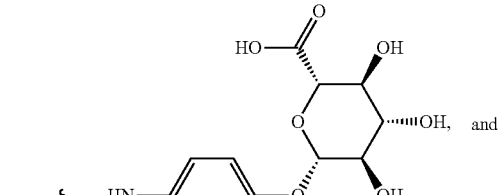

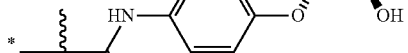

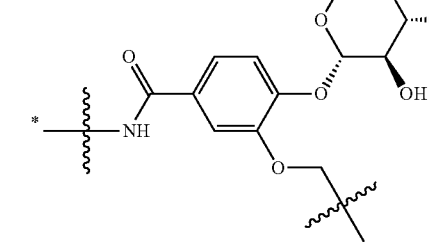

wherein:

⸸ is the point of attachment to the carbonyl group; and

⁎ is the point of attachment to Z.

In a fifth embodiment of the first aspect, W is

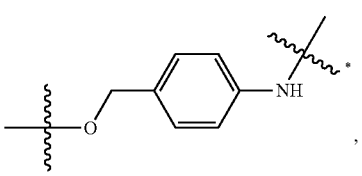

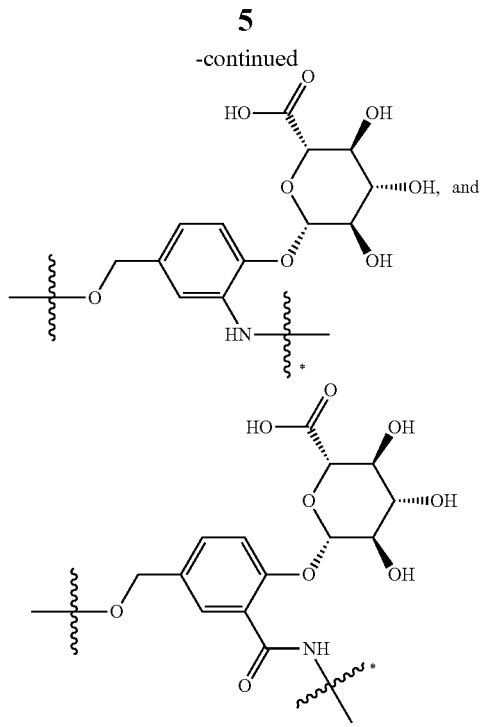

In a sixth embodiment of the first aspect, W is

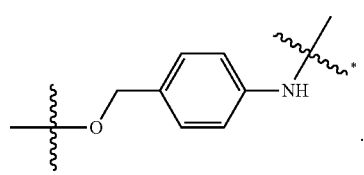 [SMILES: *Nc1ccc(CO*)cc1]

In a seventh embodiment of the first aspect, Z is a peptide capable of being enzymatically cleaved.

In an eighth embodiment of the first aspect, Z is cathepsin cleavable.

In a ninth embodiment of the first aspect, Z is a two-amino acid peptide selected from Val-Cit, Cit-Val, Val-Ala, Ala-Val, Phe-Lys, and Lys-Phe.

In a tenth embodiment of the first aspect, Z is Ala-Val or Val-Ala.

In an eleventh embodiment of the first aspect, U' is absent and U is selected from

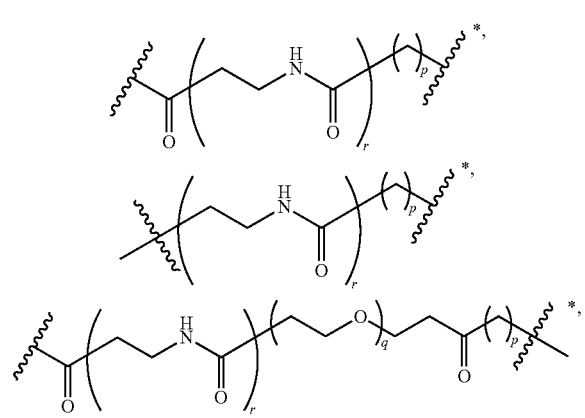

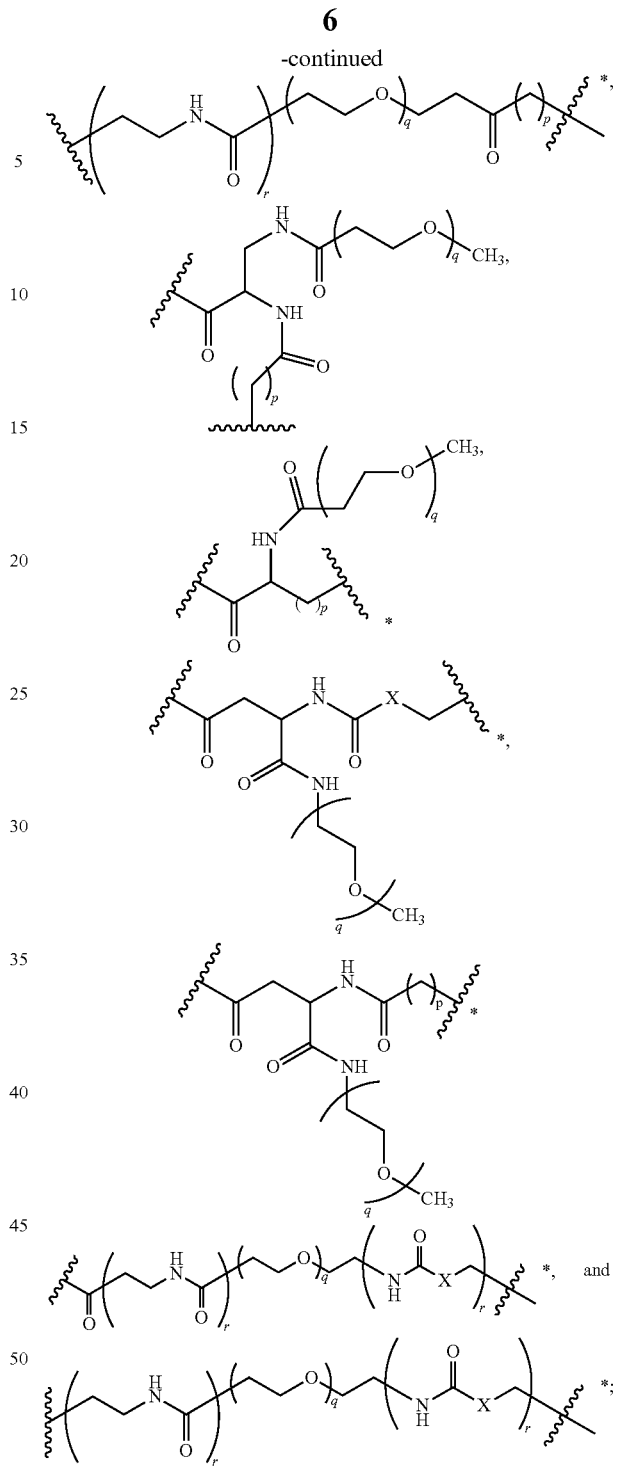

wherein:

⸾ is the point of attachment to Z;

⸾ the point of attachment to Q;

p is an integer from 1 to 6;

q is an integer from 1 to 20;

X is O or —$CH_2$—; and each r is independently 0 or 1.

In a twelfth embodiment of the first aspect, U' is absent and U is:

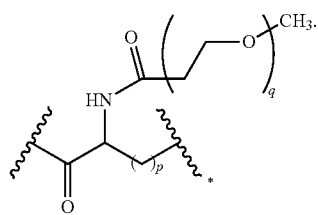

In a thirteenth embodiment of the first aspect, Q is a heterobifunctional group which is attached to U' or, when U' is absent, is attached to Ab through chemical or enzyme-mediated conjugation.

In a fourteenth embodiment of the first aspect, Q is selected from

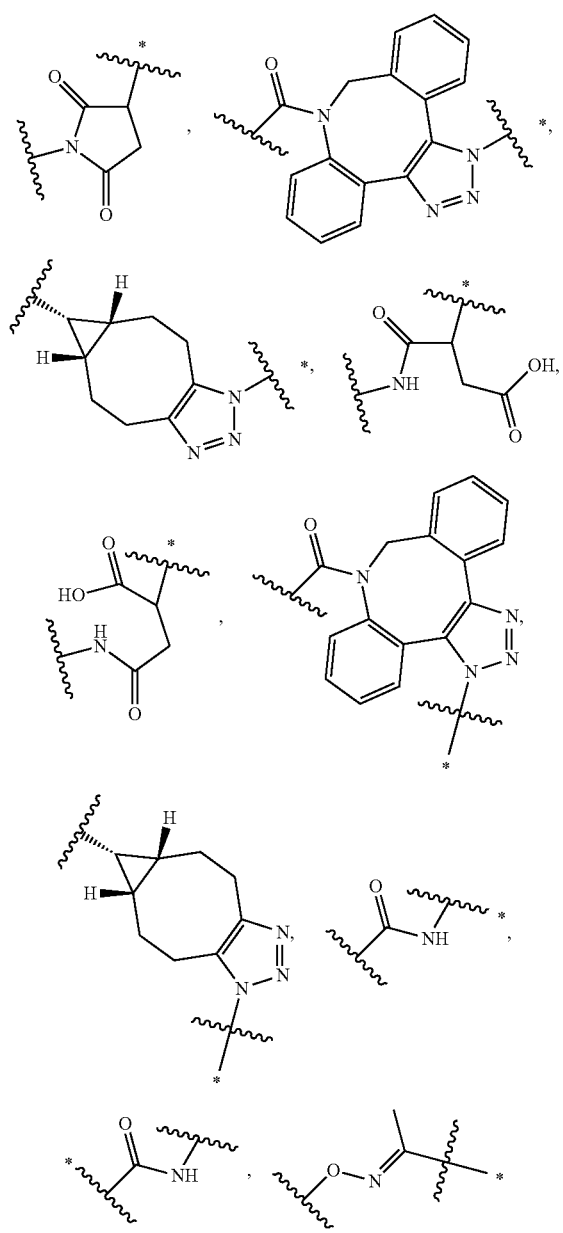

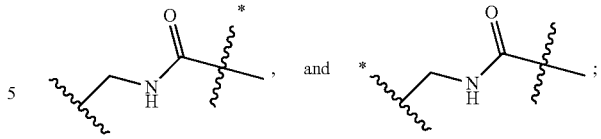

wherein

⸲ is the point of attachment to U or, when U is absent, the point of attachment to Z; and ⸲ is the point of attachment to U', or, when U' is absent, the point of attachment to Ab.

In a fifteenth embodiment of the first aspect, Q is:

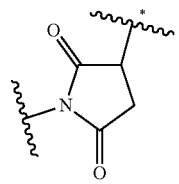

In a sixteenth embodiment of the first aspect, t is 1.

In a seventeenth embodiment of the first aspect, $R^2$ is —$CH_3$, and $R^3$ and $R^{3'}$ are each hydrogen.

In an eighteenth embodiment of the first aspect, a is from 2 to 6.

In a nineteenth embodiment of the first aspect, b is 1.

In a twentieth embodiment of the first aspect, the amino-substituted compound that modulates STING activity is a compound of formula (II):

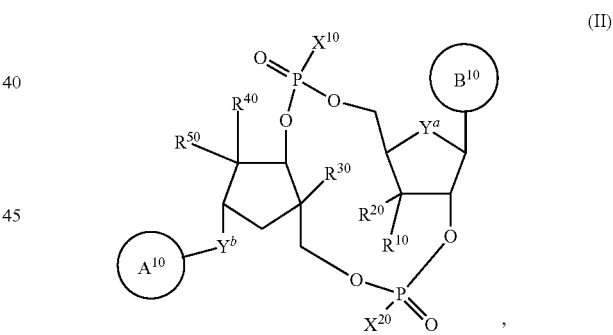

wherein:
$X^{10}$ is SH or OH;
$X^{20}$ is SH or OH;
$Y^a$ is O, S, or $CH_2$;
$Y^b$ is O, S, NH, or $NR^a$, wherein $R^a$ is $C_1$-$C_4$alkyl;
$R^{10}$ is hydrogen, fluoro, OH, $NH_2$, $OR^b$, or $NHR^b$;
$R^{20}$ is hydrogen or fluoro;
$R^{30}$ is hydrogen; $R^{40}$ is hydrogen, fluoro, OH, $NH_2$, $OR^b$, or $NHR^b$; or $R^{30}$ and $R^{40}$ are taken together to form $CH_2O$;
$R^{50}$ is hydrogen or fluoro;
$R^b$ is $C_1$-$C_6$alkyl, halo($C_1$-$C_6$)alkyl, or $C_3$-$C_6$cycloalkyl;
Ring $A^{10}$ is an optionally substituted 5- or 6-membered monocyclic heteroaryl ring containing 1-4 heteroatoms selected from N, O, or S, or an optionally substituted 9 or 10 membered bicyclic heteroaryl ring containing 1-5 heteroatoms selected from N, O, or S; wherein ring $A^{10}$ comprises at least one N atom in the ring, and wherein $Y^b$ is attached to a carbon atom of ring $A^{10}$; and Ring $B^{10}$ is an optionally substituted 9 or 10-membered bicyclic heteroaryl ring containing from 2 to 5 heteroatoms selected from N, O, or S; wherein ring $B^{10}$ comprises at least two N atoms in the ring;

provided that either ring $A^{10}$ or ring $B^{10}$ is attached to 'L' in formula (I) through the amino group.

In a twenty-first embodiment of the first aspect, the amino-substituted compound that modulates STING activity is

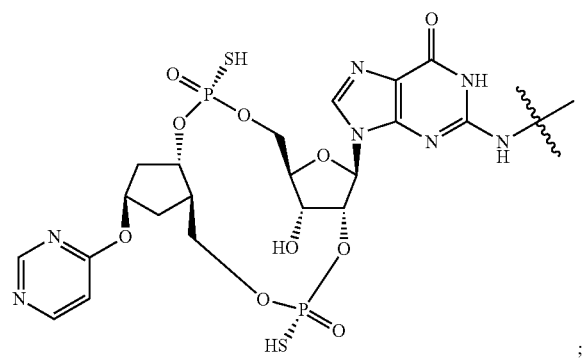 [SMILES: *Nc1nc2c(ncn2[C@@H]2O[C@@H]3CO[P@@](=O)(S)O[C@H]4C[C@H](Oc5ccncn5)C[C@@H]4CO[P@@](=O)(S)O[C@@H]2[C@@H]3O)c(=O)[nH]1]

wherein ⸺ is the point of attachment to 'L' in formula (I).

In a twenty-second embodiment of the first aspect, the amino-substituted compound that modulates STING activity is a compound of formula (III):

(III)

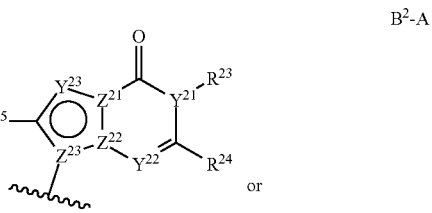

or a pharmaceutically acceptable salt thereof; wherein
$X^{10}$ is SH or OH;
$X^{20}$ is SH or OH;
$Y^c$ is O, S, or $CH_2$;
$Y^d$ is O, S, or $CH_2$;
$B^{100}$ is a group represented by formula ($B^1$-A) or formula ($B^1$-B):

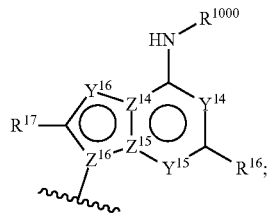

$B^1$-A

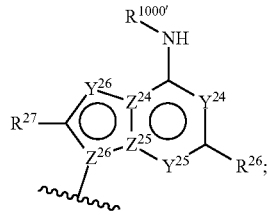

$B^1$-B $R^{13}$, $R^{14}$, $R^{15}$, $R^{16}$ and $R^{17}$ are each independently a hydrogen atom or a substituent;

$R^{1000}$ is hydrogen or a bond to the carbonyl group of formula (I);

$Y^{11}$, $Y^{12}$, $Y^{13}$, $Y^{14}$, $Y^{15}$ and $Y^{16}$ are each independently N or $CR^{1a}$, wherein $R^{1a}$ is hydrogen or a substituent;

$Z^{11}$, $Z^{12}$, $Z^{13}$, $Z^{14}$, $Z^{15}$ and $Z^{16}$ are each independently N or C;

$R^{105}$ is a hydrogen atom or a substituent;

$B^{200}$ is a group represented by formula ($B^2$-A) or formula ($B^2$-B):

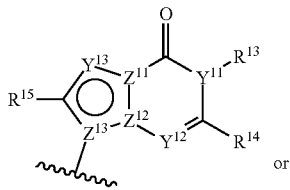

$B^2$-A or $B^2$-B $R^{23}$, $R^{24}$, $R^{25}$, $R^{26}$ and $R^{27}$ are each independently a hydrogen atom or a substituent;

$R^{100'}$ is hydrogen or a bond to the carbonyl group of formula (I);

$Y^{21}$, $Y^{22}$, $Y^{23}$, $Y^{24}$, $Y^{25}$ and $Y^{26}$ are each independently N or $CR^{2a}$, wherein $R^{2a}$ is hydrogen or a substituent;

$Z^{21}$, $Z^{22}$, $Z^{23}$, $Z^{24}$, $Z^{25}$ and $Z^{26}$ are each independently N or C; and $R^{205}$ is a hydrogen atom or a substituent; wherein $R^{105}$ and $R^{205}$ are each independently attached to 2- or 3-position of the 5-membered ring they are attached to respectively;

provided that:
one of $B^{100}$ or $B^{200}$ is attached to 'L' in formula (I) through the amino group.

In a twenty-third embodiment of the first aspect, the amino-substituted compound that modulates STING activity is a compound of formula (IIIa):

(IIIa)

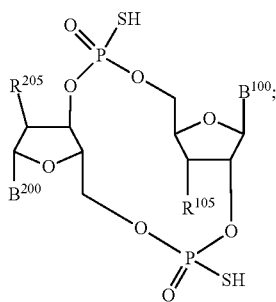

or a pharmaceutically acceptable salt thereof; wherein $B^{100}$ is a group represented by formula ($B^1$-A) or formula ($B^1$-B):

$B^1$-A

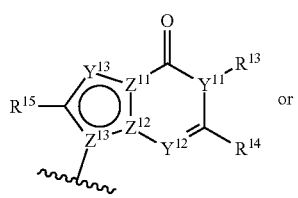

or $B^1$-B

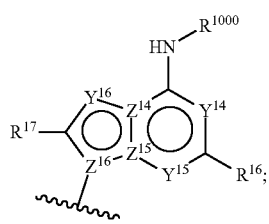

$R^{13}$, $R^{14}$, $R^{15}$, $R^{16}$ and $R^{17}$ are each independently a hydrogen atom or a substituent;

$R^{1000}$ is hydrogen or a bond to the carbonyl group of formula (I);

$Y^{11}$, $Y^{12}$, $Y^{13}$, $Y^{14}$, $Y^{15}$ and $Y^{16}$ are each independently N or $CR^{1a}$, wherein $R^{1a}$ is hydrogen or a substituent;

$Z^{11}$, $Z^{12}$, $Z^{13}$, $Z^{14}$, $Z^{15}$ and $Z^{16}$ are each independently N or C;

$R^{105}$ is a hydrogen atom or a substituent;

$B^{200}$ is a group represented by formula ($B^2$-A) or formula ($B^2$-B):

$B^2$-A

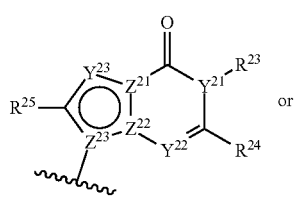

or $B^2$-B

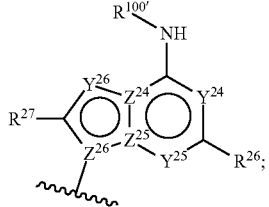

$R^{23}$, $R^{24}$, $R^{25}$, $R^{26}$ and $R^{27}$ are each independently a hydrogen atom or a substituent;

$R^{100'}$ is hydrogen or a bond to the carbonyl group of formula (I);

$Y^{21}$, $Y^{22}$, $Y^{23}$, $Y^{24}$, $Y^{25}$ and $Y^{26}$ are each independently N or $CR^{2a}$, wherein $R^{2a}$ is hydrogen or a substituent;

$Z^{21}$, $Z^{22}$, $Z^{23}$, $Z^{24}$, $Z^{25}$ and $Z^{26}$ are each independently N or C; and $R^{205}$ is a hydrogen atom or a substituent; wherein $R^{105}$ and $R^{205}$ are each independently attached to 2- or 3-position of the 5-membered ring they are attached to respectively;

provided that:

one of $B^{100}$ or $B^{200}$ is:

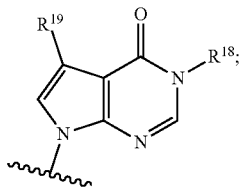

wherein:

$R^{18}$ is hydrogen or $C_{1-6}$ alkyl; and $R^{19}$ is a halogen atom;

and the other is attached to the 'L' group in formula (I) through an —NH— group.

In a twenty-fourth embodiment of the first aspect, the amino-substituted compound that modulates STING activity is a compound of formula of formula (IV):

(IV)

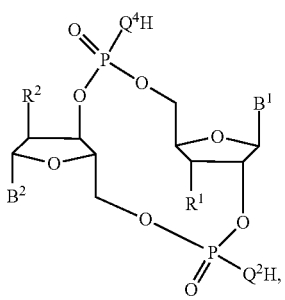

or a pharmaceutically acceptable salt thereof, wherein:

$R^1$ and $R^2$ are each independently a hydroxy group or a halogen atom;

$B^1$ is:

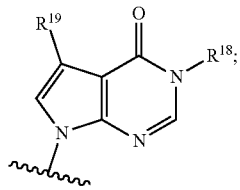

$R^{18}$ is hydrogen or $C_{1-6}$ alkyl;
$R^{19}$ is a halogen atom;
$B^2$ is:

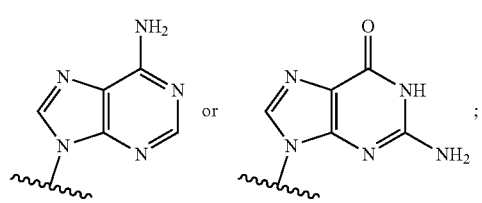 [SMILES: *n1cnc2c(N)ncnc21 ; *n1cnc2c(=O)[nH]c(N)nc21]

and
$Q^2$ and $Q^4$ are each independently an oxygen atom or a sulfur atom.

In a twenty-fifth embodiment of the first aspect, the amino-substituted compound that modulates STING activity is:

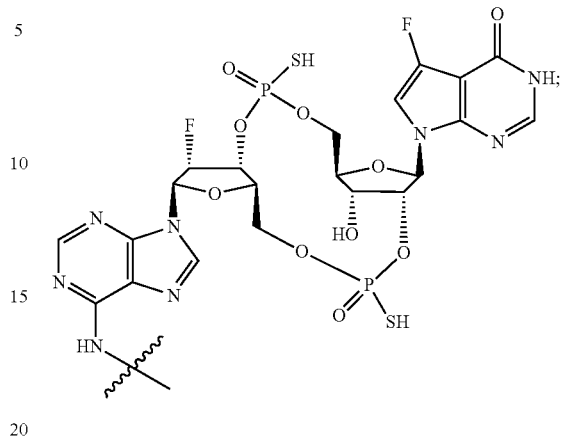

or a pharmaceutically acceptable salt thereof, wherein ⸾ is the point of attachment to L.

In a twenty-sixth embodiment of the first aspect, the present disclosure provides a compound of formula (I), or a pharmaceutically acceptable salt thereof, having the structure of formula (VI):

(VI)

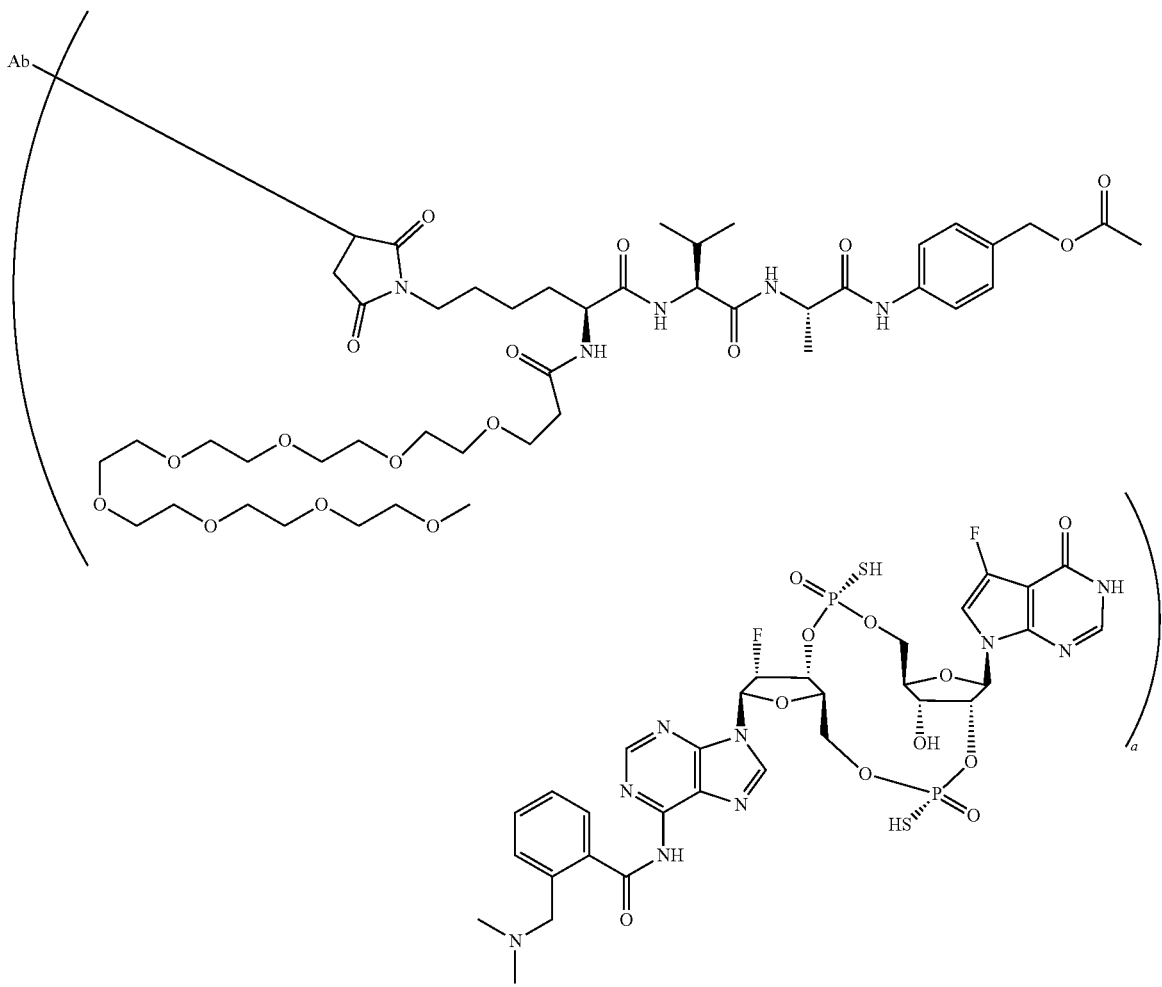

wherein a is an integer from 1 to 6.

In a twenty-seventh embodiment of the first aspect, Ab is an antibody or fragment thereof that binds human CCR2 or a portion thereof, and is capable of blocking binding of a chemokine to CCR2 and inhibiting a function of CCR2.

In a twenty-eighth embodiment of the first aspect, the antibody is selected from the group consisting of monoclonal antibody 1D9 or an antibody which can compete with 1D9 for binding to human CCR2 or a portion of CCR2; MC-21; STI-B020X; UniTI-101; and 4.40A68G.

In a twenty-ninth embodiment of the first aspect, the antibody is monoclonal antibody 1D9 or an antibody which can compete with 1D9 for binding to human CCR2 or a portion of CCR2.

In a thirtieth embodiment of the first aspect, the antibody is a chimeric antibody, a humanized antibody, a human antibody, a mouse antibody, a rat antibody, a goat antibody, or a rabbit antibody.

In a thirty-first embodiment of the first aspect, the anti-CCR2 antibody, anti-CCR2 antibody fragment, or anti-CCR2 antigen-binding fragment comprises a light chain CDR1 comprising amino acids 24-39 of SEQ ID NO: 1; a light chain CDR2 comprising amino acids 55-61 of SEQ ID NO: 1; a light chain CDR3 comprising amino acids 94-102 of SEQ ID NO: 1; a heavy chain CDR1 comprising amino acids 31-35 of SEQ ID NO:2; a heavy chain CDR2 comprising amino acids 50-68 of SEQ ID NO:2; and a heavy chain CDR3 comprising amino acids 101-106 of SEQ ID NO:2.

In a thirty-second embodiment of the first aspect, the anti-CCR2 antibody, anti-CCR2 antibody fragment, or anti-CCR2 antigen-binding fragment comprises a heavy chain variable region comprising the amino acid sequence of SEQ ID NO: 2.

In a thirty-third embodiment of the first aspect, the antibody, the anti-CCR2 antibody, anti-CCR2 antibody fragment, or anti-CCR2 antigen-binding fragment comprises a light chain variable region comprising the amino acid sequence of SEQ ID NO: 1.

In a thirty-fourth embodiment of the first aspect, the anti-CCR2 antibody, anti-CCR2 antibody fragment, or anti-CCR2 antigen-binding fragment comprises a heavy chain variable region and a light chain variable region, wherein the heavy chain variable region comprises the amino acid sequence of SEQ ID NO: 2.

In a thirty-fifth embodiment of the first aspect, the anti-CCR2 antibody, anti-CCR2 antibody fragment, or anti-CCR2 antigen-binding fragment comprises a heavy chain variable region and a light chain variable region, wherein the light chain variable region comprises the amino acid sequence of SEQ ID NO: 1.

In a thirty-sixth embodiment of the first aspect, the anti-CCR2 antibody, anti-CCR2 antibody fragment, or anti-CCR2 antigen-binding fragment comprises a heavy chain variable region comprising the amino acid sequence of SEQ ID NO: 2 and a light chain variable region, wherein the light chain variable region comprises the amino acid sequence of SEQ ID NO: 1.

In a thirty-seventh embodiment of the first aspect, the anti-CCR2 antibody, anti-CCR2 antibody fragment, or anti-CCR2 antigen-binding fragment further comprises a heavy chain constant region selected from human immunoglobulins IgG$_1$, IgG$_2$, IgG$_3$, IgG$_4$, IgA$_1$, and IgA$_2$ heavy chain constant regions.

In a thirty-eighth embodiment of the first aspect, the anti-CCR2 antibody, anti-CCR2 antibody fragment, or anti-CCR2 antigen-binding fragment further comprises a light chain constant region selected from the group consisting of human immunoglobulins IgGκ and IgGλ light chain constant regions.

In a thirty-ninth embodiment of the first aspect, the anti-CCR2 antibody, anti-CCR2 antibody fragment, or anti-CCR2 antigen-binding fragment binds to the same epitope as an antibody comprising a variable heavy chain region of SEQ ID NO: 2 and a variable light chain region of SEQ ID NO: 1.

In a fortieth embodiment of the first aspect, the anti-CCR2 antibody comprises a heavy chain region of SEQ ID NO: 3.

In a forty-first embodiment of the first aspect, the anti-CCR2 antibody comprises a light chain region of SEQ ID NO: 4.

In a forty-second embodiment of the first aspect, the anti-CCR2 antibody comprises a heavy chain region of SEQ ID NO: 3 and a light chain region of SEQ ID NO: 4.

In a second aspect, the present disclosure provides a pharmaceutical composition comprising a compound of formula (I), or a pharmaceutically acceptable salt thereof, and one or more pharmaceutically acceptable carriers.

In a first embodiment of the second aspect, the pharmaceutical composition comprises a compound of formula (I) and an antibody that binds Programmed Death 1 (PD-1, CD279, hSLE1 or SLEB2).

In a second embodiment of the second aspect, the pharmaceutical composition comprises a compound of formula (I) and an antibody that binds Programmed Death Ligand 1 (PD-L1, CD274, or B7H1).

In a third aspect, the present disclosure provides a method of treating cancer in a subject in need thereof, the method comprising administering to the subject a pharmaceutically acceptable amount of a compound of formula (I), or a pharmaceutically acceptable salt thereof.

In a first embodiment of the third aspect, the method of treating cancer comprises administering to the subject a pharmaceutically acceptable amount of a compound of formula (I), or a pharmaceutically acceptable salt thereof, and an anti-PD-1 antibody.

In a second embodiment of the third aspect, the method of treating cancer comprises administering to the subject a pharmaceutically acceptable amount of a compound of formula (I), or a pharmaceutically acceptable salt thereof, and an anti-PD-L1 antibody.

In a third embodiment of the third aspect, the compound of formula (I), or a pharmaceutically acceptable salt thereof, and the anti-PD-1 antibody are administered simultaneously.

In a fourth embodiment of the third aspect, the compound of formula (I), or a pharmaceutically acceptable salt thereof, and the anti-PD-1 antibody are administered sequentially.

In a fifth embodiment of the third aspect, the compound of formula (I), or a pharmaceutically acceptable salt thereof, and the anti-PD-L1 antibody are administered simultaneously.

In a sixth embodiment of the third aspect, the compound of formula (I), or a pharmaceutically acceptable salt thereof, and the anti-PD-L1 antibody are administered sequentially.

In a seventh embodiment of the third aspect, the method further comprises administering radiation to the subject. In an eighth embodiment of the third aspect, the radiation is particle radiation. In a ninth embodiment of the third aspect, the radiation is administered by external beam radiation.

In a fourth aspect, the present disclosure provides a method for stimulating an immune response in a subject in need thereof, the method comprising administering to the subject a pharmaceutically acceptable amount of a compound of formula (I), or a pharmaceutically acceptable salt thereof.

DETAILED DESCRIPTION

Figure 1:
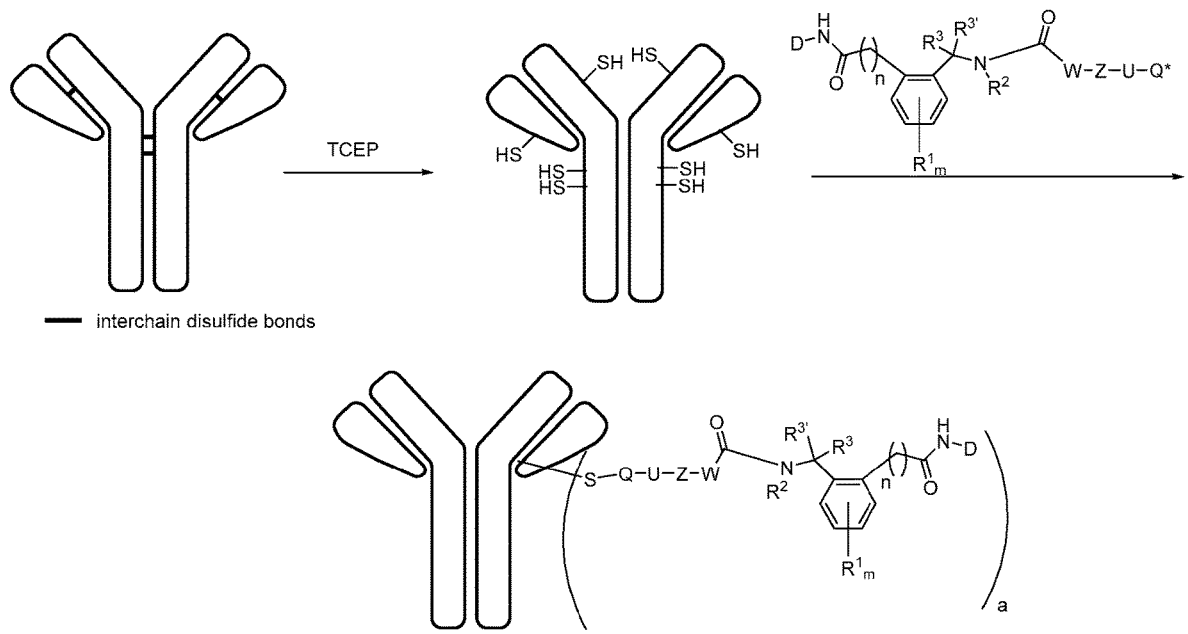
FIG. 1 depicts the preparation of Ab-STING agonist conjugates via stochastic cysteine conjugation.

Unless defined otherwise, all technical and scientific terms used herein have the same meaning as is commonly understood by one of skill in the art to which this disclosure belongs. All patents and publications referred to herein are incorporated by reference in their entireties.

The singular forms "a," "an," and "the" include plural referents unless the context dictates otherwise.

As used herein, the term "or" is a logical disjunction (i.e., and/or) and does not indicate an exclusive disjunction unless expressly indicated such as with the terms "either," "unless," "alternatively," and words of similar effect.

As used herein, the term "about" refers to ±10%.

Antibody Drug Conjugates

In some embodiments, the present disclosure provides a compound of formula (I),

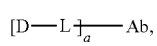
(I)

or a pharmaceutically acceptable salt thereof, wherein:
a is an integer from 1 to 20;
Ab is an anti-CCR2 antibody, anti-CCR2 antibody fragment, or an anti-CCR2 antigen-binding fragment;

D is a modulator of STING activity comprising an amino group on a guanine base, a guanine base derivative, an adenine base, or an adenine base derivative; and L is a linker that, is covalently bonded to Ab; and is also covalently bonded to said amino group on D.

STING Modulator Moiety

The present disclosure provides compounds comprising modulators of STING activity. In certain embodiments, the STING modulator is a compound that targets the STING pathway as an antagonist or an agonist. In some embodiments, the STING modulator is an agonist. In certain embodiments, the STING modulator comprises an amino group on a guanine base, a guanine base derivative, an adenine base, or an adenine base derivative. In some embodiments, the STING modulator is a cyclic dinucleotide, or a cyclic dinucleotide-like compound (each, a CDN).

In some embodiments, the STING modulator is a compound of formula (II):

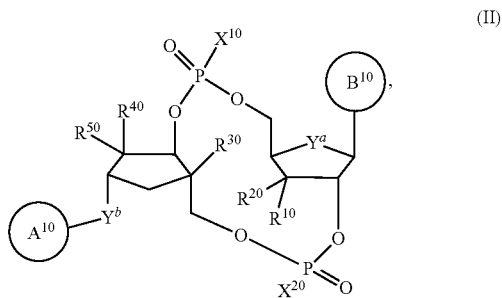
(II)

or a pharmaceutically acceptable salt thereof, wherein:
$X^{10}$ is —SH or —OH;
$X^{20}$ is —SH or —OH;
$Y^a$ is —O—, —S—, or —CH$_2$—;
$Y^b$ is —O—, —S—, —NH—, or —NR$^a$—, wherein R$^a$ is C$_1$-C$_4$alkyl;
$R^{10}$ is hydrogen, fluoro, —OH, —NH$_2$, —OR$^b$, or —NHR$^b$;
$R^{20}$ is hydrogen or fluoro;
$R^{30}$ is hydrogen; $R^{40}$ is hydrogen, fluoro, —OH, —NH$_2$, —OR$^b$, or —NHR$^b$; or $R^{30}$ and $R^{40}$ are taken together to form —CH$_2$O—;
$R^{50}$ is hydrogen or fluoro;
$R^b$ is C$_1$-C$_6$alkyl, halo(C$_1$-C$_6$)alkyl, or C$_3$-C$_6$cycloalkyl;
Ring $A^{10}$ is an optionally substituted 5- or 6-membered monocyclic heteroaryl ring containing 1-4 heteroatoms selected from N, O, or S, or an optionally substituted 9- or 10-membered bicyclic heteroaryl ring containing 1-5 heteroatoms selected from N, O, or S; wherein ring $A^{10}$ comprises at least one N atom in the ring, and wherein $Y^b$ is attached to a carbon atom of ring $A^{10}$; and Ring $B^{10}$ is an optionally substituted 9- or 10-membered bicyclic heteroaryl ring containing 2-5 heteroatoms selected from N, O, or S; wherein ring $B^{10}$ comprises at least two N atoms in the ring;

provided that either ring $A^{10}$ or ring $B^{10}$ is attached to 'L' in formula (I) through an —NH— group.

As described herein, ring $A^{10}$ and ring $B^{10}$ can contain one or more substituents and thus can be optionally substituted. Suitable substituents on the unsaturated carbon atom of a heteroaryl group include, and are generally selected from, -halo, —$NO_2$, —CN, —$R^+$, —$C(R^+)$=$C(R^+)_2$, —C≡C—$R^+$, —$OR^+$, —$SR^\circ$, —$S(O)R^\circ$, —$SO_2R^\circ$, —$SO_3R^+$, —$SO_2N(R^+)_2$, —$N(R^+)_2$, —$NR^+C(O)R^+$, —$NR^+C(S)R^+$, —$NR^+C(O)N(R^+)_2$, —$NR^+C(S)N(R^+)_2$, —$N(R^+)C(=NR^+)$—$N(R^+)_2$, —$N(R^+)C(=NR^+)$—$R^\circ$, —$NR^+CO_2R^+$, —$NR^+SO_2R^\circ$, —$NR^+SO_2N(R^+)_2$, —O—$C(O)R^+$, —O—$CO_2R^+$, —$OC(O)N(R^+)_2$, —$C(O)R^+$, —$C(S)R^\circ$, —$CO_2R^+$, —$C(O)$—$C(O)R^+$, —$C(O)N(R^+)_2$, —$C(S)N(R^+)_2$, —$C(O)N(R^+)$—$OR^+$, —$C(O)N(R^+)C(=NR^+)$—$N(R^+)_2$, —$N(R^+)C(=NR^+)$—$N(R^+)$—$C(O)R^+$, —$C(=NR^+)$—$N(R^+)_2$, —$C(=NR^+)$—$OR^+$, —$N(R^+)$—$N(R^+)_2$, —$C(=NR^+)$—$N(R^+)$—$OR^+$, —$C(R^\circ)$=N—$OR^+$, —$P(O)(R^+)_2$, —$P(O)(OR^+)_2$, —O—P(O)—$OR^+$, and —$P(O)(NR^+)$—$N(R^+)_2$, wherein $R^+$, independently, is hydrogen or an optionally substituted aliphatic, aryl, heteroaryl, cycloaliphatic, or heterocyclyl group, or two independent occurrences of $R^+$ are taken together with their intervening atom(s) to form an optionally substituted 5-7-membered aryl, heteroaryl, cycloaliphatic, or heterocyclyl. In some embodiments, $R^+$, independently, is hydrogen, $C_{1-6}$ aliphatic, or $C_{3-6}$ cycloaliphatic. Each $R^\circ$ is, independently, an optionally substituted aliphatic, aryl, heteroaryl, cycloaliphatic, or heterocyclyl group.

As detailed above, in some embodiments, two independent occurrences of $R^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In some embodiments the STING modulator is a compound of formula (IIA):

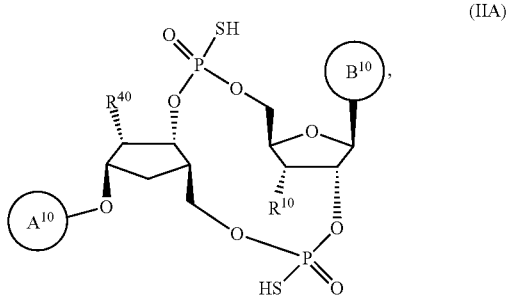

(IIA)

or a pharmaceutically acceptable salt thereof, wherein $R^{10}$ and $R^{40}$ are each independently hydrogen, fluoro, —OH, or —$OCH_2CF_3$ and rings $A^{10}$ and $B^{10}$ are as defined for the compound of formula (II), provided that either ring $A^{10}$ or ring $B^{10}$ is attached to 'L' through an —NH— group.

In some embodiments, ring $A^{10}$ is an optionally substituted 6-membered monocyclic heteroaryl ring containing 1, 2, or 3 nitrogen atoms.

In some embodiments, ring $B^{10}$ is:

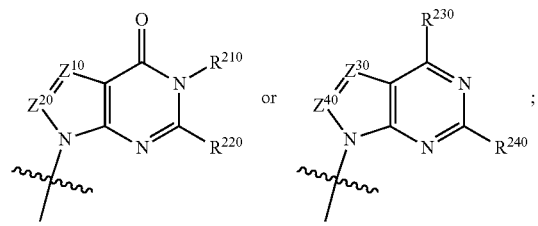

wherein:
$Z^{10}$, $Z^{20}$, $Z^{30}$, and $Z^{40}$ are each independently N or $CR^{200}$;
$R^{210}$ is hydrogen or $C_1$-$C_6$alkyl, halo($C_1$-$C_6$)alkyl, or $C_3$-$C_6$cycloalkyl;
$R^{230}$ is hydrogen or —$NH_2$; and
$R^{200}$, $R^{220}$, and $R^{240}$ are each independently hydrogen, halogen, —OH, —$NH_2$, —CN, $C_1$-$C_6$alkyl, halo($C_1$-$C_6$)alkyl, or $C_3$-$C_6$cycloalkyl.

In some embodiments the STING modulator is:

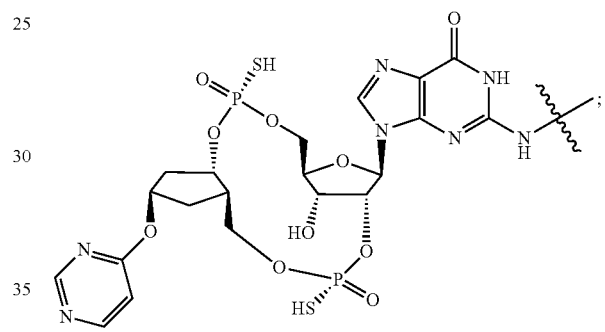

or a pharmaceutically acceptable salt thereof, wherein ⸹ is the point of attachment to the 'L' group of the parent molecular moiety.

In some embodiments, the STING modulator is a compound of formula (III):

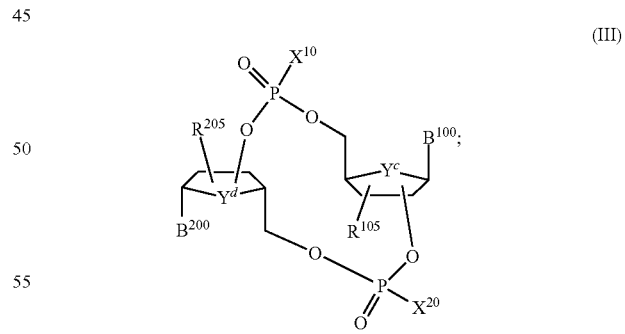

(III)

or a pharmaceutically acceptable salt thereof, wherein:
$X^{10}$ is SH or OH;
$X^{20}$ is SH or OH;
$Y^c$ is O, S, or $CH_2$;
$Y^d$ is 0, S, or $CH_2$;
$R^{105}$ and $R^{205}$ are each independently hydrogen or a substituent, wherein $R^{105}$ and $R^{205}$ are each independently attached to 2- or 3-position of the 5-membered ring they are attached to respectively;

$B^{100}$ is a group represented by formula ($B^1$-A) or formula ($B^1$-B):

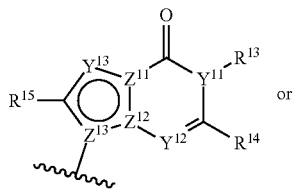

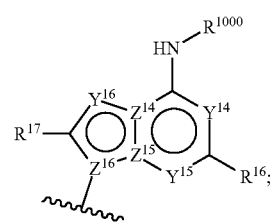

$R^{13}$, $R^{14}$, $R^{15}$, $R^{16}$ and $R^{17}$ are each independently a hydrogen atom or a substituent;
$R^{1000}$ is hydrogen or a bond to the carbonyl group of formula (I);
$Y^{11}, Y^{12}, Y^{13}, Y^{14}, Y^{15}$ and $Y^{16}$ are each independently N or $CR^{1a}$;
$Z^{11}, Z^{12}, Z^{13}, Z^{14}, Z^{15}$ and $Z^{16}$ are each independently N or C;
$R^{1a}$ is a hydrogen atom or a substituent;
$B^{200}$ is a group represented by formula ($B^2$-A) or formula ($B^2$-B).

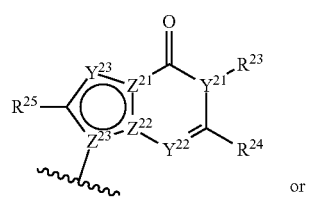

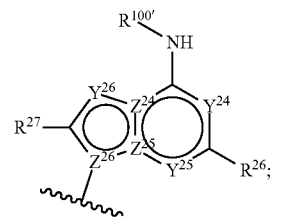

$R^{23}$, $R^{24}$, $R^{25}$, $R^{26}$ and $R^{27}$ are each independently a hydrogen atom or a substituent;
$R^{100'}$ is hydrogen or a bond to the carbonyl group of formula (I);
$Y^{21}, Y^{22}, Y^{23}, Y^{24}, Y^{25}$ and $Y^{26}$ are each independently N or $CR^{2a}$;
$Z^{21}, Z^{22}, Z^{23}, Z^{24}, Z^{25}$ and $Z^{26}$ are each independently N or C; and
$R^{2a}$ is a hydrogen atom or a substituent;
provided that one of $B^{100}$ or $B^{200}$ is attached to the carbonyl group of formula (I) through an —NH— group.

As described herein, compounds of formula (III) and formula (IIIa) (below) comprise substituents at certain positions. Suitable substituents include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group, wherein the optionally substituted groups have one or more substituents selected from substituent group A:

"Substituent group A:"
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),

(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

In some embodiments the STING modulator is a compound of formula (IIIa), or a pharmaceutically acceptable salt thereof:

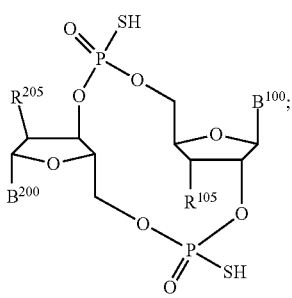

(IIIa)

or a pharmaceutically acceptable salt thereof; wherein $B^{100}$ is a group represented by formula ($B^1$-A) or formula ($B^1$-B):

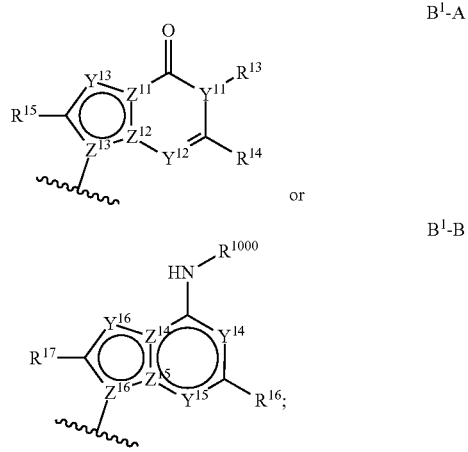

$R^{13}$, $R^{14}$, $R^{15}$, $R^{16}$ and $R^{17}$ are each independently a hydrogen atom or a substituent;
$R^{1000}$ is hydrogen or a bond to the carbonyl group of formula (I);
$Y^{11}$, $Y^{12}$, $Y^{13}$, $Y^{14}$, $Y^{15}$ and $Y^{16}$ are each independently N or $CR^{1a}$, wherein $R^{1a}$ is hydrogen or a substituent;
$Z^{11}$, $Z^{12}$, $Z^{13}$, $Z^{14}$, $Z^{15}$ and $Z^{16}$ are each independently N or C;
$R^{105}$ is a hydrogen atom or a substituent;
$B^{200}$ is a group represented by formula ($B^2$-A) or formula ($B^2$-B):

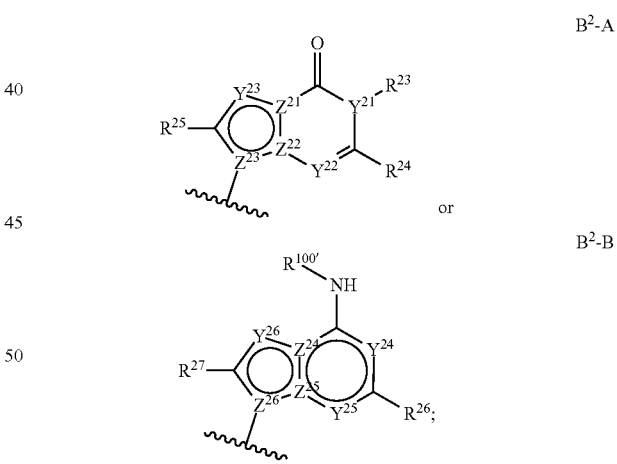

$R^{23}$, $R^{24}$, $R^{25}$, $R^{26}$ and $R^{27}$ are each independently a hydrogen atom or a substituent;
$R^{100'}$ is hydrogen or a bond to the carbonyl group of formula (I);
$Y^{21}$, $Y^{22}$, $Y^{23}$, $Y^{24}$, $Y^{25}$ and $Y^{26}$ are each independently N or $CR^{2a}$, wherein $R^{2a}$ is hydrogen or a substituent;
$Z^{21}$, $Z^{22}$, $Z^{23}$, $Z^{24}$, $Z^{25}$ and $Z^{26}$ are each independently N or C; and
$R^{205}$ is a hydrogen atom or a substituent; wherein $R^{105}$ and $R^{205}$ are each independently attached to 2- or 3-position of the 5-membered ring they are attached to respectively;

provided that:
one of $B^{100}$ or $B^{200}$ is:

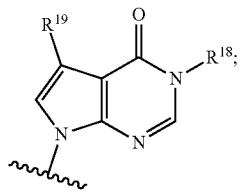

wherein:
$R^{18}$ is hydrogen or $C_{1-6}$ alkyl; and
$R^{19}$ is a halogen atom;
and the other is attached to the carbonyl group of formula (I) through an —NH— group.

In some embodiments the STING modulator is a compound of formula (IV), or a pharmaceutically acceptable salt thereof:

(IV)

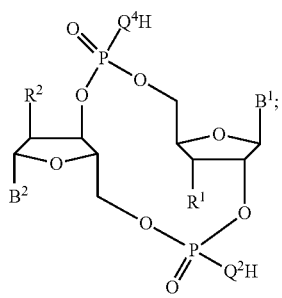

or a pharmaceutically acceptable salt thereof, wherein:
$R^1$ and $R^2$ are each independently a hydroxy group or a halogen atom;
B1 is:

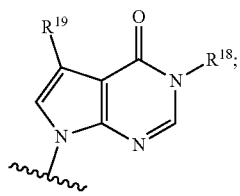

$R^{18}$ is hydrogen or $C_{1-6}$ alkyl;
$R^{19}$ is a halogen atom;
B2 is:

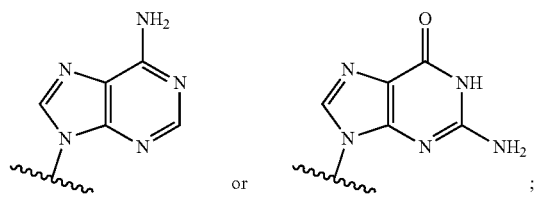 [SMILES: *n1cnc2c(N)ncnc21 ; *n1cnc2c(=O)[nH]c(N)nc21]

and
$Q^2$ and $Q^4$ are each independently an oxygen atom or a sulfur atom.

In some embodiments, the cyclic dinucleotide is:

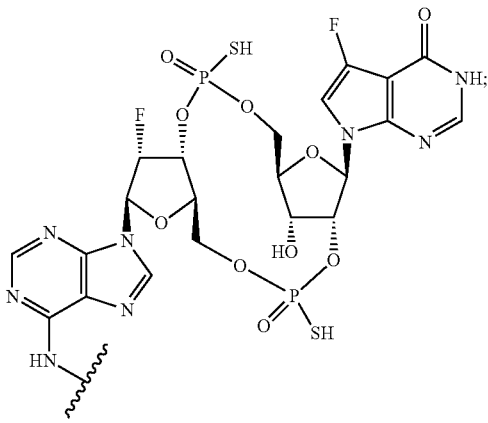 [SMILES: *Nc1ncnc2c1ncn2[C@@H]1O[C@@H]2COP(=O)(S)O[C@@H]3[C@H](O)[C@@H](COP(=O)(S)O[C@H]2[C@H]1F)O[C@H]3n1cc(F)c2c(=O)[nH]cnc21]

or a pharmaceutically acceptable salt thereof, wherein ⸺ is the point of 'L'.

Linker Moiety

The group "L" is a linker. As used herein, the term "linker" refers to any chemical moiety capable of connecting the antibody, antibody fragment, or antigen-binding fragment (Ab) to the drug-containing moiety within the compounds of formula (I) and (IV). The linker can be branched, and can be substituted with from 1 to 20 drug-containing moieties. In some embodiments, the linker can be substituted with from 1 to 10 drug-containing moieties. In some embodiments, the linker can be substituted with from 1 to 5 drug-containing moieties. In some embodiments, the linker can be substituted with one or two drug-containing moieties. In some embodiments, the linker can be substituted with one drug-containing moiety.

In some embodiments the linker "L" is a cleavable linker. In certain embodiments the linker can be susceptible to acid-induced cleavage, photo-induced cleavage, enzymatic cleavage, or the like, at conditions under which the drug and/or antibody can remain active. In some embodiments, the cleavable linker can be cleaved enzymatically. In some embodiments, the cleavable linker can be cleaved by a protease, peptidase, esterase, glycosidase, phosphodiesterase, phosphatase, or lipase. In some embodiments, the cleavable linker can be cleaved by a protease. Examples of proteases include, but are not limited to, cathepsin B, VAGP tetrapeptide, and the like.

In certain embodiments, the linker can be any of those disclosed in PCT publications WO 2018/200812, WO 2018/100558, which are incorporated by reference in their entireties.

In certain embodiments, "L" has the formula:

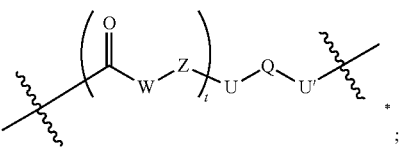

wherein:
⸺ is the point of attachment to the nitrogen atom; and
⸺ is the point of attachment to Ab.

In some embodiments, "L" has the formula:

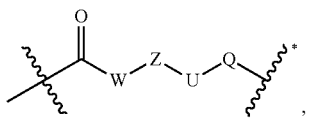

wherein:

⁂ is the point of attachment to the nitrogen atom;

⁂ is the point of attachment to the antibody;

The group "W" is absent or a self-immolative group. As used herein, the term "self-immolative," refers to a group that undergoes an electronic cascade which results in the release of the group to which it is attached. In some embodiments, the self-immolative group comprises one or more groups which can undergo 1,4-elimination, 1,6-elimination, 1,8-elimination, 1,6-cyclization elimination, 1,5-cyclization elimination, 1,3-cyclization elimination, intramolecular 5-exo-trig cyclization, and/or 6-exo-trig cyclization. In certain embodiments the self-immolative group can be any of those disclosed in PCT publications WO 2018/200812, WO 2018/100558, which are incorporated by reference in their entireties.

The group "Z" is absent or a peptide of 2 to 5 amino acids. In certain embodiments, the peptide is the site of cleavage of the linker, thereby facilitating release of the drug upon exposure to intracellular proteases, such as lysosomal enzymes (Doronina et al. (2003) Nat. Biotechnol. 21:778-784). Examples of peptides having two amino acids include, but are not limited to, alanine-alanine (Ala-Ala), valine-alanine (VA or Val-Ala), valine-citrulline (VC or Val-Cit), alanine-phenylalanine (AF or Ala-Phe); phenylalanine-lysine (FK or Phe-Lys); phenylalanine-homolysine (Phe-Homolys); and N-methyl-valine-citrulline (Me-Val-Cit). Examples of peptides having three amino acids include, but are not limited to, glycine-valine-citrulline (Gly-Val-Cit) and glycine-glycine-glycine (Gly-Gly-Gly). The amino acid combinations above can also be present in the reverse order (i.e., Cit-Val).

The peptides of the present disclosure may comprise naturally-occurring and/or non-natural amino acid residues. The term "naturally-occurring amino acid" refer to Ala, Asp, Cys, Glu, Phe, Gly, His, He, Lys, Leu, Met, Asn, Pro, Gin, Arg, Ser, Thr, Val, Trp, and Tyr. "Non-natural amino acids" (i.e., amino acids do not occur naturally) include, by way of non-limiting example, homoserine, homoarginine, citrulline, phenylglycine, taurine, iodotyrosine, seleno-cysteine, norleucine ("Nle"), norvaline ("Nva"), beta-alanine, L- or D-naphthalanine, ornithine ("Orn"), and the like. Peptides can be designed and optimized for enzymatic cleavage by a particular enzyme, for example, a tumor-associated protease, cathepsin B, C and D, or a plasmin protease.

Amino acids also include the D-forms of natural and non-natural amino acids. "D-" designates an amino acid having the "D" (dextrorotary) configuration, as opposed to the configuration in the naturally occurring ("L-") amino acids. Natural and non-natural amino acids can be purchased commercially (Sigma Chemical Co., Advanced Chemtech) or synthesized using methods known in the art.

The groups "U" and "U'" are independently absent or a spacer. As used herein, the term "spacer," refers to chemical moiety that serves as a connector. In the present disclosure the spacer can connect the antibody, antibody fragment, or antigen fragment to the heterobifunctional group and/or connect the heterobifunctional group to peptide "Z," or, when "Z" is absent, to group "W". Non-limiting exemplary spacers include —NH—, —S—, —O—, —NHC(=O)CH₂CH₂—, —S(=O)₂—CH₂CH₂—, —C(=O)NHNH—, —C(=O)O—, —C(=O)NH—, —CH₂—, —CH₂CH₂—, —CH₂CH₂CH₂—, —CH₂=CH₂—, —C≡C—, —CH=N—O—, polyethylene glycol (PEG),

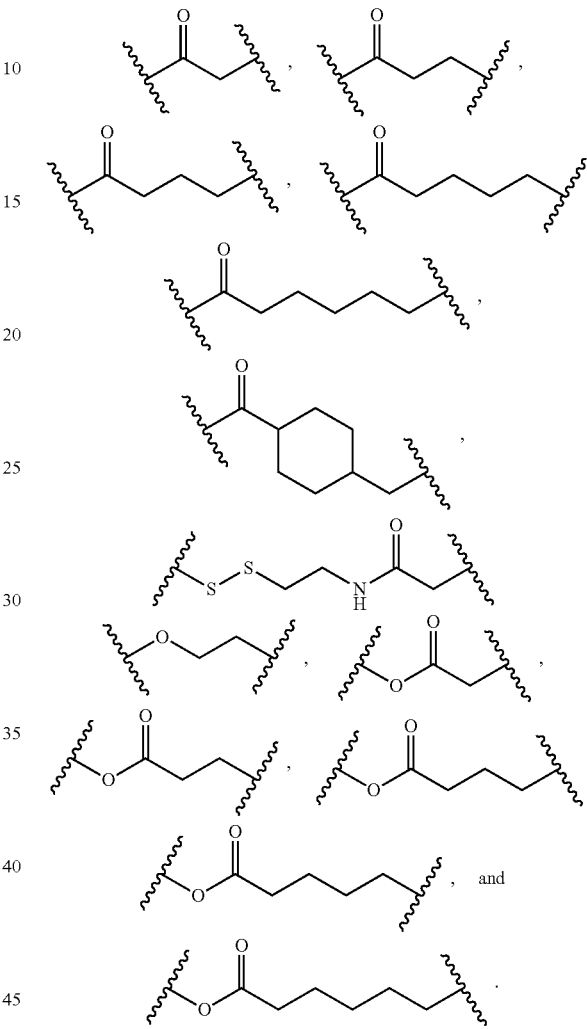

In the compounds of the present disclosure, when "U" is present, it can be a branched group substituted by from 1 to 10 "—C(O)—W—Z—" groups. In some embodiments, "U" is substituted by from 1 to 5 "—C(O)—W—Z—" groups. In some embodiments, "U" is substituted with 1 or 2 "—C(O)—W—Z—" groups. In some embodiments, "U" is substituted with 1 "—C(O)—W—Z—" group. In certain embodiments the spacer can be any of those disclosed in PCT publications WO 2018/200812, WO 2018/100558, which are incorporated by reference in their entireties.

Group "Q" is a heterobifunctional group. In the present disclosure, the term "heterobifunctional group" refers to a chemical moiety that connects the linker of which it is a part to the antibody, antibody fragment, or antigen-binding fragment. See, e.g., WO 2017/191579. Heterobifunctional groups are characterized as having different reactive groups at either end of the chemical moiety. The heterobifunctional group may be attached directly to "Ab," or alternatively, may connect through linker "U'". Attachment to "Ab," can be accomplished through chemical or enzymatic conjugation, or a combination of both. Chemical conjugation involves the controlled reaction of accessible amino acid residues on the surface of the antibody with a reaction handle on "Q" or "U'". Examples of chemical conjugation include, but are not limited to, lysine amide coupling, cysteine coupling, and coupling via a non-natural amino acid incorporated by genetic engineering, wherein non-natural amino acid residues with a desired reaction handle are installed onto "Ab". In enzymatic conjugation, an enzyme mediates the coupling of the linker with an accessible amino residue on the antibody, antibody fragment, or antigen-binding fragment. Examples of enzymatic conjugation include, but are not limited to, transpeptidation using sortase, transpeptidation using microbial transglutaminase, and N-glycan engineering. Chemical conjugation and enzymatic conjugation may also be used sequentially. For example, enzymatic conjugation can also be used for installing unique reaction handles on "Ab" to be utilized in subsequent chemical conjugation. In certain embodiments the heterobifunctional group can be any of those disclosed in PCT publications WO 2018/200812, WO 2018/100558, which are incorporated by reference in their entireties.

In some embodiments, "Q" is selected from

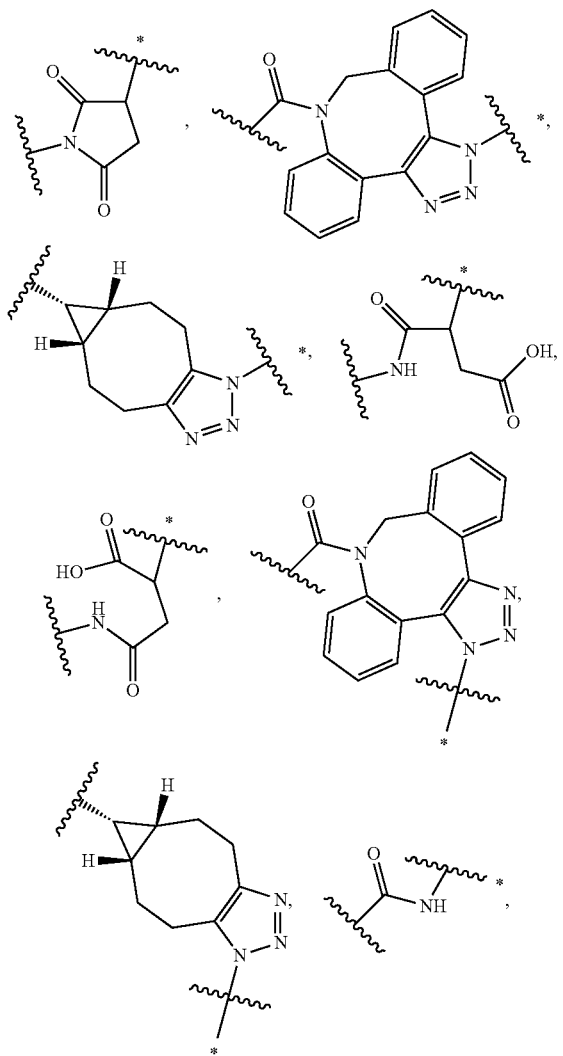

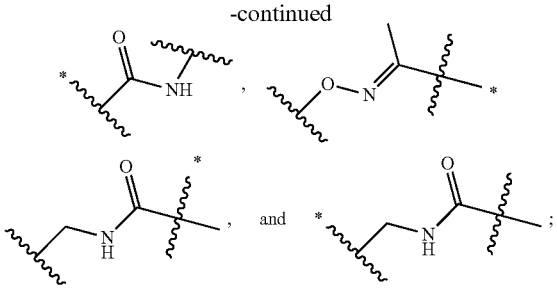

wherein

⌇ is the point of attachment to U, or, when U is absent, the point of attachment to Z; and ⌇ is the point of attachment to U', or, when U' is absent, the point of attachment to Ab.

In certain embodiments, the present disclosure provides a compound of formula (XX).

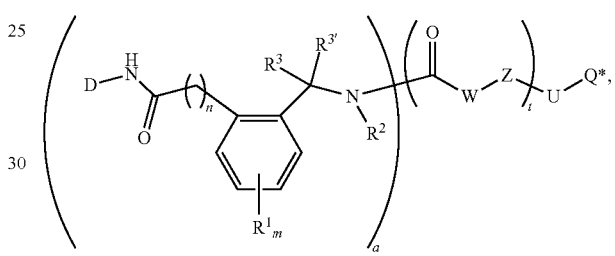

(XX)

or a pharmaceutically acceptable salt thereof, wherein n, m, a, t, D-NH—, $R^1$, $R^2$, $R^3$, $R^{3'}$, W, Z, and U are as described herein and wherein Q* is reactive functional group capable of conjugating to an antibody, antibody fragment, or antigen-binding fragment. Examples of suitable Q* groups include, but are not limited to, activated carboxylic acid groups, such as acid chloride —C(O)—Cl and acid anhydrides, haloacetamide, maleimide, alkyne, cycloalkyne, such as a cyclooctyne, oxanoboradiene, norbornene, azide, diaryl tetrazine, monoaryl tetrazine, aldehyde, ketone, hydroxylamine, vinylsulfone, and aziridine. In certain embodiments the reactive functional group can be any of those disclosed in PCT publications WO 2018/200812, WO 2018/100558, which are incorporated by reference in their entireties.

Anti-CCR2 Antibodies, Antibody Fragments, and Antigen-Binding Fragments

Group "Ab" is an anti-CCR2 antibody, anti-CCR2 antibody fragment, or an anti-CCR2 antigen-binding fragment. An antibody is a protein generated by the immune system that is capable of recognizing and binding to a specific antigen. A target antigen generally has numerous binding sites, also called epitopes, recognized by CDRs on multiple antibodies. Each antibody that specifically binds to a different epitope has a different structure. Thus, one antigen may have more than one corresponding antibody. The term "antibody" herein is used in the broadest sense and specifically covers monoclonal antibodies, single domain antibodies, polyclonal antibodies, multispecific antibodies (e.g., bispecific antibodies), and antibody fragments, so long as they exhibit the desired biological activity. Antibodies may be murine, human, humanized, chimeric, or derived from other species. (Janeway, C., Travers, P., Walport, M., Shlomchik (2001) Immuno Biology, 5th Ed., Garland Publishing, New York).

Useful anti-CCR2 antibodies, antibody fragments, and antigen-binding fragments include an antibody (immunoglobulin) or functional fragment thereof (e.g., an antigen-binding fragment) which binds to a mammalian CC-chemokine receptor 2 (also referred to as CCR2, CKR-2, CD192, MCP-1RA or MCP-1RB) or portion of the receptor. In one embodiment, the antibody or fragment thereof has specificity for human or rhesus CCR2 or a portion thereof. In another embodiment, the antibody or fragment blocks binding of a ligand (e.g., MCP-1, MCP-2, MCP-3, MCP-4) to the receptor and inhibits function associated with binding of the ligand to the receptor (e.g., leukocyte trafficking). For example, as described herein, antibodies and fragments thereof useful in the present disclosure bind human or rhesus CCR2 or a portion thereof, and can block binding of a chemokine (e.g., MCP-1, MCP-2, MCP-3, MCP-4) to the receptor and inhibit function associated with binding of the chemokine to the receptor. In one embodiment, the antibody is monoclonal antibody (mAb) LS132.1D9 (1D9) or an antibody which can compete with 1D9 for binding to human CCR2 or a portion of human CCR2. Functional fragments of the foregoing antibodies are also envisioned.

In some embodiments, a humanized immunoglobulin or antigen-binding fragment thereof having binding specificity for CCR2 is employed, said immunoglobulin comprising an antigen binding region of nonhuman origin (e.g., rodent) and at least a portion of an immunoglobulin of human origin (e.g., a human framework region, a human constant region of the gamma type). In one embodiment, the humanized immunoglobulin or fragment thereof can compete with 1D9 for binding to CCR2. In one embodiment, the antigen binding region of the humanized immunoglobulin is derived from monoclonal antibody 1D9 (e.g., an immunoglobulin comprising the variable regions of the light and heavy chains as shown below).

For example, the humanized immunoglobulin or antigen-binding fragment thereof can comprise an antigen binding region comprising at least one complementarity determining region (CDR) of nonhuman origin, and a framework region (FR) derived from a human framework region. In one aspect, the humanized immunoglobulin having binding specificity for CCR2 comprises a light chain comprising at least one CDR derived from an antibody of nonhuman origin which binds CCR2 and a FR derived from a light chain of human origin (e.g., from HF-21/28), and a heavy chain comprising a CDR derived from an antibody of nonhuman origin which binds CCR2 and a FR derived from a heavy chain of human origin (e.g., from 4B4'CL). In another aspect, the light chain comprises three CDRs derived from the light chain of the 1D9 antibody, and the heavy chain comprises three CDRs derived from the heavy chain of the 1D9 antibody.

In one embodiment, the humanized immunoglobulin having binding specificity for CCR2 comprises CDR1, CDR2 and CDR3 of the light chain of the 1D9 antibody, and a human light chain FR, and comprises CDR1, CDR2 and CDR3 of the heavy chain of the 1D9 antibody, and a human heavy chain FR. In one embodiment, the humanized immunoglobulin comprises the humanized heavy and light chains described herein (e.g., a humanized light chain comprising the variable region of the light chain shown below, a humanized heavy chain comprising the variable region of the heavy chain shown below. Also encompassed are humanized immunoglobulins comprising one or more humanized light and/or heavy chains.

The following shows the amino acid sequence of the kappa light chain variable region (VL) of the humanized 1D9 antibody. The CDRs are highlighted in bold:

```
                                               (SEQ ID NO: 1)
DVVMTQSPLS LPVTLGQPAS ISCKSSQSLL DSDGKTFLNW

FQQRPGQSPR RLIYLVSKLD SGVPDRFSGS GSGTDFTLKI

SRVEAEDVGV YYCWQGTHFP YTFGQGTRLE IK.
```

The following shows the amino acid sequence of the heavy chain variable region (VH) of the humanized 1D9 antibody. The CDRs are highlighted in bold:

```
                                               (SEQ ID NO: 2)
EVQLVESGGG LVKPGGSLRL SCAASGFTFS AYAMNWVRQA

PGKGLEWVGR IRTKNNNYAT YYADSVKDRF TISRDDSKNT

LYLQMNSLKT EDTAVYYCTT FYGNGVWGQG TLVTVSS.
```

In certain embodiments, the anti-CCR2 antibody, anti-CCR2 antibody fragment, or anti-CCR2 antigen-binding fragment comprises a light chain CDR1 comprising amino acids 24-39 of SEQ ID NO: 1; a light chain CDR2 comprising amino acids 55-61 of SEQ ID NO: 1; a light chain CDR3 comprising amino acids 94-102 of SEQ ID NO: 1; a heavy chain CDR1 comprising amino acids 31-35 of SEQ ID NO:2; a heavy chain CDR2 comprising amino acids 50-68 of SEQ ID NO:2; and a heavy chain CDR3 comprising amino acids 101-106 of SEQ ID NO:2.

In some embodiments, the anti-CCR2 antibody, anti-CCR2 antibody fragment, or anti-CCR2 antigen-binding fragment comprises a heavy chain variable region comprising the amino acid sequence of SEQ ID NO: 2.

In some embodiments, the anti-CCR2 antibody, anti-CCR2 antibody fragment, or anti-CCR2 antigen-binding fragment comprises a light chain variable region comprising the amino acid sequence of SEQ ID NO: 1.

In some embodiments, the anti-CCR2 antibody, anti-CCR2 antibody fragment, or anti-CCR2 antigen-binding fragment comprises a heavy chain variable region and a light chain variable region, wherein the heavy chain variable region comprises the amino acid sequence of SEQ ID NO: 2.

In some embodiments, the anti-CCR2 antibody, anti-CCR2 antibody fragment, or anti-CCR2 antigen-binding fragment comprises a heavy chain variable region and a light chain variable region, wherein the light chain variable region comprises the amino acid sequence of SEQ ID NO: 1.

In some embodiments, the anti-CCR2 antibody, anti-CCR2 antibody fragment, or anti-CCR2 antigen-binding fragment comprises a heavy chain variable region comprising the amino acid sequence of SEQ ID NO: 2 and a light chain variable region, wherein the light chain variable region comprises the amino acid sequence of SEQ ID NO: 1.

In certain embodiments, the anti-CCR2 antibody, anti-CCR2 antibody fragment, or anti-CCR2 antigen-binding fragment further comprises a heavy chain constant region. In some embodiments, the heavy chain constant region is selected from human immunoglobulins $IgG_1$, $IgG_2$, $IgG_3$, $IgG_4$, $IgA_1$, and $IgA_2$ heavy chain constant regions.

In some embodiments, the anti-CCR2 antibody, anti-CCR2 antibody fragment, or anti-CCR2 antigen-binding fragment further comprises a light chain constant region. In some embodiments, light chain constant region is selected from the group consisting of human immunoglobulins IgG$_\kappa$ and IgGλ light chain constant regions.

In certain embodiments, the anti-CCR2 antibody, anti-CCR2 antibody fragment, or anti-CCR2 antigen-binding fragment binds to the same epitope as an antibody comprising a variable heavy chain region of SEQ ID NO: 2 and a variable light chain region of SEQ ID NO: 1.

"Percent identity" refers to the extent of identity between two sequences (e.g., amino acid sequences or nucleic acid sequences). Percent identity can be determined by aligning two sequences, introducing gaps to maximize identity between the sequences. Alignments can be generated using programs known in the art. For purposes herein, alignment of nucleotide sequences can be performed with the blastn program set at default parameters, and alignment of amino acid sequences can be performed with the blastp program set at default parameters (see National Center for Biotechnology Information (NCBI) on the worldwide web, ncbi.nlm.nih.gov).

A CCR2 antibody that "binds to the same epitope" as a reference CCR2 antibody refers to an antibody that binds to the same CCR2 amino acid residues as the reference CCR2 antibody. The ability of a CCR2 antibody to bind to the same epitope as a reference CCR2 antibody is determined by a hydrogen/deuterium exchange assay (see Coales et al. Rapid Commun. Mass Spectrom. 2009; 23: 639-647).

In certain embodiments, an antibody or antigen-binding fragment thereof described herein binds to human CCR2, comprises the six CDRs of the antibody listed in SEQ ID NO: 1 and SEQ ID NO: 2, and comprises a VH comprising a sequence at least 80% identical to the VH sequence of SEQ ID NO: 2 and a VL comprising a sequence at least 80% identical to the VL sequence of SEQ ID NO: 1. In certain embodiments, an antibody or antigen-binding fragment thereof described herein binds to human CCR2, comprises the six CDRs of the antibody listed in SEQ ID NO: 1 and SEQ ID NO: 2 (i.e., the three VH CDRs of the antibody listed in SEQ ID NO: 2 and the three VL CDRs of SEQ ID NO: 1), and comprises a VH comprising a sequence at least 85% identical to the VH sequence of SEQ ID NO: 2 and a VL comprising a sequence at least 85% identical to the VL sequence of SEQ ID NO: 1.

In certain embodiments, an antibody or antigen-binding fragment thereof described herein binds to human CCR2, comprises the six CDRs of the antibody listed SEQ ID NO: 1 and SEQ ID NO: 2 (i.e., the three VH CDRs of SEQ ID NO: 2 and the three VL CDRs of SEQ ID NO: 1), and comprises a VH comprising a sequence at least 90% identical to the VH sequence of SEQ ID NO: 2 and a VL comprising a sequence at least 90% identical to the VL sequence of SEQ ID NO: 1. In certain embodiments, an antibody or antigen-binding fragment thereof described herein binds to human CCR2, comprises the six CDRs of the antibody listed in SEQ ID NO: 1 and SEQ ID NO: 2 (i.e., the three VH CDRs of the antibody and the three VL CDRs of SEQ ID NO: 1), and comprises a VH comprising a sequence at least 95% identical to the VH sequence of SEQ ID NO: 2 and a VL comprising a sequence at least 95% identical to the VL sequence of SEQ ID NO: 1.

In certain embodiments, an antibody or antigen-binding fragment thereof described herein binds to human CCR2, comprises the six CDRs of the antibody listed in SEQ ID NO: 1 and SEQ ID NO: 2 (i.e., the three VH CDRs of SEQ ID NO: 2 and the three VL CDRs of the SEQ ID NO: 1), and comprises a VH comprising a sequence at least 96% identical to the VH sequence of SEQ ID NO: 2 and a VL comprising a sequence at least 96% identical to the VL sequence of SEQ ID NO: 1. In certain embodiments, an antibody or antigen-binding fragment thereof described herein binds to human CCR1, comprises the six CDRs of the antibody listed in SEQ ID NO: 1 and SEQ ID NO: 2 (i.e., the three VH CDRs of SEQ ID NO: 2 and the three VL CDRs of SEQ ID NO: 1), and comprises a VH comprising a sequence at least 97% identical to the VH sequence of SEQ ID NO: 2 and a VL comprising a sequence at least 970% identical to the VL sequence of SEQ ID NO: 1. In certain embodiments, an antibody or antigen-binding fragment thereof described herein binds to human CCR2, comprises the six CDRs of the antibody listed in SEQ ID NO: 1 and SEQ ID NO: 2 (i.e., the three VH CDRs of SEQ ID NO: 2 and the three VL CDRs of SEQ ID NO: 1), and comprises a VH comprising a sequence at least 98% identical to the VH sequence of SEQ ID NO: 2 and a VL comprising a sequence at least 98% identical to the VL sequence of SEQ ID NO: 1. In certain embodiments, an antibody or antigen-binding fragment thereof described herein binds to human CCR2, comprises the six CDRs of the antibody listed in SEQ ID NO: 1 and SEQ ID NO: 2 (i.e., the three VH CDRs of SEQ ID NO: 2 the three VL CDRs of SEQ ID NO: 1), and comprises a VH comprising a sequence at least 99% identical to the VH sequence of SEQ ID NO: 2 and a VL comprising a sequence at least 99% identical to the VL sequence of SEQ ID NO: 1.

In certain embodiments, an antibody or antigen-binding fragment thereof described herein binds to human CCR2, comprises the six CDRs of the antibody listed in SEQ ID NO: 1 and SEQ ID NO: 2 (i.e., the three VH CDRs of SEQ ID NO: 2 and the three VL CDRs of SEQ ID NO: 1), comprises a VH comprising a sequence at least 80% identical to the VH sequence of SEQ ID NO: 2 and a VL comprising a sequence at least 80% identical to the VL sequence of SEQ ID NO: 1, and binds to human, cynomolgus monkey, rat, and/or mouse CCR2. In certain embodiments, an antibody or antigen-binding fragment thereof described herein binds to CCR2, comprises the six CDRs of the antibody listed in SEQ ID NO: 1 and SEQ ID NO: 2 (i.e., the three VH CDRs of SEQ ID NO: 2 and the three VL CDRs of SEQ ID NO: 1), comprises a VH comprising a sequence at least 85% identical to the VH sequence of SEQ ID NO: 2 and a VL comprising a sequence at least 85% identical to the VL sequence of SEQ ID NO: 1, and binds to human, cynomolgus monkey, rat, and/or mouse CCR2.

In certain embodiments, an antibody or antigen-binding fragment thereof described herein binds to human CCR2, comprises the six CDRs of the antibody listed in SEQ ID NO: 1 and SEQ ID NO: 2 (i.e., the three VH CDRs of the antibody and the three VL CDRs of SEQ ID NO: 1), comprises a VH comprising a sequence at least 90% identical to the VH sequence of SEQ ID NO: 2 and a VL comprising a sequence at least 90% identical to the VL sequence of SEQ ID NO: 1, and binds to human, cynomolgus monkey, rat, and/or mouse CCR2. In certain embodiments, an antibody or antigen-binding fragment thereof described herein binds to human CCR2, comprises the six CDRs of the antibody listed in SEQ ID NO: 1 and SEQ ID NO: 2 (i.e., the three VH CDRs of SEQ ID NO: 2 and the three VL CDRs of SEQ ID NO: 1), comprises a VH comprising a sequence at least 95% identical to the VH sequence of SEQ ID NO: 2 and a VL comprising a sequence at least 95% identical to the VL sequence of SEQ ID NO: 1, and binds to human, cynomolgus monkey, rat, and/or mouse CCR2.

In certain embodiments, an antibody or antigen-binding fragment thereof described herein binds to human CCR2, comprises the six CDRs of the antibody listed in SEQ ID NO: 1 and SEQ ID NO: 2 (i.e., the three VH CDRs of SEQ ID NO: 2 and the three VL CDRs of SEQ ID NO: 1), comprises a VH comprising a sequence at least 96% identical to the VH sequence of SEQ ID NO: 2 and a VL comprising a sequence at least 96% identical to the VL sequence of SEQ ID NO: 1, and binds to human, cynomolgus monkey, rat, and/or mouse CCR2. In certain embodiments, an antibody or antigen-binding fragment thereof described herein binds to human CCR2, comprises the six CDRs of the antibody listed in SEQ ID NO: 1 and SEQ ID NO: 2 (i.e., the three VH CDRs of SEQ ID NO: 2 and the three VL CDRs of SEQ ID NO: 1, comprises a VH comprising a sequence at least 97% identical to the VH sequence of SEQ ID NO: 2 and a VL comprising a sequence at least 97% identical to the VL sequence of SEQ ID NO: 1, and binds to human, cynomolgus monkey, rat, and/or mouse CCR2. In certain embodiments, an antibody or antigen-binding fragment thereof described herein binds to human CCR2, comprises the six CDRs of the antibody listed in SEQ ID NO: 1 and SEQ ID NO: 2 (i.e., the three VH CDRs of SEQ ID NO: 2 and the three VL CDRs of SEQ ID NO: 1), comprises a VH comprising a sequence at least 98% identical to the VH sequence of SEQ ID NO: 2 and a VL comprising a sequence at least 98% identical to the VL sequence of SEQ ID NO: 1, and binds to human, cynomolgus monkey, rat, and/or mouse CCR2. In certain embodiments, an antibody or antigen-binding fragment thereof described herein binds to human CCR2, comprises the six CDRs of the antibody listed in SEQ ID NO: 1 and SEQ ID NO: 2 (i.e., the three VH CDRs of SEQ ID NO: 2 and the three VL CDRs of SEQ ID NO: 1), comprises a VH comprising a sequence at least 99% identical to the VH sequence of SEQ ID NO: 2 and a VL comprising a sequence at least 99% identical to the VL sequence of SEQ ID NO: 1, and binds to human, cynomolgus monkey, rat, and/or mouse CCR2.

In certain embodiments, a compound of formula (I) is combined with an antibody, antibody fragment or antigen-binding fragment of an antibody that binds PD-1 and/or an antibody, antibody fragment and/or antigen-binding fragment of an antibody that binds PD-L1. PD-1 is an immune checkpoint protein expressed on activated T cells, B cells, and monocytes that, upon binding of its ligand PD-L1, regulates the immune system, e.g., by promoting apoptosis of antigen-specific T cells and reducing apoptosis of regulatory T cells. PD-L1 can be expressed by tumors to help tumors evade detection and elimination by the immune system. Antagonistic inhibition of the PD-1/PD-L1 interaction advantageously increases T cell activation and enhances recognition and elimination of tumor cells by the immune system. In certain embodiments, the anti-PD-1 antibody is selected from the group consisting of Pembrolizumab, Nivolumab, Cemiplimab, Pimivalimab, Spartalizumab, Camrelizumab, Sintilimab, Tislelizumab, Toripalimab, Dostarlimab, Ezabenlimab, INCMGA0012, AMP-224, AMP-514, SYM-021, LZM-009, CS-1003, SYN-125, GNR-051, MW-11, TY-101, BAT-1306, F520, Sasanlimab, Penpulimab, Pucotenlimab, CX-188, Zimberelimab, and Tebotelimab, or an antibody which can compete with Pembrolizumab, Nivolumab, Cemiplimab, Pimivalimab, Spartalizumab, Camrelizumab, Sintilimab, Tislelizumab, Toripalimab, Dostarlimab, Ezabenlimab, INCMGA0012, AMP-224, AMP-514, SYM-021, LZM-009, CS-1003, SYN-125, GNR-051, MW-11, TY-101, BAT-1306, F520, Sasanlimab, Penpulimab, Pucotenlimab, CX-188, Zimberelimab, or Tebotelimab for binding to human PD-1 or a portion of PD-1.

In some embodiments, the anti-PD-1 antibody is Pembrolizumab.

In certain embodiments, the anti-PD-L1 antibody is selected from the group consisting Atezolizumab, Avelumab, Durvalumab, Cosibelimab, MSB-2311, ZKAB-001, FAZ-053, MDX-1105, CBT-502, IMC-001, RC-98, KL-A167, GR-1405, Lodapolimab, Sugemalimab, Envafolimab, Opucolimab, and Garivulimab, or an antibody which can compete with Atezolizumab, Avelumab, Durvalumab, Cosibelimab, MSB-2311, ZKAB-001, FAZ-053, MDX-1105, CBT-502, IMC-001, RC-98, KL-A167, GR-1405, Lodapolimab, Sugemalimab, Envafolimab, Opucolimab, or Garivulimab for binding to human PD-L1 or a portion of PD-L1.

In some embodiments, the anti-PD-L1 antibody is Atezolizumab.

Further anti-PD-1 antibodies useful in combination with a compound of formula (I) are NAT105 (abcam ab5287); CAL20 (abcam ab237728); EPR20665 (abcam ab214421); NAT105-chimeric (abcam ab216352); EPR4877(2) (abcam ab137132); EP23119-111 (abcam ab 243644); SP269 (abeam ab227681); PDCD1/1410R (abeam ab218475); EH12.22H7 (abeam ab 223562); PDCD1/922 (abeam ab216037); J43 (abeam ab95789); J43.1 (abeam ab 218768); SPM597 (abeam ab218474); J116 (abeam ab171267); RMP1-14 (abeam ab171265); EPR18017-203 (abeam ab242810); EPR18017-253 (abeam ab242562); EPR22234-127 (abeam ab259656); EPR22234-42 (abeam ab259655); MAB10861 (R&D Systems); MAB10864 (R&D Systems); MAB1086 (R&D Systems); MAB10863 (R&D Systems); MAB8578 (R&D Systems); MAB77381 (R&D Systems); MAB7738 (R&D Systems); MAB10866 (R&D Systems); MAB10865 (R&D Systems); MAB10867 (R&D Systems); SJ01-91 (HUABIO); 1F2 (HUABIO); 3A11 PD-1 blocking Ab (HUABIO); J43 (MyBioSource); RMP1-30 (MyBioSource); 8A1 (BIOSS Inc.); BSR1 (Abeomics); PDCD1/922 (Abeomics); PD1.3.1.3 (Miltenyi Biotec); abx174170 (Abbexa); PDCD1 (Fitzgerald Industries Intl.); J116 (United States Biological); BSR1 (Nordic BioSite); PDCD1 (BosterBio); 10B3 (ProSci Inc.); 4C$_7$ (ProSci Inc.); mhT28 blocking (Sino Biological Inc.); H1F06 neutralizing (Sino Biological Inc.); or TK12-02 (Creative Diagnostics) or an antibody which can compete with anyone of the foregoing antibodies for binding to PD-1 or a portion of PD-1.

Further anti-PD-L1 antibodies useful in combination with a compound of formula (I) are 28-8 (abeam ab205921); EPR19759 (abeam ab213524); CAL10 (abeam ab237726); 73-10 (abeam ab228415); EPR20529 (abeam ab213480); SP142 (abeam ab228462); BLR020E (abeam ab243877); RM1012 (abeam ab282458); EPR23546-160 (abeam ab252436); ABM4E54 (abeam ab210931); PDL1/2744 (abeam ab269674); MIH5 (abeam ab269253); 29E.2A3 (abeam ab259283); MIH6 (abeam ab80276); BMS-5-28 (abeam ab278010); EPR23939-25 (abeam ab278009); MAB1561 (R&D Systems); MAB90871 (R&D Systems); MAB1562 (R&D Systems); MAB90783 (R&D Systems); MAB10348 (R&D Systems); MAB1561R (R&D Systems); MAB9078 (R&D Systems); MAB10355 (R&D Systems); MIH1 (Invitrogen); MIH5 (Invitrogen); RM320 (Invitrogen); JJ08-95 (Invitrogen); 485 (Invitrogen); MA5-37856 (Invitrogen); 10D4 (Invitrogen); 15 (Invitrogen); 1-111A (Invitrogen); 2B11D11 (Proteintech); OTI2C7 (OriGene); UMAB228 (OriGene); OR-5H8 (OriGene); OTI9E12 (OriGene); UMAB229 (OriGene); OTI11G4 (OriGene);

OTI2C11 (OriGene); OTI14H4 (OriGene); OTI7D4 (OriGene); OTI9E1 (OriGene); OTI11G4 (OriGene); OTI2F5 (OriGene); OTI9A5 (OriGene); OTI3F5 (OriGene); OTI4G4 (OriGene); OTI9E5 (OriGene); OTI13G7 (OriGene); OTI9E10 (OriGene); OTI20G10 (OriGene); OR-5E3 (OriGene); OTI4D4 (OriGene); OTI13D11 (OriGene); OTI8C8 (OriGene); OTI16H9 (OriGene); OTI12G7 (OriGene); OTI1B12 (OriGene); OTI2E3 (OriGene); OTI2B12 (OriGene); OR-5E4 (OriGene); BLR020E (Bethyl Laboratories); 3F2 (Abnova); 3D2 (Abnova); 2E6 (Abnova); 2E11 (Abnova); 1H3 (Abnova); 2C4 (Abnova); Ac10 (Abnova); 3C10 (Abnova); or 4C11 (Abnova) or an antibody which can compete with any of the foregoing antibodies for binding to PD-L1 or a portion of PD-L1.

The term "antibody," as used herein, also refers to a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

The term "single domain antibody," also known as a nanobody, is an antibody fragment consisting of a single monomeric variable antibody domain with a molecular weight of from about 12 kDa to about 15 kDa. Single body antibodies can be based on heavy chain variable domains or light chains. Examples of single domain antibodies include, but are not limited to, $V_HH$ fragments and $V_{NAR}$ fragments. See, for example, Harmsen M. M. et al. *Applied Microbiology and Biotechnology* 77 (1): 13-22.

"Antibody fragments" comprise a portion of an intact antibody, generally the antigen binding or variable region thereof. Examples of antibody fragments include Fab, Fab', F(ab').sub.2, and Fv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

An "intact antibody" is one which comprises an antigen-binding variable region as well as a light chain constant domain (CL) and heavy chain constant domains, CH1, CH2 and CH3. The constant domains may be native sequence constant domains (e.g., human native sequence constant domains) or amino acid sequence variant thereof.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al (1975) Nature 256:495, or may be made by recombinant DNA methods (see, U.S. Pat. No. 4,816,567). The "monoclonal antibodies" may also be isolated from phage antibody libraries using the techniques described in Clackson et al (1991) Nature, 352:624-628; Marks et al (1991) J. Mol. Biol., 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape etc.) and human constant region sequences.

Various methods have been employed to produce monoclonal antibodies (MAbs). Hybridoma technology, which refers to a cloned cell line that produces a single type of antibody, uses the cells of various species, including mice (murine), hamsters, rats, and humans. Another method to prepare MAbs uses genetic engineering including recombinant DNA techniques. Monoclonal antibodies made from these techniques include, among others, chimeric antibodies and humanized antibodies. A chimeric antibody combines DNA encoding regions from more than one type of species. For example, a chimeric antibody may derive the variable region from a mouse and the constant region from a human. A humanized antibody comes predominantly from a human, even though it contains nonhuman portions. Like a chimeric antibody, a humanized antibody may contain a completely human constant region. But unlike a chimeric antibody, the variable region may be partially derived from a human. The nonhuman, synthetic portions of a humanized antibody often come from CDRs in murine antibodies. In any event, these regions are crucial to allow the antibody to recognize and bind to a specific antigen. While useful for diagnostics and short-term therapies, murine antibodies cannot be administered to people long-term without increasing the risk of a deleterious immunogenic response. This response, called Human Anti-Mouse Antibody (HAMA), occurs when a human immune system recognizes the murine antibody as foreign and attacks it. A HAMA response can cause toxic shock or even death.

Chimeric and humanized antibodies reduce the likelihood of a HAMA response by minimizing the nonhuman portions of administered antibodies. Furthermore, chimeric and humanized antibodies can have the additional benefit of activating secondary human immune responses, such as antibody dependent cellular cytotoxicity.

The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called .alpha., .delta., .epsilon., .gamma., and .mu., respectively. The subunit structures and three-dimensional configurations of different classes of immunoglobulins are well known.

Useful non-immunoreactive protein, polypeptide, or peptide antibodies include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-.alpha. and TGF-.beta., vaccinia growth factor ("VGF"), insulin and insulin-like growth factors I and II, lectins and apoprotein from low density lipoprotein.

Useful polyclonal antibodies are heterogeneous populations of antibody molecules derived from the sera of immunized animals. Various procedures well known in the art may be used for the production of polyclonal antibodies to an antigen-of-interest. For example, for the production of polyclonal antibodies, various host animals can be immunized by injection with an antigen of interest or derivative thereof, including but not limited to rabbits, mice, rats, and guinea pigs. Various adjuvants may be used to increase the immunological response, depending on the host species, and including but not limited to Freund's (complete and incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture. These include, but are not limited to, the hybridoma technique originally described by Kohler and Milstein (1975, Nature 256, 495-497), the human B cell hybridoma technique (Kozbor et al., 1983, Immunology Today 4:72), and the EBV-hybridoma technique (Cole et al., 1985, Monoclonal Antibodies and Cancer Therapy, Alan R. Liss, Inc., pp. 77-96). Such antibodies may be of any immunoglobulin class including IgG, IgM, IgE, IgA, and IgD and any subclass thereof. The hybridoma producing the mAbs used in this disclosure may be cultivated in vitro or in vivo.

Useful monoclonal antibodies include, but are not limited to, human monoclonal antibodies, humanized monoclonal antibodies, antibody fragments, or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80, 7308-7312; Kozbor et al., 1983, Immunology Today 4, 72-79; and Olsson et al., 1982, Meth. Enzymol. 92, 3-16).

The antibody can also be a bispecific antibody. Methods for making bispecific antibodies are known in the art. Traditional production of full-length bispecific antibodies is based on the coexpression of two immunoglobulin heavy chain-light chain pairs, where the two chains have different specificities (Milstein et al., 1983, Nature 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually performed using affinity chromatography steps, is rather cumbersome, and the product yields are low. Similar procedures are disclosed in WO 93/08829, and in Traunecker et al., EMBO J. 10:3655-3659 (1991).

According to a different approach, antibody variable domains with the desired binding specificities (antibody-antigen combining sites) are fused to immunoglobulin constant domain sequences. The fusion may be with an immunoglobulin heavy chain constant domain, comprising at least part of the hinge, C.sub.H2, and C.sub.H3 regions. The first heavy-chain constant region (C.sub.H1) may contain the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

Bispecific antibodies may have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (WO 94/04690; Suresh et al., Methods in Enzymology, 1986, 121:210; Rodrigues et al., 1993, J. of Immunology 151:6954-6961; Carter et al., 1992, Bio/Technology 10:163-167; Carter et al., 1995, J. of Hematotherapy 4:463-470; Merchant et al., 1998, Nature Biotechnology 16:677-681. Using such techniques, bispecific antibodies can be prepared for conjugation as ADC in the treatment or prevention of disease as defined herein.

Hybrid or bifunctional antibodies can be derived either biologically, i.e., by cell fusion techniques, or chemically, especially with cross-linking agents or disulfide-bridge forming reagents, and may comprise whole antibodies or fragments thereof (EP 105360; WO 83/03679; EP 217577).

The antibody can be a functionally active fragment, derivative or analog of an antibody that immunospecifically binds to cancer cell antigens, viral antigens, or microbial antigens or other antibodies bound to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (See, for e.g., Kabat et al., 1991, Sequences of Proteins of Immunological Interest, Fifth Edition, National Institute of Health, Bethesda, Md.; Kabat E et al., 1980, J. of Immunology 125 (3):961-969).

Other useful antibodies include fragments of antibodies such as, but not limited to, F(ab')2 fragments, which contain the variable region, the light chain constant region and the CH1 domain of the heavy chain can be produced by pepsin digestion of the antibody molecule, and Fab fragments, which can be generated by reducing the disulfide bridges of the F(ab')2 fragments. Other useful antibodies are heavy chain and light chain dimers of antibodies, or any minimal fragment thereof such as Fvs or single chain antibodies (SCAs) (e.g., as described in U.S. Pat. No. 4,946,778; Bird, 1988, Science 242:423-42; Huston et al., 1988, *Proc. Natl. Acad. Sci. USA* 85:5879-5883; and Ward et al., (1989) *Nature* 334:544-54), or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as those having a variable region derived from a murine monoclonal and human immunoglobulin constant regions. (See, e.g., Cabilly et al., U.S. Pat. No. 4,816,567; and Boss et al., U.S. Pat. No. 4,816,397). Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089) Such chimeric and humanized monoclonal antibodies can be produced by recombinant DNA techniques known in the art, for example using methods described in WO 87/02671; EP 184,187; EP 171496; EP 173494; WO 86/01533; U.S. Pat. No. 4,816,567; EP 12023; Berter et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Cancer. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, BioTechniques 4: 214; U.S. Pat. No. 5,225,539; Jones et al., 1986, Nature 321:552-525; Verhoeyan et al. (1988) Science 239:1534; and Beidler et al., 1988, J. Immunol. 141:4053-4060.

Completely human antibodies can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the disclosure. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies. See, e.g., U.S. Pat. Nos. 5,625,126; 5,633,425; 5,569,825; 5,661,016; 5,545,806. Other human antibodies can be obtained commercially from, for example, Abgenix, Inc. (Freemont, Calif.) and Genpharm (San Jose, Calif.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) Biotechnology 12:899-903). Human antibodies can also be produced using various techniques known in the art, including phage display libraries (Hoogenboom and Winter, J. Mol. Biol., 227:381 (1991); Marks et al., J. Mol. Biol., 222:581 (1991)).

The antibody may be a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, such as at least 10, 20 or 50 amino acid portion of the protein) that is not the antibody. The antibody or fragment thereof may be covalently linked to the other protein at the N-terminus of the constant domain.

Antibodies include analogs and derivatives that are either modified, i.e., by the covalent attachment of any type of molecule as long as such covalent attachment permits the antibody to retain its antigen binding immunospecificity. For example, but not by way of limitation, the derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including, but not limited to specific chemical cleavage, acetylation, formylation, metabolic synthesis in the presence of tunicamycin, etc. Additionally, the analog or derivative can contain one or more unnatural amino acids.

The antibodies in antibody drug conjugates include antibodies having modifications (e.g., substitutions, deletions or additions) in amino acid residues that interact with Fc receptors. In particular, antibodies include antibodies having modifications in amino acid residues identified as involved in the interaction between the anti-Fc domain and the FcRn receptor (see, e.g., WO 97/34631). Antibodies immunospecific for a cancer cell antigen can be obtained commercially, for example, from Genentech (San Francisco, Calif.) or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing.

The antibody of the ADC may be a monoclonal antibody, e.g. a murine monoclonal antibody, a chimeric antibody, or a humanized antibody. The antibody may be an antibody fragment, e.g. a Fab fragment.

Known anti-CCR2 antibodies for the treatment or prevention of cancer can be conjugated as ADCs. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, STI-B020X (anti-CCR2 monoclonal antibodies, Sorrento Therapeutics), MC-21 (anti-CCR2 humanized antibodies, University of Regensburt/MRC; described in EP Patent No. 2004692 which is incorporated herein by reference), 4.40A68G (Pfizer/Amgen; described in U.S. Pat. No. 8,710,191 which is incorporated herein by reference), UniTI-101 (CSF-1R x CCR2 bispecific antibodies, Elstar Therapeutics), and those described in WO97/31949, which is incorporated herein by reference.

The term "amino acid sequence variant" refers to polypeptides having amino acid sequences that differ to some extent from a native sequence polypeptide. Ordinarily, amino acid sequence variants will possess at least about 70% sequence identity with at least one receptor binding domain of a native antibody or with at least one ligand binding domain of a native receptor, and typically, they will be at least about 80%, more typically, at least about 90% homologous by sequence with such receptor or ligand binding domains. The amino acid sequence variants possess substitutions, deletions, and/or insertions at certain positions within the amino acid sequence of the native amino acid sequence. Amino acids are designated by the conventional names, one-letter and three-letter codes.

"Sequence identity" is defined as the percentage of residues in the amino acid sequence variant that are identical after aligning the sequences and introducing gaps, if necessary, to achieve the maximum percent sequence identity. Methods and computer programs for the alignment are well known in the art. One such computer program is "Align 2," authored by Genentech, Inc., which was filed with user documentation in the United States Copyright Office, Washington, D.C. 20559, on Dec. 10, 1991.

The terms "Fc receptor" or "FcR" are used to describe a receptor that binds to the Fc region of an antibody. An exemplary FcR is a native sequence human FcR. Moreover, a FcR may be one which binds an IgG antibody (a gamma receptor) and includes receptors of the Fc.gamma.RI, Fc.gamma.RII, and Fc.gamma. RIII subclasses, including allelic variants and alternatively spliced forms of these receptors. Fc.gamma.RII receptors include Fc.gamma.RIIA (an "activating receptor") and Fc.gamma.RIIB (an "inhibiting receptor"), which have similar amino acid sequences that differ primarily in the cytoplasmic domains thereof. Activating receptor Fc.gamma.RIIA contains an immunoreceptor tyrosine-based activation motif (ITAM) in its cytoplasmic domain. Inhibiting receptor Fc.gamma.RIIB contains an immunoreceptor tyrosine-based inhibition motif (ITIM) in its cytoplasmic domain. (See review M. in Daeron, Annu. Rev. Immunol., 15:203-234 (1997)). FcRs are reviewed in Ravetch and Kinet, Annu. Rev. Immunol., 9:457-92 (1991); Capel et al., Immunomethods, 4:25-34 (1994); and de Haas et al., J. Lab. Clin. Med., 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol., 117:587 (1976) and Kim et al., J. Immunol., 24:249 (1994)).

"Complement dependent cytotoxicity" or "CDC" refers to the ability of a molecule to lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santoro et al., J. Immunol. Methods, 202:163 (1996), may be performed.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a .beta.-sheet configuration, connected by three hypervariable regions, which form loops connecting, and in some cases forming part of, the .beta.-sheet structure. The hypervariable regions in each chain are held together in close proximity by the FRs and, with the hypervariable regions from the other chain, contribute to the formation of the antigen-binding site of antibodies (see Kabat et al (1991) Sequences of Proteins of Immunological Interest, 5th Ed. Public Health Service, National Institutes of Health, Bethesda, Md.). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g., residues 24-34 (L1), 50-56 (L2) and 89-97 (L3) in the light chain variable domain and 31-35 (H1), 50-65 (H2) and 95-102 (H3) in the heavy chain variable domain; Kabat et al supra) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk (1987) J. Mol. Biol., 196:901-917). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc"

fragment, whose name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa and lambda, based on the amino acid sequences of their constant domains.

"Single-chain Fv" or "scFv" antibody fragments comprise the VH and VL domains of antibody, wherein these domains are present in a single polypeptide chain. The Fv polypeptide may further comprise a polypeptide linker between the VH and VL domains which enables the scFv to form the desired structure for antigen binding. For a review of scFv, see Pluckthun in The Pharmacology of Monoclonal Antibodies, vol. 113, Rosenburg and Moore eds., Springer-Verlag, New York, pp. 269-315 (1994). Anti-ErbB2 antibody scFv fragments are described in WO 93/16185; U.S. Pat. Nos. 5,571,894; and 5,587,458.

The term "diabodies" refers to small antibody fragments with two antigen-binding sites, which fragments comprise a variable heavy domain (VH) connected to a variable light domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al (1993) Proc. Natl. Acad. Sci. USA 90:6444-6448.

"Humanized" forms of non-human (e.g., rodent) antibodies are chimeric antibodies that contain minimal sequence derived from non-human immunoglobulin. Humanization is a method to transfer the murine antigen binding information to a non-immunogenic human antibody acceptor, and has resulted in many therapeutically useful drugs. The method of humanization generally begins by transferring all six murine complementarity determining regions (CDRs) onto a human antibody framework (Jones et al, (1986) Nature 321:522-525). These CDR-grafted antibodies generally do not retain their original affinity for antigen binding, and in fact, affinity is often severely impaired. Besides the CDRs, select non-human antibody framework residues must also be incorporated to maintain proper CDR conformation (Chothia et al (1989) Nature 342:877). The transfer of key mouse framework residues to the human acceptor in order to support the structural conformation of the grafted CDRs has been shown to restore antigen binding and affinity (Riechmann et al., (1992) J. Mol. Biol. 224, 487-499; Foote and Winter, (1992) J. Mol. Biol. 224:487-499; Presta et al., (1993) J. Immunol. 151, 2623-2632; Werther et al., (1996) J. Immunol. Methods 157:4986-4995; and Presta et al (2001) Thromb. Haemost. 85:379-389). For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see U.S. Pat. No. 6,407,213; Jones et al (1986) Nature, 321:522-525; Riechmann et al (1988) Nature 332:323-329; and Presta, (1992) Curr. Op. Struct. Biol., 2:593-596.

A "parent antibody" is an antibody comprising an amino acid sequence from which one or more amino acid residues are replaced by one or more cysteine residues. The parent antibody may comprise a native or wild type sequence. The parent antibody may have pre-existing amino acid sequence modifications (such as additions, deletions and/or substitutions) relative to other native, wild type, or modified forms of an antibody. A parent antibody is directed against a target antigen of interest. Antibodies directed against nonpolypeptide antigens (such as tumor-associated glycolipid antigens; see U.S. Pat. No. 5,091,178) are also contemplated.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In certain embodiments, the antibody will be purified (1) to greater than 95% by weight of antibody as determined by the Lowry method, or more than 99% by weight, (2) to a degree sufficient to obtain at least 15 residues of N-terminal or internal amino acid sequence by use of a gas phase protein sequencer, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

An antibody "which binds" a molecular target or an antigen of interest is one capable of binding that antigen with sufficient affinity such that the antibody is useful in targeting a cell expressing the antigen.

The terms "treat" or "treatment" refer to both therapeutic treatment and prophylactic or preventative measures, wherein the object is to prevent or slow down (lessen) an undesired physiological change or disorder, such as the development or spread of cancer. For purposes of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

"Phage display" is a technique by which variant polypeptides are displayed as fusion proteins to a coat protein on the surface of phage, e.g., filamentous phage, particles. One utility of phage display lies in the fact that large libraries of randomized protein variants can be rapidly and efficiently sorted for those sequences that bind to a target molecule with high affinity. Display of peptide and protein libraries on phage has been used for screening millions of polypeptides for ones with specific binding properties. Polyvalent phage display methods have been used for displaying small random peptides and small proteins, typically through fusions to either PIII or PVIII of filamentous phage. Wells and Lowman, Curr. Opin. Struct. Biol., 3:355-362 (1992), and references cited therein. In monovalent phage display, a protein or peptide library is fused to a phage coat protein or a portion thereof, and expressed at low levels in the presence of wild type protein. Avidity effects are reduced relative to polyvalent phage so that sorting is on the basis of intrinsic ligand affinity, and phagemid vectors are used, which simplify DNA manipulations. Lowman and Wells, Methods: A companion to Methods in Enzymology, 3:205-0216 (1991). Phage display includes techniques for producing antibody-like molecules (Janeway, C., Travers, P., Walport, M., Shlomchik (2001) Immunobiology, 5th Ed., Garland Publishing, New York, p 627-628).

A "phagemid" is a plasmid vector having a bacterial origin of replication, e.g., ColE1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle. The compounds described herein can be in the form of pharmaceutically or pharmaceutically acceptable salts. In some embodiments, such salts are derived from inorganic or organic acids or bases. For reviews of suitable salts, see, e.g., Berge et al., *J. Pharm. Sci.*, 1977, 66, 1-19 and *Remington: The Science and Practice of Pharmacy*, 20th Ed., A. Gennaro (ed.), Lippincott Williams & Wilkins (2000).

In the present disclosure, group "Ab" (i.e., the antibodies, antibody fragments, and/or antigen fragments) can be conjugated to more than one drug-containing moiety. In some embodiments, "Ab" can be conjugated to from 1 to 20 drug-containing moieties. In some embodiments, "Ab" can be conjugated to from 1 to 10 drug-containing moieties. In some embodiments, "Ab" can be conjugated to from 1 to 5 drug-containing moieties. In some embodiments, "Ab" can be conjugated to from 1 or 2 drug-containing moieties. In some embodiments, "Ab" can be conjugated to one drug-containing moiety.

In some aspects of the present disclosure, the ADC is combined with an antibody that binds PD-1 and/or an antibody that binds PDL-1.

The compounds described herein can be in the form of pharmaceutically or pharmaceutically acceptable salts. In some embodiments, such salts are derived from inorganic or organic acids or bases. For reviews of suitable salts, see, e.g., Berge et al., *J. Pharm. Sci.*, 1977, 66, 1-19 and *Remington: The Science and Practice of Pharmacy*, 20th Ed., A. Gennaro (ed.), Lippincott Williams & Wilkins (2000).

Examples of suitable acid addition salts include acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Examples of suitable base addition salts include ammonium salts; alkali metal salts, such as sodium and potassium salts; alkaline earth metal salts, such as calcium and magnesium salts; salts with organic bases, such as dicyclohexylamine salts, N-methyl-D-glucamine; and salts with amino acids such as arginine, lysine, and the like.

For example, Berge lists the following FDA-approved commercially marketed salts: anions acetate, besylate (benzenesulfonate), benzoate, bicarbonate, bitartrate, bromide, calcium edetate (ethylenediaminetetraacetate), camsylate (camphorsulfonate), carbonate, chloride, citrate, dihydrochloride, edetate (ethylenediaminetetraacetate), edisylate (1,2-ethanedisulfonate), estolate (lauryl sulfate), esylate (ethanesulfonate), fumarate, gluceptate (glucoheptonate), gluconate, glutamate, glycollylarsanilate (glycollamidophenylarsonate), hexylresorcinate, hydrabamine (N,N'-di(dehydroabietyl)ethylenediamine), hydrobromide, hydrochloride, hydroxynaphthoate, iodide, isethionate (2-hydroxyethanesulfonate), lactate, lactobionate, malate, maleate, mandelate, mesylate (methanesulfonate), methylbromide, methylnitrate, methylsulfate, mucate, napsylate (2-naphthalenesulfonate), nitrate, pamoate (embonate), pantothenate, phosphate/diphosphate, polygalacturonate, salicylate, stearate, subacetate, succinate, sulfate, tannate, tartrate, teoclate (8-chlorotheophyllinate) and triethiodide; organic cations benzathine (N,N'-dibenzylethylenediamine), chloroprocaine, choline, diethanolamine, ethylenediamine, meglumine (N-methylglucamine) and procaine; and metallic cations aluminum, calcium, lithium, magnesium, potassium, sodium and zinc.

Berge additionally lists the following non-FDA-approved commercially marketed (outside the United States) salts: anions adipate, alginate, aminosalicylate, anhydromethylenecitrate, arecoline, aspartate, bisulfate, butylbromide, camphorate, digluconate, dihydrobromide, disuccinate, glycerophosphate, hemisulfate, hydrofluoride, hydroiodide, methylenebis(salicylate), napadisylate (1,5-naphthalenedisulfonate), oxalate, pectinate, persulfate, phenylethylbarbiturate, picrate, propionate, thiocyanate, tosylate and undecanoate; organic cations benethamine (N-benzylphenethylamine), clemizole (1-p-chlorobenzyl-2-pyrrolildine-1'-ylmethylbenzimidazole), diethylamine, piperazine and tromethamine (tris(hydroxymethyl)aminomethane); and metallic cations barium and bismuth.

The compounds described herein may also comprise suitable carriers, excipients, and auxiliaries that may differ depending on the mode of administration.

In some embodiments, the pharmaceutical compositions can be formulated as a suitable parenteral dosage form. Said formulations can be prepared by various methods known in the art. The pharmaceutical compositions can be administered directly into the bloodstream, into muscle, or directly into an organ. Suitable means for parenteral administration include intravenous, intraarterial, intraperitoneal, intrathecal, intraventricular, intraurethral, intrasternal, intracranial, intramuscular, and subcutaneous. Suitable devices for parenteral administration include needle injectors, needle-free injectors, and infusion techniques.

Parenteral compositions are typically aqueous solutions which may contain excipients such as salts, carbohydrates and buffering agents. However, the composition may also be formulated a sterile non-aqueous solution or as a dried form to be used in conjunction with a suitable vehicle such as sterile pyrogen-free water.

The preparation of parenteral compositions under sterile conditions, for example, by lyophilization, can be readily accomplished using standard techniques known well to those of skill in the art.

Compositions for parenteral administration can be formulated to be immediate and/or modified release. Modified release formulations include delayed-, sustained-, pulsed-, controlled-, targeted, and programmed release. Thus, the compositions can be formulated as a solid, semi-solid, or thixotropic liquid for administration as an implanted depot providing modified release of the active agent.

The parenteral formulations can be admixed with other suitable pharmaceutically acceptable excipients used in parenteral dosage forms such as, but not limited to, preservatives.

In another embodiment, the pharmaceutical compositions can be formulated as suitable oral dosage forms such as tablets, capsules, powders, pellets, suspensions, solutions, emulsions, and the like. Other suitable carriers can be present such as disintegrants, diluents, chelating agents, binders, glidants, lubricants, fillers, bulking agents, anti-adherants, and the like.

Oral dosage formulations may also contain other suitable pharmaceutical excipients such as sweeteners, vehicle/wetting agents, coloring agents, flavoring agents, preservatives, viscosity enhancing/thickening agents, and the like.

The dose of the pharmaceutical compositions of the present disclosure can be tailored to the individual patient.

The term "radiation" refers to photon radiation or particle radiation. In some embodiments, the radiation can be photon radiation (x-rays and gamma rays). In such embodiments, the photons can be generated as a high energy photon beam from radioactive sources such as cobalt or a linear accelerator. In some embodiments, the radiation can be particle radiation (such as electrons, protons, neutrons, carbon ions, alpha particles, and beta particles). Particle radiation can be produced by linear accelerators. In some embodiments, the radiation can be an electron beam. In some embodiments, the radiation can be a proton beam. In some embodiments, the radiation can be a neutron beam.

In some embodiments, the radiation can be delivered by external beam radiation. In some embodiments, the external beam radiation can be three-dimensional conformal radiation therapy (3D-CRT). In some embodiments, the external beam radiation can be intensity modulated radiation therapy (IMRT). In some embodiments, the external beam radiation can be image-guided radiation therapy (IGRT). In some embodiments, the external beam radiation can be intensity modulated proton therapy (IMPT). In some embodiments, the external beam radiation can be stereotactic radiosurgery (SRS). In some embodiments, the external beam therapy can be fractionated stereotactic radiotherapy. In some embodiments, the external beam radiation can be stereotactic body radiation therapy (SBRT). Examples of machines that deliver SBRT are Gamma Knife®, X-Knife®, CyberKnife®, and Clinac®. In some embodiments, the radiation can be administered using a three dimensional conformal or stereotactic body radiation therapy delivery.

In some embodiments the radiation can be delivered by internal radiation therapy (brachytherapy). In such embodiments, the internal radiation therapy can be interstitial radiation, for example, using small pellets, seeds, wires or tubes placed close to the cancer or tumor site. In such embodiments, the internal radiation therapy can be intracavitary radiation, for example using a container of radioactive material that can be placed in a body cavity.

Method of Use of Compounds and Compositions

Certain compounds described herein are STING agonists and thus are useful in stimulating an immune response in subjects thereof. The compositions can be used in the treatment of cancer.

Compounds of the present disclosure show STING modulating/agonistic activity. Certain compounds of the present disclosure can be superior in terms of efficacy expression, pharmacokinetics (e.g., absorption, distribution, metabolism, excretion), solubility (e.g., water solubility), interaction with other medicaments (e.g., drug-metabolizing enzyme inhibitory action), safety (e.g., acute toxicity, chronic toxicity, genetic toxicity, reproductive toxicity, cardiotoxicity, carcinogenicity, central toxicity) and/or stability (e.g., chemical stability, stability to an enzyme), and can be useful as a medicament.

A compound of the present disclosure can be used for increasing STING activity in a mammal (e.g., mouse, rat, hamster, rabbit, cat, dog, cow, sheep, monkey, human).

A compound of the present disclosure can be used as a medicament such as an agent for the prophylaxis or treatment of diseases that can be influenced by STING (in the present specification, sometimes to be abbreviated as "STING-related diseases"), for example, cancers—e.g., colorectal cancers (e.g., colorectal cancer, rectal cancer, anus cancer, familial colorectal cancer, hereditary nonpolyposis colorectal cancer, gastrointestinal stromal tumor), lung cancers (e.g., non-small-cell lung cancer, small-cell lung cancer, malignant mesothelioma), mesothelioma, pancreatic cancers (e.g., pancreatic ductal carcinoma, pancreatic endocrine tumor), pharynx cancer, larynx cancer, esophageal cancer, stomach cancers (e.g., papillary adenocarcinoma, mucinous adenocarcinoma, adenosquamous carcinoma), duodenal cancer, small intestinal cancer, breast cancers (e.g., invasive ductal carcinoma, non-invasive ductal carcinoma, inflammatory breast cancer), ovarian cancers (e.g., ovarian epithelial cancer, extragonadal germ cell tumor, ovarian germ cell tumor, ovarian low-malignant potential tumor), testis tumor, prostate cancers (e.g., hormone-dependent prostate cancer, non-hormone dependent prostate cancer, castration-resistant prostate cancer), liver cancers (e.g., hepatocellular cancer, primary liver cancer, extrahepatic bile duct cancer), thyroid cancers (e.g., medullary thyroid carcinoma), renal cancers (e.g., renal cell cancers (e.g., clear cell renal cell cancer), transitional cell cancer of renal pelvis and ureter), uterine cancers (e.g., cervical cancer, uterine body cancer, uterus sarcoma), gestational choriocarcinoma, brain tumors (e.g., medulloblastoma, glioma, pineal astrocytic tumors, pilocytic astrocytoma, diffuse astrocytoma, anaplastic astrocytoma, pituitary adenoma), retinoblastoma, skin cancers (e.g., basalioma, malignant melanoma), sarcomas (e.g., rhabdomyosarcoma, leiomyosarcoma, soft tissue sarcoma, spindle cell sarcoma), malignant bone tumor, bladder cancer, blood cancers (e.g., multiple myeloma, leukemias (e.g., acute myelogenous leukemia), malignant lymphoma, Hodgkin's disease, chronic myeloproliferative disease), cancer of unknown primary; a cancer growth inhibitor; a cancer metastasis inhibitor; an apoptosis promoter; an agent for the treatment of precancerous lesions (e.g., myelodysplastic syndromes); and the like.

In certain embodiments, a compound of the present disclosure can be used as a medicament for colorectal cancer, breast cancer, skin cancer, malignant lymphoma or lung cancer.

In certain embodiments, a compound of the present disclosure can be used concurrently with an antibody therapy. In some embodiments, the antibody therapy comprises an anti-PD-1 antibody. In some embodiments, the antibody therapy comprises and anti-PD-L1 antibody.

In certain embodiments, a compound of the present disclosure can be used concurrently with an antibody therapy and radiation therapy. In some embodiments, the radiation therapy can be photon radiation therapy. In some embodiments, the radiation therapy can be particle radiation therapy.

Furthermore, a compound of the present disclosure can be used concurrently with a non-drug therapy. To be precise, a compound of the present disclosure or the combination agent of the present disclosure can be combined with a non-drug therapy such as (1) surgery, (2) hypertensive chemotherapy using angiotensin II etc., (3) gene therapy, (4) thermotherapy, (5) cryotherapy, (6) laser cauterization and (7) radiotherapy.

For example, by using a compound of the present disclosure before or after the above-mentioned surgery and the like, or before or after a combined treatment of two or three kinds thereof, effects such as prevention of emergence of resistance, prolongation of Disease-Free Survival, suppression of cancer metastasis or recurrence, prolongation of life and the like may be afforded.

In some embodiments, the present disclosure relates to a method of treating cancer in a patient by administering to a patient in need of said treating a combination of a compound of formula (I), or pharmaceutically acceptable salt thereof, and radiation.

In some embodiments, the present disclosure relates to a method of treating cancer in a patient by administering to a patient in need of said treating a combination of a compound of formula (I), or pharmaceutically acceptable salt thereof, one or more checkpoint inhibitors, and radiation. In some embodiments the one or more checkpoint inhibitors comprises an antibody. In some embodiments, the one or more checkpoint inhibitors comprises an anti-PD-1 antibody, In some embodiments, the one or more checkpoint inhibitors comprises an anti-PD-L1 antibody.

In some embodiments, the present disclosure relates to the use of a compound of formula (I), or a pharmaceutically acceptable salt thereof, in combination with a checkpoint inhibitor and radiation for the treatment of cancer in a patient.

In some embodiments, the present disclosure relates to a composition comprising a compound of formula (I), or a pharmaceutically acceptable salt thereof, for use in treating cancer in a patient, wherein the patient is also being treated with one or more checkpoint inhibitors and radiation. In some embodiments, the disclosure relates to a composition comprising a compound of formula (I), or a pharmaceutically acceptable salt thereof, for use in treating cancer in a patient, wherein the compound of formula (I), or the pharmaceutically acceptable salt thereof, is in combination with the one or more checkpoint inhibitors and radiation. In some embodiments, the compound of formula (I) can be administered simultaneously or sequentially with the checkpoint inhibitor, radiation, and/or combinations thereof. In some embodiments, the present disclosure relates to methods of treating cancer comprising administering to a patient in need of such treatment, a therapeutically effective amount of a combination of a compound of formula (I), one or more checkpoint inhibitors, and radiation.

In some embodiments, the radiation can be administered at least 5 hours before administration of the checkpoint inhibitor and/or the compound of formula (I). In some embodiments, the radiation can be administered at least 10 hours before administration of the checkpoint inhibitor and/or the compound of formula (I). In some embodiments, the radiation can be administered at least 20 hours before administration of the checkpoint inhibitor and/or the compound of formula (I). In some embodiments, the radiation can be administered at least 40 hours before administration of the checkpoint inhibitor and/or the compound of formula (I). In some embodiments, the radiation can be administered at least 80 hours before administration of the checkpoint inhibitor and/or the compound of formula (I).

In some embodiments, the radiation can be administered on each of days 1-5 of each week and repeated for 2 to 8 weeks. In some embodiments, the radiation can be administered on each of days 1-5 of each week and repeated for 6 to 8 weeks. In some embodiments, the radiation can be administered on each of days 1-5 of each week and repeated for 2 weeks. In some embodiments, the radiation can be administered on each of days 1-5 of each week and repeated for 3 weeks. In some embodiments, the radiation can be administered on each of days 1-5 of each week repeated and for 4 weeks. In some embodiments, the radiation can be administered on each of days 1-5 of each week and repeated for 5 weeks. In some embodiments, the radiation can be administered on each of days 1-5 of each week and repeated for 6 weeks. In some embodiments, the radiation can be administered on each of days 1-5 of each week and repeated for 7 weeks. In some embodiments, the radiation can be administered on each of days 1-5 of each week and repeated for 8 weeks.

In some embodiments, the radiation can be administered on any two of days 1-5 of each week and repeated for 5 to 8 weeks. In some embodiments, the radiation can be administered on any two of days 1-5 of each week and repeated for 6 to 8 weeks. In some embodiments, the radiation can be administered on any two of days 1-5 of each week and repeated for 5 weeks. In some embodiments, the radiation can be administered on any two of days 1-5 of each week and repeated for 6 weeks. In some embodiments, the radiation can be administered on any two of days 1-5 of each week and repeated for 7 weeks. In some embodiments, the radiation can be administered on any two of days 1-5 of each week and repeated for 8 weeks.

In some embodiments, the checkpoint inhibitor can be administered once every twelve weeks, once every four weeks, once every three weeks, once every two weeks, once every week, twice a week, three times a week, or daily. In some embodiments, the checkpoint inhibitor can be administered once every two weeks. In some embodiments, the checkpoint inhibitor can be administered once every three weeks. In some embodiments, the checkpoint inhibitor can be administered once every four weeks. In some embodiments, the checkpoint inhibitor can be administered once every twelve weeks.

In certain embodiments, the radiation is administered at least 40 hours before administration of the checkpoint inhibitor and/or the compound of formula (I). In certain embodiments, the radiation is administered at least 30 hours before administration of the checkpoint inhibitor and/or the compound of formula (I). In certain embodiments, the radiation is administered at least 20 hours before administration of the checkpoint inhibitor and/or the compound of formula (I). In certain embodiments, the radiation is administered at least 10 hours before administration of the checkpoint inhibitor and/or the compound of formula (I). In certain embodiments, the radiation is administered at least 5 hours before administration of the checkpoint inhibitor and/or the compound of formula (I). In certain embodiments, the radiation is administered at least 1 hour before administration of the checkpoint inhibitor and/or the compound of formula (I).

In some embodiments, the compound of formula (I) and/or the checkpoint inhibitor can be administered to the patient from 1 day to 3 months after the patient received treatment with radiation. In some embodiments, the compound of formula (I) and/or the checkpoint inhibitor can be administered to the patient from 1 day to 2 months after the patient received treatment with radiation. In some embodiments, the compound of formula (I) and/or the checkpoint inhibitor can be administered to the patient from 1 day to 1 month after the patient received treatment with radiation. In some embodiments, the compound of formula (I) and/or the checkpoint inhibitor can be administered to the patient from 1 day to 15 days after the patient received treatment with radiation. In some embodiments, the compound of formula (I) and/or the checkpoint inhibitor can be administered to the patient from 1 day to 7 days after the patient received treatment with radiation.

In some embodiments, the radiation can be administered at a fraction dose of about 1 Gy to about 100 Gy. In some embodiments, the radiation can be administered at a fraction dose of about 1 Gy to about 50 Gy. In some embodiments, the radiation can be administered at a fraction dose of about 1 Gy to about 20 Gy. In some embodiments, the radiation can be administered at a fraction dose of about 5 Gy to about 20 Gy. In some embodiments, the radiation can be administered at a fraction dose of about 6 Gy to about 18 Gy. In some embodiments, the radiation can be administered at a fraction dose of about 8 Gy to about 16 Gy. In some embodiments, the radiation can be administered at a fraction dose of about 5 Gy to about 10 Gy. In some embodiments, the radiation can be administered at a fraction dose of about 10 Gy to about 15 Gy. In some embodiments, the radiation can be administered at a fraction dose of about 15 Gy to about 20 Gy. In some embodiments, the radiation can be administered at a fraction dose of about 8 Gy or about 16 Gy.

In some embodiments, the radiation can be administered at a fraction dose of about 1 Gy. In some embodiments, the radiation can be administered at a fraction dose of about 2 Gy. In some embodiments, the radiation can be administered at a fraction dose of about 3 Gy. In some embodiments, the radiation can be administered at a fraction dose of about 4 Gy. In some embodiments, the radiation can be administered at a fraction dose of about 5 Gy. In some embodiments, the radiation can be administered at a fraction dose of about 6 Gy. In some embodiments, the radiation can be administered at a fraction dose of about 7 Gy. In some embodiments, the radiation can be administered at a fraction dose of about 8 Gy. In some embodiments, the radiation can be administered at a fraction dose of about 9 Gy. In some embodiments, the radiation can be administered at a fraction dose of about 10 Gy. In some embodiments, the radiation can be administered at a fraction dose of about 11 Gy. In some embodiments, the radiation can be administered at a fraction dose of about 12 Gy. In some embodiments, the radiation can be administered at a fraction dose of about 13 Gy. In some embodiments, the radiation can be administered at a fraction dose of about 14 Gy. In some embodiments, the radiation can be administered at a fraction dose of about 15 Gy. In some embodiments, the radiation can be administered at a fraction dose of about 16 Gy. In some embodiments, the radiation can be administered at a fraction dose of about 17 Gy. In some embodiments, the radiation can be administered at a fraction dose of about 18 Gy. In some embodiments, the radiation can be administered at a fraction dose of about 19 Gy. In some embodiments, the radiation can be administered at a fraction dose of about 20 Gy In some embodiments, the radiation can be administered in fractions. In some embodiments, the radiation can be administered in from 1 to 10 fractions. In some embodiments, the radiation can be administered in from 1 to 5 fractions. In some embodiments, the radiation can be administered in 1 fraction, or in 2 fractions, or in 3 fractions, or in 4 fractions, or in 5 fractions. In some embodiments, the radiation can be administered in 1 fraction or in 3 fractions.

In some embodiments, the radiation can be administered at a fraction dose of about 1-5 Gy for 1-3 fractions. In some embodiments, the radiation can be administered at a fraction dose of about 5-10 Gy for 1-3 fractions. In some embodiments, the radiation can be administered at a fraction dose of about 10-15 Gy for 1-3 fractions. In some embodiments, the radiation can be administered at a fraction dose of about 15-20 Gy for 1-3 fractions. In some embodiments, the radiation can be administered at a fraction dose of about 5-10 Gy for 1-3 fractions or 15-20 Gy for 1-3 fractions. In some embodiments, the radiation can be administered at a fraction dose of about 8 Gy for 1 fraction. In some embodiments, the radiation can be administered at a fraction dose of about 8 Gy for 3 fraction. In some embodiments, the radiation can be administered at a fraction dose of about 16 Gy for 1 fraction. In some embodiments, the radiation can be administered at a fraction dose of about 8 Gy for 1 fraction, or about 8 Gy for 3 fractions, or about 16 Gy for 1 fraction.

In addition, it is possible to combine a treatment with a compound of the present disclosure or the combination agent of the present disclosure with a supportive therapy: (i) administration of antibiotic (e.g., β-lactam type such as pansporin and the like, macrolide type such as clarithromycin and the like) for the complication with various infectious diseases, (ii) administration of high-calorie transfusion, amino acid preparation or general vitamin preparation for the improvement of malnutrition, (iii) administration of morphine for pain mitigation, (iv) administration of a pharmaceutical agent for ameliorating side effects such as nausea, vomiting, anorexia, diarrhea, leucopenia, thrombocytopenia, decreased hemoglobin concentration, hair loss, hepatopathy, renopathy, DIC, fever and the like and (v) administration of a pharmaceutical agent for suppressing multiple drug resistance of cancer and the like.

EXAMPLES

Definitions

Ab antibody
ACN acetonitrile
ADA anti-drug antibody
ADC antibody drug conjugate
BLQ below limit of quantitation
C Celsius
CCR2 C-C motif chemokine receptor 2
CR complete response
CD cluster of differentiation
DAR drug antibody ratio
DMA N,N-dimethylacetamide
DMSO dimethylsulfoxide
DTT dithiothreitol
ε extinction coefficient
E 0.1% 0.1% solution extinction coefficient
$EC_{50}$ half maximum effective concentration
EDTA ethylenediaminetetraacetic acid
h hours
HIC hydrophobic interaction chromatography
hIgG human immunoglobulin G
HPLC high pressure liquid chromatography
IACUC Institutional Animal Care and Use Committee
IFN interferon
IgG immunoglobulin G
IgM immunoglobulin M
IL interleukin
IP interferon gamma-induced protein
LC liquid chromatography
LCMS liquid chromatography mass spectrometry
μM micromolar
MCP monocyte chemoattractant protein
MDSC myeloid derived suppressor cells
mL milliliters
MS mass spectrum
MTD maximum tolerated dose
NA not available
OAc acetate
PBS phosphate buffered saline
PEG polyethyleneglycol
QTOF quadrupole time-of-flight
rt room temperature
SEC size exclusion chromatography
STING stimulator of interferon genes
TCEP (tris(2-carboxyethyl)phosphine)
TNF tumor necrosis factor
TPPTS 3,3',3"-phosphanetriyltris(benzenesulfonic acid) trisodium salt
Tris tris(hydroxymethyl)aminomethane
UFLC ultra fast liquid chromatograph
UV ultraviolet
Analytical Methods
Analytical SEC Conditions:
SEC spectra were recorded on a Hewlett-Packard HP1100 or an Agilent 1100 Series LC system with Diode Array Detector using a SEC column (typically Tosoh Biosep TSK Gel, G3000SWx1; P/N 8541; 250A; 5 um; 7.8 mm×300 mm) at 280 nm. Mobile phase was 100 mM sodium phosphate, 300 mM sodium chloride, pH 6.8, 10% acetonitrile (v/v) or 1×PBS. A typical run is isocratic at a flow rate of 1 mL/min for 20 min.

Analytical HIC Conditions:

HIC spectra were recorded on a Hewlett-Packard HP1100 or Agilent 1100 Series LC system with Diode Array Detector using a HIC column (typically Tosoh Butyl-NPR, 4.6×35 mm, 2.5 um, P/N: 14947) at 280 nm. Mobile phase A was 25 mM sodium phosphate, 1.5 M ammonium sulfate, pH 7, and Mobile phase B was 75% 25 mM sodium phosphate, pH 7, 25% isopropanol. For a typical 20 min run, a 12 min linear gradient from 95%/5% A/B to 100% B would be used between initial and final intervals of isocratic flow.

LC-QTOF Conditions:

LCMS spectra were recorded on an Agilent 1260 Bioinert Series LC system connected to an Agilent 6545 QTOF mass spectrometer using a reverse phase column heated to 80° C. (typically Agilent, PLRP-S, 5 μm, 1000 Å, 2.1 mm×50 mm). Various gradients and run times were selected in order to best characterize the compounds. Mobile phases were based on ACN/water gradients and contained 0.1% formic acid. One example of a solvent gradient that was used was 95% mobile phase A (mobile phase A=99% water+1% ACN+ 0.1% formic acid) to 100% mobile phase B (mobile phase B=95% ACN+5% water+0.1% formic acid) with conditions shown in Table 1.

TABLE 1

| Time (min) | Flow (mL/min) | % A | % B |
| --- | --- | --- | --- |
| 0 | 0.35 | 82 | 18 |
| 1 | 0.35 | 82 | 18 |
| 2 | 0.35 | 70 | 30 |
| 19 | 0.5 | 50 | 50 |
| 19.5 | 0.5 | 10 | 90 |
| 21 | 0.5 | 10 | 90 |
| 21.1 | 0.5 | 82 | 18 |
| 22 | 0.5 | 82 | 18 |

Samples were either intact or reduced (20 uL of 1-5 mg/mL ADC solution treated with 4 uL of 0.5M DTT solution at 37° C. for 30 min). Raw data was deconvoluted within appropriate mass range using Agilent BioConfirm software to obtain protein molecular weight(s), and the Agilent DAR Calculator was used to calculate DAR.

LC/MS/MS Conditions:

LC/MS/MS analysis was performed using Shimadzu UFLC LC-20AD XR binary pump and SIL-30AC MP autosampler system and AB SCIEX Triple Quad 4500 ESI Mass spectrometry.

Typically, 5 uL sample aliquots were injected into the LC/MS/MS after passing through a Waters Xselect C18 CSH 3.5 u 2.1 mm ID×30 mm column. Mobile phase A contained 0.1% formic acid in water, and mobile phase B contained 0.1% formic acid in 5% water with 95% acetonitrile. Total run time was 3 min at 1.5 mL/min with a linear gradient from 100% A to 100% B over 1.5 min flow rate. Initially, the instrument was running at 100% aqueous mobile phase solvent for 0.5 min, and then it was increased to 100% organic solvent in next 1.5 min.

Preparative SEC:

Preparative SEC purification was conducted on a Gilson Preparative HPLC system with UV Detector using a SEC column (typically GE Superdex 200 Increase 10/300 GL).

Mobile phase was 1×PBS (pH 7.4). A typical run was isocratic at a flow rate of 1 mL/min for 30 min. Fraction collection was triggered based on UV threshold (at 214 and 280 nm).

ADC Concentration:

ADC concentration was calculated from the UV absorbance at 280 nm measured by NanoDrop (2000c; Fisher Scientific) coefficient after subtraction of the UV absorbance from the corresponding linker-payload constructs.

Table 2 lists linker-payload constructs that were used for ADC preparations. The compounds contain either Compound No. 14 (described in WO2018/100558A2) or Compound I-5c (described in WO2019/092660) as a payload. The syntheses of the linker-payload constructs were described in PCT Application PCT/IB2020/054400.

TABLE 2

| Linker-Payload Construct | Structure |
|---|---|
| C-2 | 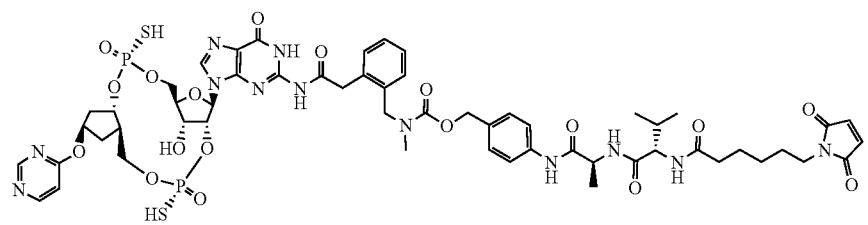 |
| C-3 | 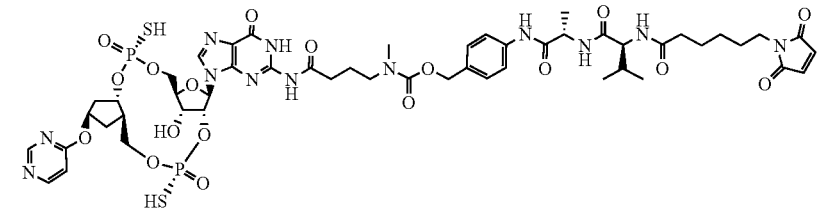 |
| C-4 | 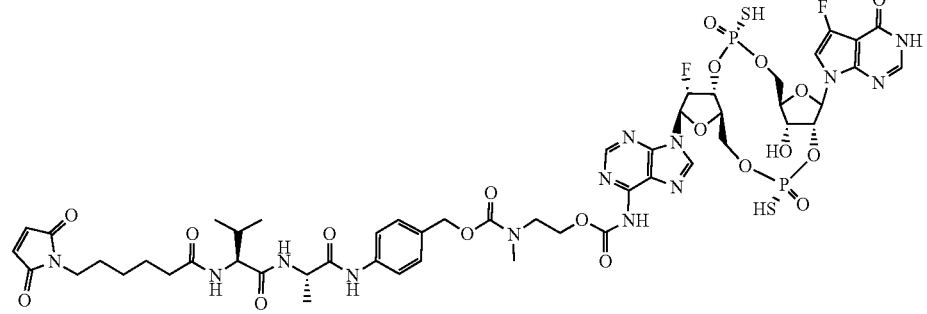 |
| C-5 | 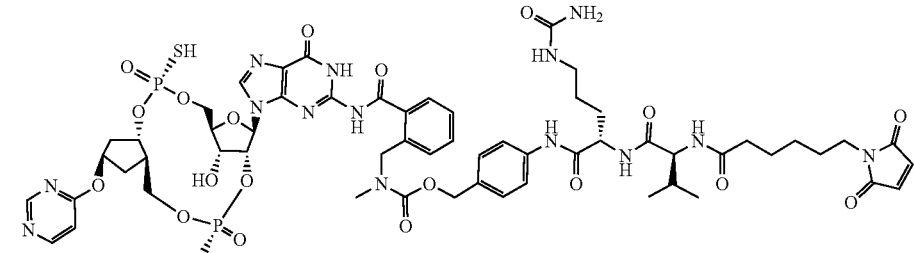 |
| C-8 | 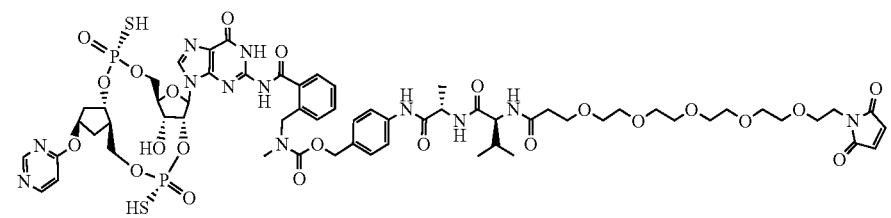 |

TABLE 2-continued
| Linker-Payload Construct | Structure |
|---|---|
| C-9 | 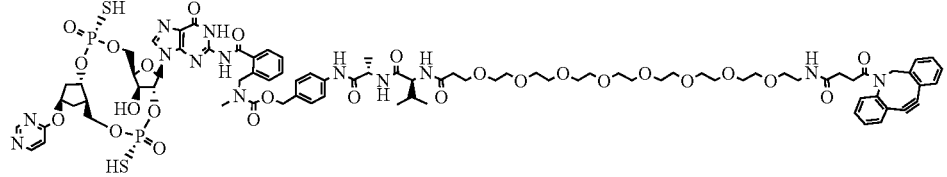 |
| C-10 | 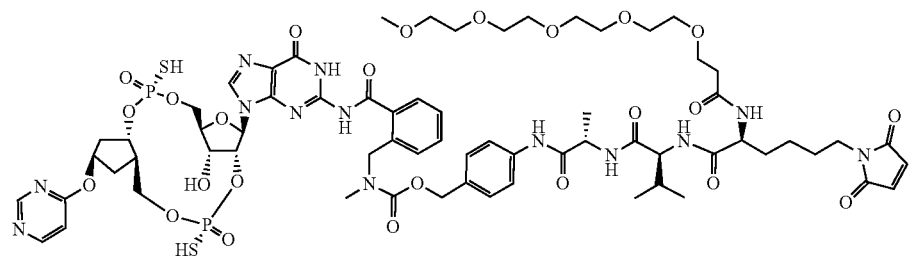 |
| C-13 | 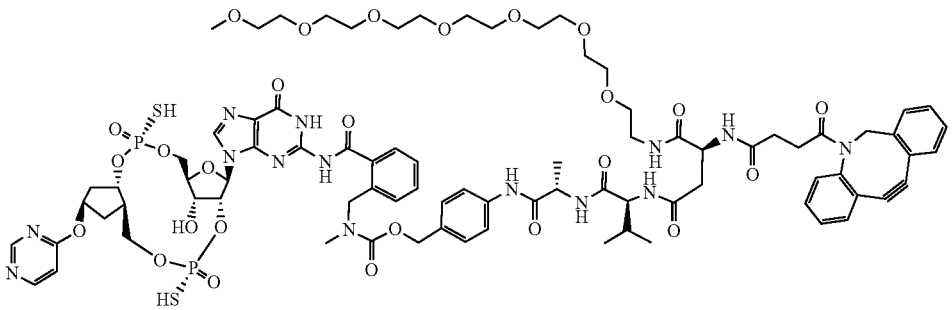 |
| C-15 | 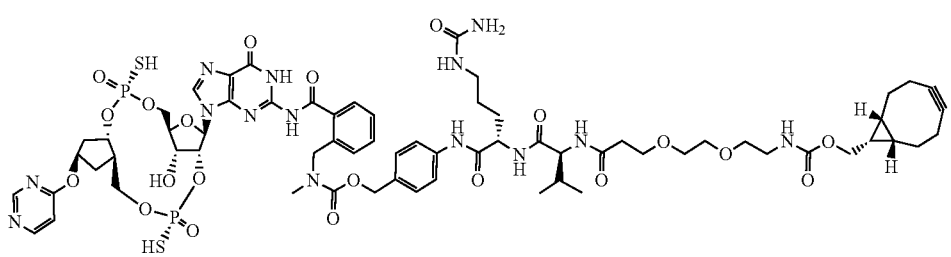 |
| C-18 | 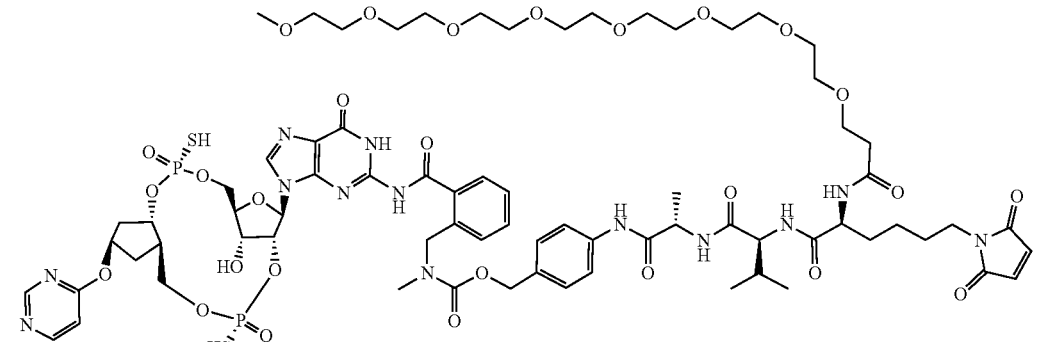 |

TABLE 2-continued

| Linker-Payload Construct | Structure |
|---|---|
| C-20 | 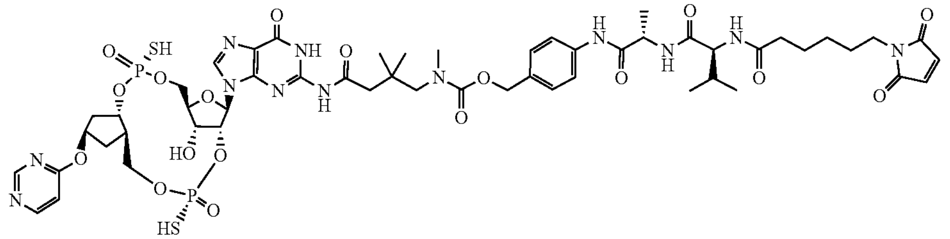 |
| C-21 | 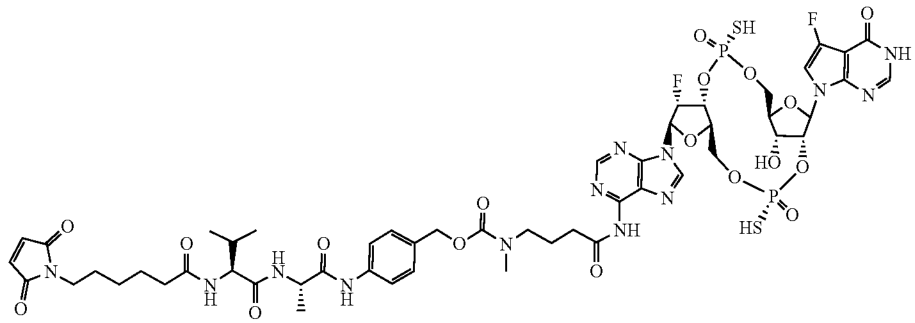 [SMILES: CC(C)[C@H](NC(=O)CCCCCN1C(=O)C=CC1=O)C(=O)N[C@@H](C)C(=O)Nc1ccc(COC(=O)N(C)CCCC(=O)Nc2ncnc3c2ncn3[C@@H]2O[C@@H]3CO[P@@](=O)(S)O[C@H]4C(n5cc(F)c6c(=O)[nH]cnc65)O[C@H](CO[P@@](=O)(S)O[C@H]3[C@H]2F)[C@H]4O)cc1] |
| C-22 | 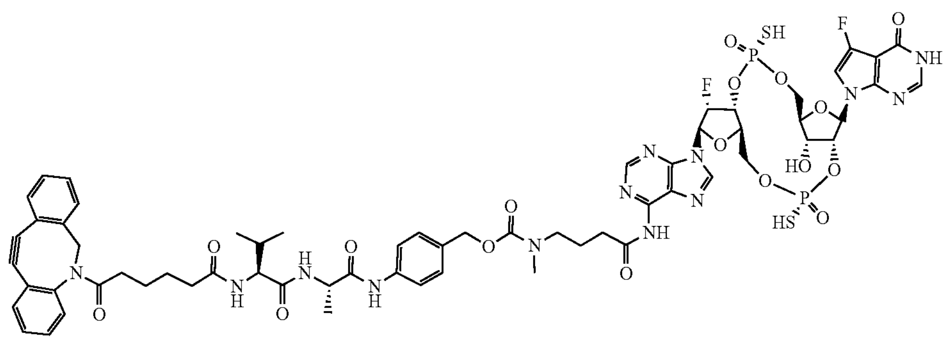 |
| C-30 | 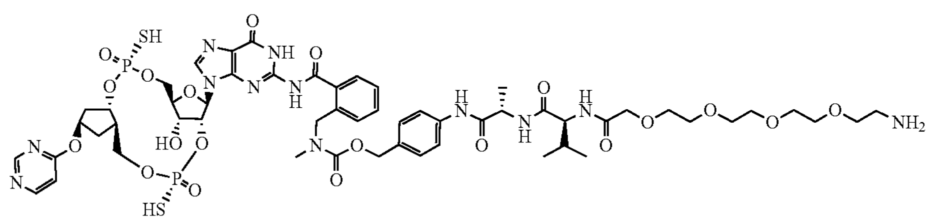 |
| C-38 | 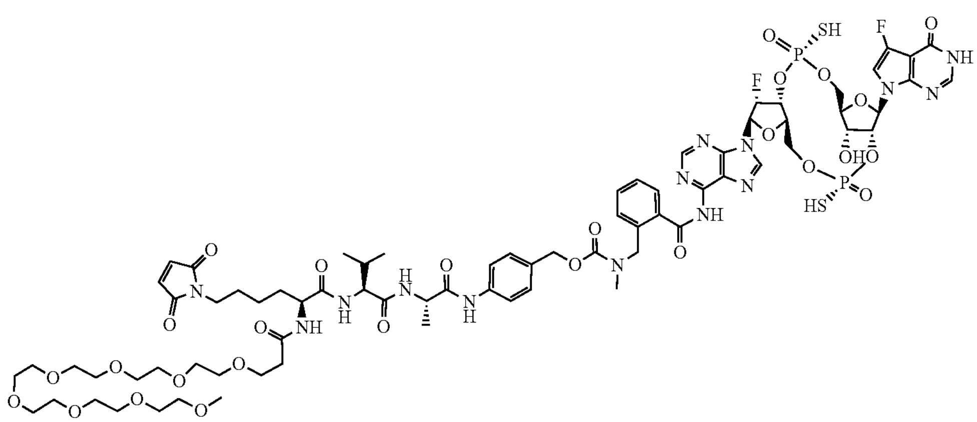 [SMILES: COCCOCCOCCOCCOCCOCCOCCOCCC(=O)N[C@@H](CCCCN1C(=O)C=CC1=O)C(=O)N[C@H](C(=O)N[C@@H](C)C(=O)Nc1ccc(COC(=O)N(C)Cc2ccccc2C(=O)Nc2ncnc3c2ncn3[C@@H]2O[C@@H]3CO[P@@](=O)(S)O[C@@H]4[C@H](O)[C@@H](CO[P@@](=O)(S)O[C@H]3[C@H]2F)O[C@H]4n2cc(F)c3c(=O)[nH]cnc32)cc1)C(C)C] |

TABLE 2-continued

| Linker-Payload Construct | Structure |
|---|---|
| C-39 | (chemical structure) |
| C-41 | (chemical structure) |

The anti-human CCR2 monoclonal antibody composed of the humanized variable domains of the heavy and the light chains of the 1D9 mouse monoclonal antibody and the constant domains of human IgG1 heavy chain and human kappa light chain (humanized 1D9, also called TAK-202, may also be referred to as the hIgG1 isotype hereunder) was generated as described in U.S. Pat. No. 7,473,421 B2. The hIgG4 isotype of humanized 1D9 was prepared in a manner similar to the method described in Anticancer Research March-April 2006 vol. 26 no. 2A 1057-1063.

```
Sequence of humanized 1D9
Heavy chain:
                                         (SEQ ID NO: 3)
EVQLVESGGG LVKPGGSLRL SCAASGFTFS AYAMNWVRQA

PGKGLEWVGR IRTKNNNYAT YYADSVKDRF TISRDDSKNT

LYLQMNSLKT EDTAVYYCTT FYGNGVWGQG TLVTVSSAST

KGPSVFPLAP SSKSTSGGTA ALGCLVKDYF PEPVTVSWNS

GALTSGVHTF PAVLQSSGLY SLSSVVTVPS SSLGTQTYIC

NVNHKPSNTK VDKKVEPKSC DKTHTCPPCP APELAGAPSV

FLFPPKPKDT LMISRTPEVT CVVVDVSHED PEVKFNWYVD

GVEVHNAKTK PREEQYNSTY RVVSVLTVLH QDWLNGKEYK

CKVSNKALPA PIEKTISKAK GQPREPQVYT LPPSRDELTK

NQVSLTCLVK GFYPSDIAVE WESNGQPENN YKTTPPVLDS

DGSFFLYSKL TVDKSRWQQG NVFSCSVMHE ALHNHYTQKS

LSLSPGK
```

```
Light chain:
                                         (SEQ ID NO: 4)
DVVMTQSPLS LPVTLGQPAS ISCKSSQSLL DSDGKTFLNW

FQQRPGQSPR RLIYLVSKLD SGVPDRFSGS GSGTDFTLKI

SRVEAEDVGV YYCWQGTHFP YTFGQGTRLE IKRTVAAPSV

FIFPPSDEQL KSGTASVVCL LNNFYPREAK VQWKVDNALQ

SGNSQESVTE QDSKDSTYSL SSTLTLSKAD YEKHKVYACE

VTHQGLSSPV TKSFNRGEC
```

```
Sequence of humanized 1D9 hIgG4 isotype
Heavy chain:
                                         (SEQ ID NO: 5)
EVQLVESGGGLVKPGGSLRLSCAASGFTFSAYAMNWVRQAPGKGLEWVGR

IRTKNNNYATYYADSVKDRFTISRDDSKNTLYLQMNSLKTEDTAVYYCTT

FYGNGVWGQGTLVTVSSASTKGPSVFPLAPCSRSTSESTAALGCLVKDYF

PEPVTVSWNSGALTSGVHTFPAVLQSSGLYSLSSVVTVPSSSLGTKTYTC

NVDHKPSNTKVDKRVESKYGPPCPPCPAPEFLGGPSVFLFPPKPKDTLMI

SRTPEVTCVVVDVSQEDPEVQFNWYVDGVEVHNAKTKPREEQFNSTYRVV

SVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGS

FFLYSRLTVDKSRWQEGNVFSCSVMHEALHNHYTQKSLSLSLG
```

```
Light chain:
                                         (SEQ ID NO: 6)
DVVMTQSPLSLPVTLGQPASISCKSSQSLLDSDGKTFLNWFQQRPGQSPR

RLIYLVSKLDSGVPDRFSGSGSGTDFTLKISRVEAEDVGVYYCWQGTHFP
```

```
YTFGQGTRLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC
```

Example 1

Procedure for Preparation of Ab-STING Agonist Conjugates Via Stochastic Cysteine Conjugation To a solution of an anti-CCR2 antibody (humanized 1D9, 10 mg/mL) in 50 mM histidine, 125 mM arginine, and pH 6.1 buffer was added TCEP (1 mM solution in $H_2O$, 2-3 equiv.). The reaction mixture was purged with argon and incubated at rt or 37° C. for 1-3 h with gentle shaking. The desired linker-payload construct (5 mM solution in DMA, 6-9 equiv.) was then added slowly into the above mixture. The reaction was purged with argon and incubated at rt or ° C. for another 1-2 h with gentle shaking. The reaction mixture was purified following the preparative SEC method described herein to give the ADC. The ADC concentration, percentage aggregation, and DAR were determined by UV absorbance, analytical SEC, and LC-QTOF respectively, as described in analytical methods.

A schematic of this procedure is shown in FIG. 1

An analogous procedure to described above was used to prepare other antibody conjugates.

Example 2

Preparation of Additional Ab-STING Agonist Conjugates Via Stochastic Cysteine Conjugation The antibody drug conjugates listed in Table 3 were prepared as described in Example 1, using the linker-payload constructs and antibody shown as the starting materials.

TABLE 3

| ADC product | Linker-payload | humanized 1D9 isotype | Payload | DAR | Aggregation % | Yield % |
|---|---|---|---|---|---|---|
| ADC-B1 | C-3 | hIgG4 | Compound I-5c | 3.7 | BLQ | 75 |
| ADC-B2 | C-21 | hIgG4 | Compound No. 14 | 4.3 | BLQ | 80 |
| ADC-B3 | C-20 | hIgG4 | Compound I-5c | 2.4 | BLQ | 40 |
| ADC-B5 | C-4 | hIgG4 | Compound No. 14 | 3.4 | BLQ | 100 |
| ADC-B6 | C-5 | hIgG4 | Compound I-5c | 3.1 | BLQ | 56 |
| ADC-B7 | C-2 | hIgG4 | Compound I-5c | 3.2 | BLQ | 92 |
| ADC-B8 | C-10 | hIgG4 | Compound I-5c | 3.9 | BLQ | 50 |
| ADC-B13 | C-8 | hIgG4 | Compound I-5c | 3.9 | BLQ | 44 |
| ADC-B14 | C-18 | hIgG1 | Compound I-5c | 4.0 | BLQ | 74 |
| ADC-B16 | C-41 | hIgG1 | Compound I-5c | 4.1 | BLQ | 51 |
| ADC-B17 | C-38 | hIgG1 | Compound No. 14 | 3.8 | BLQ | 74 |

Example 3

Procedure for Preparation of Ab-STING Agonist Conjugates Via Transglutaminase Conjugation Deglycosylation: A solution of anti-CCR2 antibody (humanized 1D9, generated as described in U.S. Pat. No. 7,473,421 B2, 60 mg/mL) in 50 mM histidine, 125 mM arginine, pH 6.1 buffer was diluted with an equal volume of pH 7.2 PBS. To the solution was added N-Glycosydase F (New England Biolabs, P0704S, 500,000 units/mL, 300 units per 1 mg of antibody) and the reaction mixture was heated to 37° C. with gentle mixing overnight. The resulting deglycosylated humanized 1D9 was buffer-exchanged with PBS pH 7.2.

Transglutaminase conjugation: To the deglycosylated humanized 1D9 solution (10-20 mg/mL) in PBS prepared above was added a 0.1 M DMSO solution of amine-PEG-azide (40 equivalents) followed by transglutaminase (AC-TIVA™, Ajinomoto, 5-10 mg per 1 mg of antibody). The reaction mixture was heated to 37° C. with gentle mixing overnight. The product was purified following the preparative SEC method described herein to give humanized 1D9-NH-PEG-azide.

Strain-promoted azide-alkyne cycloaddition: To a solution of humanized 1D9-NH-PEG-azide conjugate prepared above (2~15 mg/mL in PBS) was added a 4~10 mM DMSO solution of the strained-alkyne containing linker-payload constructs (3-5 equivalents in which DMSO <10% of the total solvent volume). The resulting solution was gently stirred at rt overnight. The product was purified following the preparative SEC method described herein to give the ADC. The ADC concentration, percentage aggregation, and DAR were determined by UV absorbance, analytical SEC, and LC-QTOF respectively, as described in analytical methods.

Figure 2:
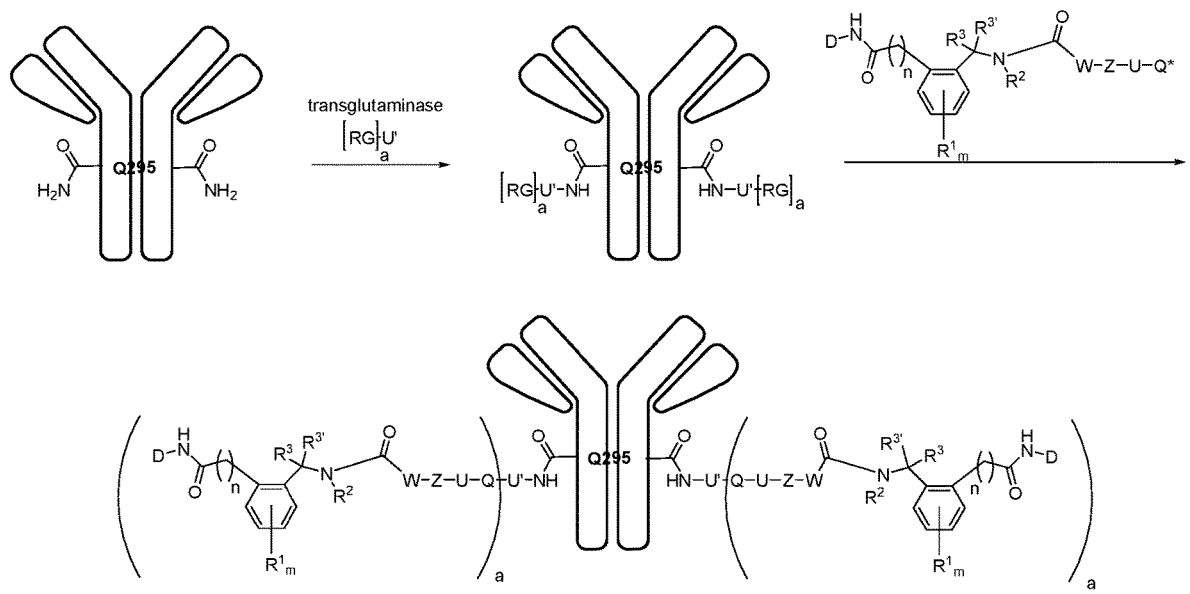
FIG. 2 depicts the preparation of Ab-STING agonist conjugates via transglutaminase conjugation.

A schematic of this procedure is shown in FIG. 2 (RG=$N_3$). An analogous procedure to described above was used to prepare other antibody conjugates.

Example 4

Preparation of Ab-STING Agonist Conjugates Via Transglutaminase Conjugation

The antibody drug conjugates listed in Table 4 were prepared as described in Example 3, using the starting linker-payload constructs shown as the starting material in the table.

TABLE 4

| ADC product | Linker-payload | humanized 1D9 isotype | PEG length | Payload | DAR | Aggregation % | Yield % |
|---|---|---|---|---|---|---|---|
| ADC-B4 | C-22 | hIgG4 | 2 | Compound No. 14 | 1.8 | BLQ | 70 |
| ADC-B9 | C-15 | hIgG4 | 35 | Compound I-5c | 2.0 | BLQ | 42 |
| ADC-B10 | C-15 | hIgG4 | 23 | Compound I-5c | 2.1 | BLQ | 70 |
| ADC-B11 | C-13 | hIgG4 | 23 | Compound I-5c | 2.0 | BLQ | 80 |
| ADC-B12 | C-9 | hIgG4 | 9 | Compound I-5c | 1.7 | BLQ | 50 |

Example 5

Procedure for Preparation of Ab-STING Agonist Conjugates Via Transglutaminase Conjugation Transglutaminase conjugation (following the procedure described in Tumey, L. N. et al. *Mol. Pharmaceutics* 2019, 16, 6, 2795-2807 after modification): To a solution of transglutaminase (ACTIVA™, Ajinomoto, 50 mg per 1 mg of antibody) in pH 6.1 phosphate buffer was added the deglycosylated humanized 1D9 solution (10-20 mg/mL, prepared following the deglycosylation procedure described in Example 3) in PBS, followed by a 30 mM cystamine·2HCl (50 equivalents) solution in pH 6.1 phosphate buffer. The reaction mixture was heated to 37° C. with gentle mixing overnight. The product was purified using HiTrap Protein A HP column (GE Healthcare, 17-0402-01), by first washing with 20 mM phosphate pH 7.0 and then eluting ADCs with 0.1M citric acid pH 4.0. Further purification on the preparative SEC method described herein to give humanized 1D9-NH—$(CH_2)_2$—S—S—$(CH_2)_2$—$NH_2$.

Maleimide addition: To a solution of humanized 1D9-NH—$(CH_2)_2$—S—S—$(CH_2)_2$—$NH_2$ conjugate prepared above (2~15 mg/mL in 20 mM pH 5 NaOAc buffer) was added a 5 mM TPPTS solution in water (5 equivalents) at 0° C. The resulting solution was incubated at 0° C. overnight. After removing small molecule by dialysis the solution was incubated for another 24 h at 0° C. The desired linker-payload construct (5 mM solution in DMA, 2.05 equiv.) was then added slowly into the above mixture. The reaction was incubated at 0° C. for 1.5-2 h with gentle shaking. The reaction mixture was purified following the preparative SEC method described herein to give the ADC. The ADC concentration, percentage aggregation, and DAR were determined by UV absorbance, analytical SEC, and LC-QTOF respectively, as described in analytical methods.

A schematic of this procedure is depicted in FIG. 2 (RG=SH). An analogous procedure to described above was used to prepare other antibody conjugates.

Example 6

Preparation of Ab-STING Agonist Conjugates Via Transglutaminase Conjugation

The antibody drug conjugates listed in Table 5 were prepared as described in Example 5, using the starting linker-payload construct shown as the starting material in the table.

TABLE 5

| ADC product | Linker-payload | humanized 1D9 isotype | Payload | DAR | Aggregation % | Yield % |
|---|---|---|---|---|---|---|
| ADC-B18 | C-18 | hIgG1 | Compound I-5c | 2.0 | BLQ | 80 |
| ADC-B19 | C-39 | hIgG1 | Compound I-5c | 2.0 | BLQ | 89 |
| ADC-B20 | C-38 | hIgG1 | Compound No. 14 | 1.9 | BLQ | 80 |

Example 7

Preparation of Ab-STING Agonist Conjugates Via Transglutaminase Conjugation

To the deglycosylated humanized 1D9 solution (10~20 mg/mL, prepared following the deglycosylation procedure described in Example 3) in PBS was added 1M Tris, 5M NaCl, pH 8.0 buffer (10~20% of the total volume) to adjust pH to 8.0. To the solution was added 10 mM DMSO solution of primary amine-containing linker-payload constructs (20 equiv) followed by transglutaminase (ACTIVA™, Ajinomoto, 100-150 mg per 1 mg of antibody). The reaction mixture was heated to 37° C. with gentle mixing overnight. The product was purified using HiTrap Protein A HP column (GE Healthcare, 17-0402-01), by first washing with 20 mM phosphate pH 7.0 and then eluting ADCs with 0.1M citric acid pH 4.0. The product was further purified following the preparative SEC method described herein to give the ADC. The ADC concentration, percentage aggregation, and DAR were determined by UV absorbance, analytical SEC, and LC-QTOF respectively, as described in analytical methods.

Figure 3:
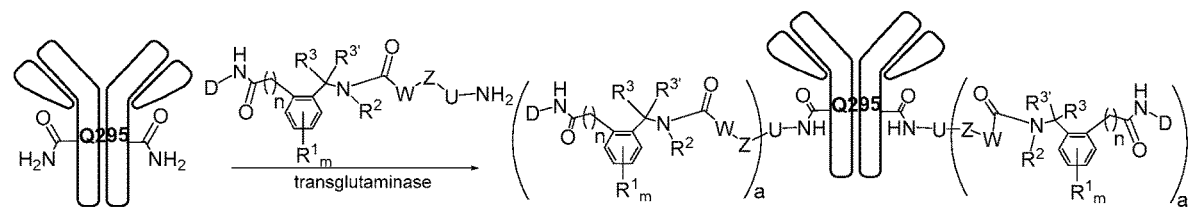
FIG. 3 depicts the preparation of Ab-STING agonist conjugates via transglutaminase conjugation.
Figure 4:
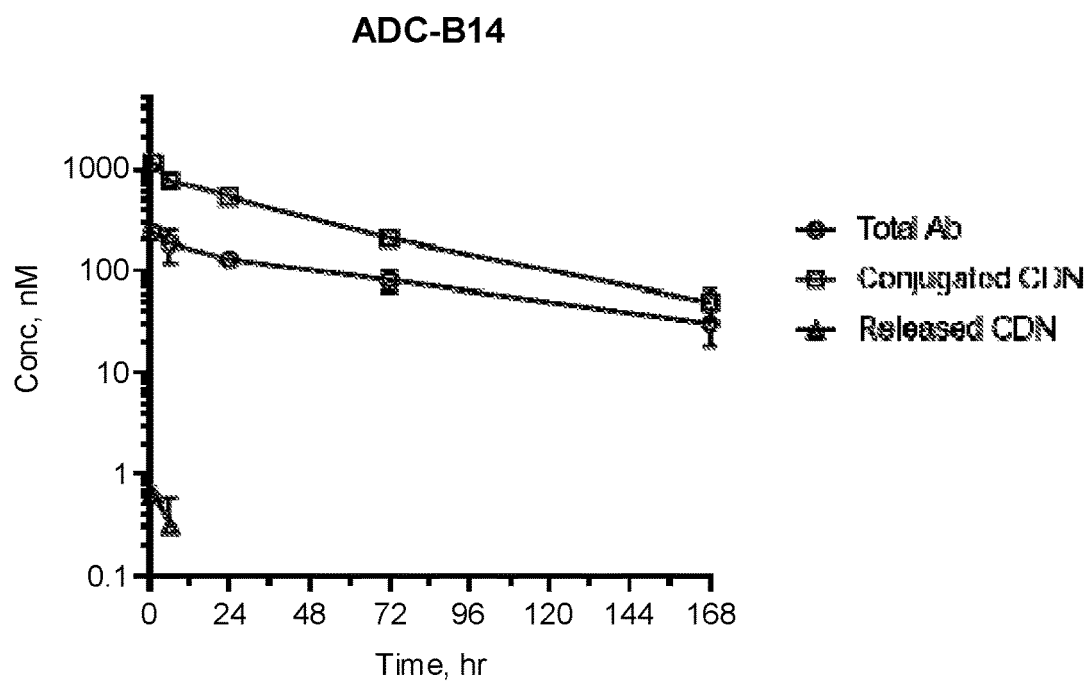
FIG. 4 depicts the mouse PK profile of Antibody Drug Conjugate B-14.
Figure 5:
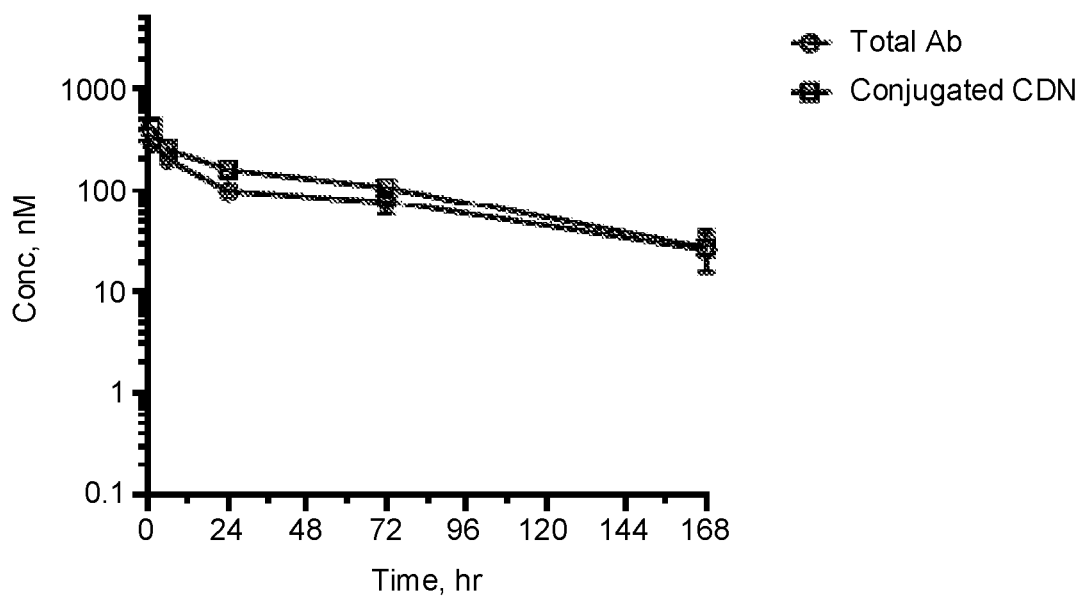
FIG. 5 depicts the mouse PK profile of Antibody Drug Conjugate B-15.
Figure 6:
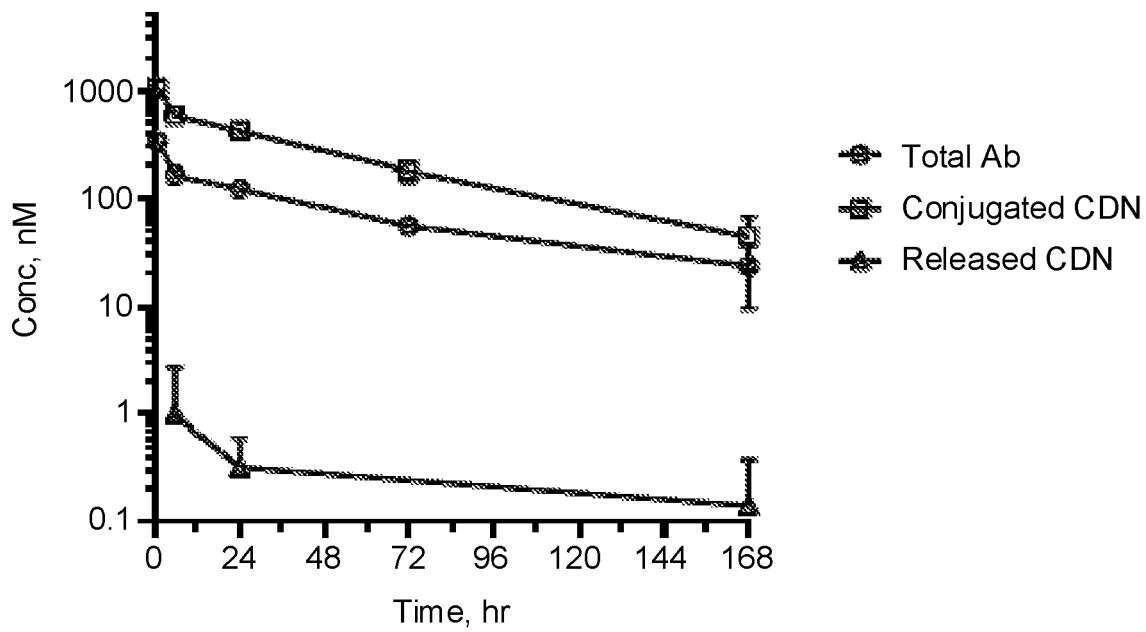
FIG. 6 depicts the mouse PK profile of Antibody Drug Conjugate B-16.
Figure 7:
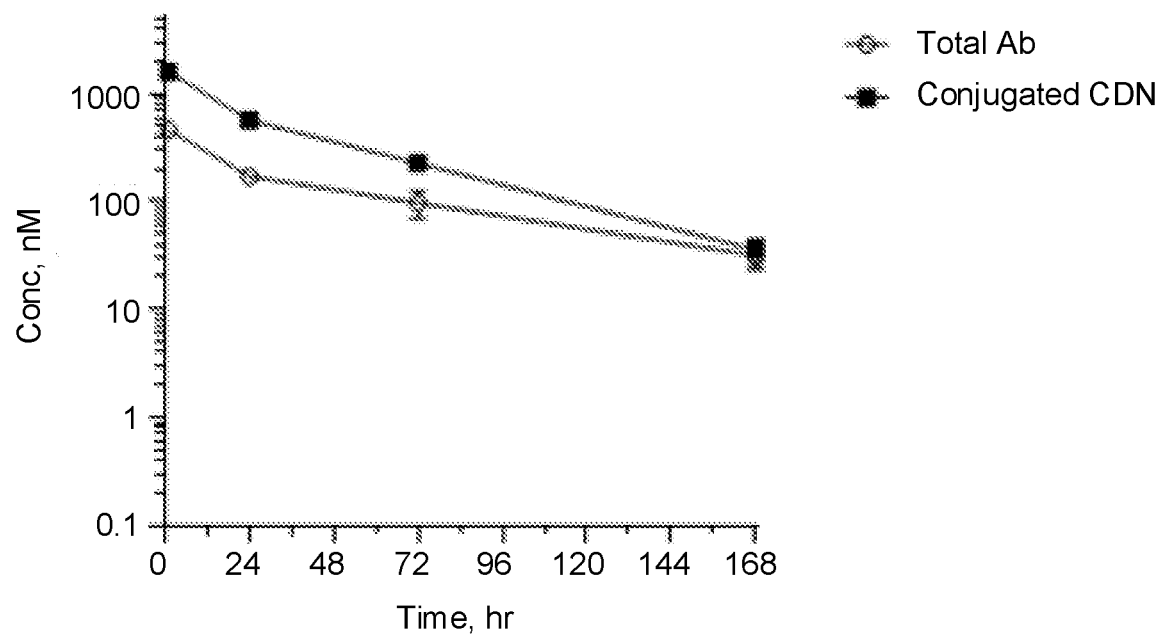
FIG. 7 depicts the mouse PK profile of Antibody Drug Conjugate B-17.
Figure 8:
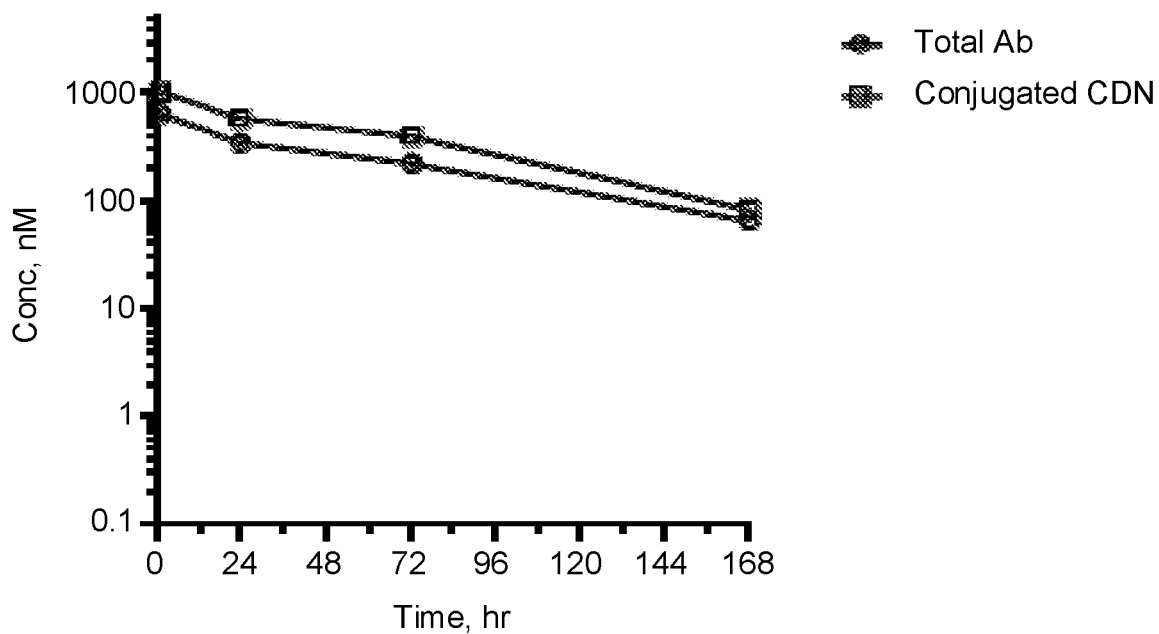
FIG. 8 depicts the mouse PK profile of Antibody Drug Conjugate B-18.

A schematic of the procedure is depicted in FIG. 3. An analogous procedure to described above was used to prepare other antibody conjugates.

Example 8

Preparation of Ab-STING Agonist Conjugates Via Transglutaminase Conjugation

The antibody drug conjugate listed in Table 6 were prepared as described in Example 7, using the starting linker-payload constructs shown as the starting material in the table.

TABLE 6

| ADC product | Linker-payload | humanized 1D9 isotype | Payload | DAR | Aggregation % | Yield % |
|---|---|---|---|---|---|---|
| ADC-B15 | C-30 | hIgG1 | Compound I-5c | 1.6 | BLQ | 64 |

Example 9

Procedure for Preparation of Mouse Ab-STING Agonist Conjugates Via Stochastic Cysteine Conjugation To a solution of an anti-mCCR2 MC-21 antibody (Universitaetsklinikum Regensburg, Regensburg, Germany; described in Mack, M. et al. *J. Immunol.* 2001, 166, 4697-4704 and WO 2007/115713) (mIgG2a with L235 Å-G237 Å-E318A mutation in heavy chain) in 25 mM sodium citrate, pH 5.5 buffer (3.4 mg/mL) was added 0.5M tris, 25 mM EDTA, pH 8 solution (10% of the total volume) and TCEP (10 mM solution in H$_2$O, 20 equiv.). The reaction mixture was purged with argon and incubated at 37° C. for 1.5 h with gentle shaking. The reaction mixture was purified following the preparative SEC method described herein. The purified reduced antibody solution was cooled to 4° C. Dehydroascorbic acid solution in DMSO (2 mM, 3 equiv. relative to the reduced antibody) was added and the resulting mixture was stored at 4° C. overnight. The solution was warmed to rt, and then the desired linker-payload construct (5 mM solution in DMA, 7 equiv. relative to the reduced antibody) was added slowly. The reaction was incubated at rt for another 1.5-2 h with gentle shaking. The reaction mixture was purified following the preparative SEC method described herein to give the ADC. The ADC concentration, percentage aggregation, and DAR were determined by UV absorbance, analytical SEC, and LC-QTOF respectively, as described in analytical methods.

A schematic of this procedure is depicted in FIG. 1.

Example 10

Preparation of Additional Mouse Ab-STING Agonist Conjugates Via Stochastic Cysteine Conjugation The antibody drug conjugates listed in Table 7 were prepared as described in Example 9, using the linker-payload constructs and antibody shown as the starting materials.

TABLE 7

| ADC product | Linker-payload | humanized 1D9 isotype | Payload | DAR | Aggregation % | Yield % |
|---|---|---|---|---|---|---|
| ADC-B21 | C-38 | MC-21 | Compound No. 14 | 3.6 | BLQ | 63 |

Example 11

Plasma Stability Assay Conditions

Test compounds were spiked into 1 mL of plasma at a concentration of 10 μg/mL and then 5 equal volume aliquots were dispensed into 2 mL Eppendorf microfuge tubes (labeled 0, 24, 48, 72, and 96 hours). For the 0 h timepoint tubes were immediately stored at −80° C. and the remaining tubes were incubated at 37° C. with moderate shaking. Aliquots were removed from the incubator at their corresponding time point and stored at −80° C. After all samples have been collected, they were thawed at rt and placed on wet ice. 50 μL of each sample was dispensed in triplicate into 96-well microtiter plate. Samples were quenched with 200 μL of ice cold methanol containing 50 nM of internal standard. Samples were vortexed for 2 min then centrifuged at 3000 rpm for 10 min. 185 μL of supernatant was transferred to a clean injection plate then dried down under N$_2$ gas at 40° C. Dried sample extracts were reconstituted with 100 L of LCMS grade water then vortexed for 1 min in preparation for LC-MS/MS analysis.

Each sample was separated by reverse phase HPLC using a Synergi 2.5p Polar-RP 100A C18 column (2.0 mm×30 mm), (Phenomenex®) at 40° C. using a gradient consisting of 0.1% formic acid in water (Solvent A) and 0.1% formic acid in acetonitrile (Solvent B). Analytes were detected by positive ion spray in multiple-reaction monitoring (MRM) mode using a SCIEX API 4500 QTRAP instrument. Percentage payload loss in human, primate and mouse plasma at various time points is reported in Table 8.

TABLE 8

| ADC | Payload loss (%) in human plasma | | | | Payload loss (%) in cyno plasma | | | | Payload loss (%) in mouse plasma | | | |
|---|---|---|---|---|---|---|---|---|---|---|---|---|
| | 1 d | 2 d | 3 d | 4 d | 1 d | 2 d | 3 d | 4 d | 1 d | 2 d | 3 d | 4 d |
| ADC-B2 | NA | NA | NA | NA | 4.5 | 9.9 | 15.6 | 21.7 | NA | NA | NA | NA |
| ADC-B5 | 1.0 | 1.8 | 2.8 | 3.3 | 0.7 | 0.9 | 2.2 | 1.4 | 2.2 | 3.9 | 6.4 | 7.6 |
| ADC-B6 | 0.3 | 1.0 | 1.6 | 2.4 | 0.6 | 1.0 | 1.8 | 2.1 | 1.4 | 2.0 | 3.1 | 3.9 |
| ADC-B7 | 2.5 | 6.2 | 11.0 | 16.0 | 4.8 | 10.2 | 16.9 | 22.6 | 3.2 | 6.5 | 9.6 | 3.3 |
| ADC-B14 | 1.8 | 3.4 | 4.9 | 5.9 | 1.4 | 3.0 | 3.9 | 5.5 | 4.5 | 6.8 | 16.0 | 19.4 |
| ADC-B17 | 0.7 | 1.1 | 1.6 | 2.2 | 0.6 | 0.8 | 1.4 | 1.7 | 2.7 | 4.1 | 11.1 | 9.9 |

Example 12

THP1 Dual Lucia Reporter Gene Assay Conditions

THP1-Dual™ KI-hSTING-R232 cells (InvivoGen #thpd-r232) were derived from the human THP-1 monocyte cell line by stable biallelic knockout of the endogenous human HAQ STING gene and knockin of the R232 variant of human STING. These cells also stably express inducible secreted Lucia luciferase reporter gene under the control of an ISG54 (interferon-stimulated gene) minimal promoter in conjunction with five IFN-stimulated response elements (ISRE). The expression of reporter gene allows the study of the IFN regulatory factor (TRF) pathway by assessing the activity of Lucia luciferase. In addition to human STING and luciferase, these cells were engineered to stably express human CCR2 to allow the study of target-mediated activation of IRF pathway. The THP-1 cells express endogenous human CCR2 at a much lower density compared to that of the engineered cells to over express human CCR2. Therefore the empty vector cells could still be used as the negative control.

On the day of experiment, the cells were plated to a white, 384-well plate (Corning 356661) at 15,000 cells/25 μL per well density in growth media (RPMI 1640, 2 mM L-glutamine, 25 mM HEPES, 10% heat-inactivated fetal bovine serum, 100 μg/mL Normocin™ 100 U/mL-100 μg/mL Pen- Strep, 10 μg/mL of blasticidin, 100 μg/mL of Zeocin, and 1 μg/mL of Puromycin). The cell plates were dosed with 5 μL of the hCCR2-targeting-ADC samples or compound samples, and then incubated at 37° C. for 20 hours. At the end of the incubation, 10 μL/well of the QUANTI-Luc™ (InvivoGen #rep-qlc1) were added, and luminescence was measured immediately using the LeadSeeker.

For the assay method described above, percent luminescence signal induction for each test ADC or test compound, at various concentrations, was calculated relative to untreated and control treated samples. Compound concentration versus percent signal induction curves were fitted to generate $EC_{50}$ values. One skilled in the art will appreciate that the values generated as $EC_{50}$ values are subject to experimental variation. The observed $EC_{50}$ and Emax are reported in Table 9. The data in Table 9 clearly indicates that conjugation of either Compound No. 14 or Compound I-5c to humanized 1D9 or its IgG4 isotype dramatically increases in vitro potency in the hCCR2-overexpressing THP1 cell line.

TABLE 9

| ADC/Compound | hCCR2-overexpressing THP1 | | Vector THP1 | |
|---|---|---|---|---|
| | $EC_{50}$ nM | Emax | $EC_{50}$ nM | Emax |
| ADC-B1 | NA | NA | >370 | 0.6 |
| ADC-B2 | 2.63 | 75.1 | 193 | 61.8 |
| ADC-B3 | NA | NA | >160 | 4.6 |
| ADC-B4 | NA | NA | >214 | 5.3 |
| ADC-B5 | NA | NA | 98.6 | 24.5 |
| ADC-B14 | 0.53 | 102 | 366 | 48.5 |
| ADC-B15 | 302 | 59.2 | >1000 | 1.28 |
| ADC-B16 | 2.46 | 107 | >1000 | 34.5 |
| ADC-B17 | 1.14 | 97.8 | >1000 | 25.8 |
| ADC-B18 | 48.2 | 56.1 | >1000 | 1.52 |
| ADC-B19 | 3.09 | 78.3 | >200 | 2.19 |
| Compound No. 14 | 760 | 97 | 710 | 129 |
| Compound I-5c | 850 | 100 | 790 | 126 |

Example 13

Pharmacokinetics Evaluation in Mouse

For in vivo evaluation of the ADCs in naïve Balb/C mouse, female Balb/C mice at 6-8 weeks of age (purchased from Jackson Laboratory) were used. Mice were fed with normal diet and housed in a SPF animal facility in accordance with the Guide for Care and Use of Laboratory Animals and regulations of the Institutional Animal Care and Use Committee. Animals were kept at a temperature of 18-26° C., a relative humidity of 50±20% and intermittent light and dark cycles of 12 hours with food and water available ad libitum.

Pharmacokinetics of the ADCs were studied following injection of ADCs into Balb/C mice. Serum samples were taken at various time points and stored frozen for analysis.

The mouse plasma levels of total antibodies and conjugated payloads were measured by a 2-in-1 immunocapture based LC/MS assay on a Shimadzu UHPLC system interfaced to a Sciex 6500 QTRAP mass spectrometer. Briefly, mouse plasma samples were incubated with anti-human IgG coated magnetic beads for 45 min at room temperature, then non-specifically bound proteins were removed by washing the magnetic beads with PBST (PBS buffer at pH 7.4, containing 0.05% tween 20) and PBS buffer consecutively. After that, both naked antibodies (DAR=0) and ADCs (DAR≥1) were eluted from the magnetic beads into 0.1% trifluoroacetic acid. After neutralizing the eluents and spiking in stable isotope labeled internal standards, one aliquot of sample was pipetted out and digested with papain for 1 hour at 37° C. then used for the LC/MS analysis of conjugated payloads. The remaining samples were subjected to trypsin/lys-C digestion for 1 hour at 70° C. then used for the LC/MS analysis of total antibodies.

The free payload in the circulation was also measured by LC/MS after performing plasma protein precipitation. In short, mouse plasma was mixed with 8 volumes of methanol containing stable isotope labeled internal standard, then the supernatants were evaporated to dryness at 40° C. under a gentle nitrogen stream. Finally, the residues were reconstituted in LC/MS grade water prior to LC/MS analysis.

The PK profile of ADC-B14, ADC-B15, ADC-B16, ADC-B17, and ADC-B18 is summarized in Table 10. Graphical representation of the plasma PK is shown in FIGS. 4-8.

TABLE 10

| ADC (payload dose) | | Half life (h) | AUC (last) (h * nM) |
|---|---|---|---|
| ADC-B14 (0.05 mg/kg) | Conjugated payload | 41 | 47600 |
| | Antibody | 68 | 14370 |
| ADC-B15 (0.05 mg/kg) | Conjugated payload | 53 | 37282 |
| | Antibody | 73 | 13434 |
| ADC-B16 (0.05 mg/kg) | Conjugated payload | 44 | 39200 |
| | Antibody | 58 | 12300 |
| ADC-B17 (0.05 mg/kg) | Conjugated payload | 36 | 58200 |
| | Antibody | 59 | 20400 |
| ADC-B18 (0.05 mg/kg) | Conjugated payload | 49 | 65400 |
| | Antibody | 60 | 39300 |

Example 14

Tolerability Evaluation in Mouse

Figure 9:
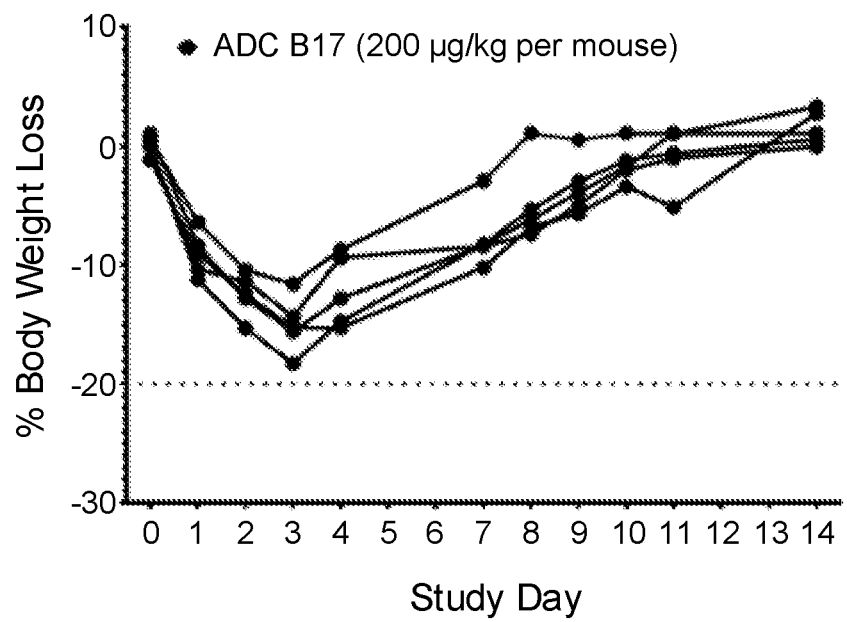
FIG. 9 depicts the change in body weight over time of mice dosed with ADC B-17.
Figure 9:
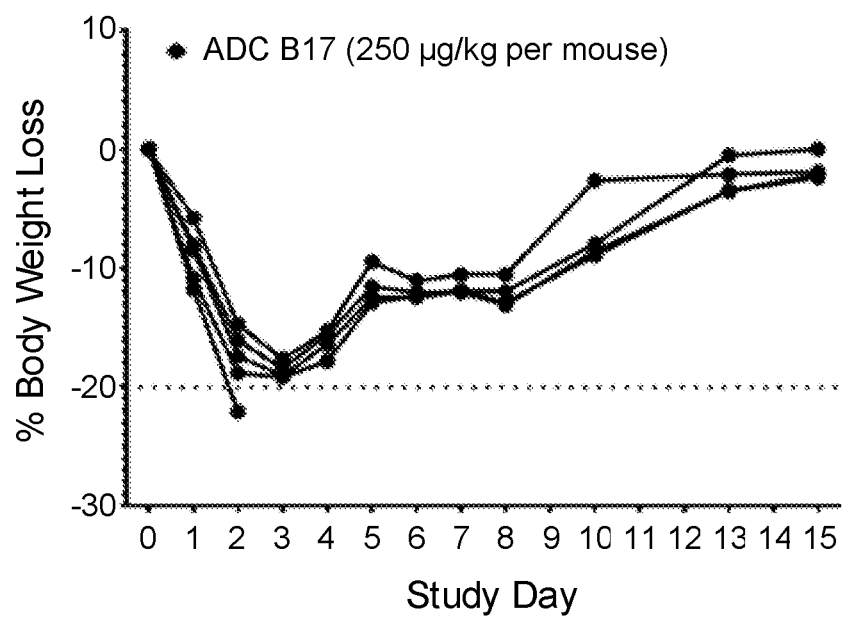
Figure 10:
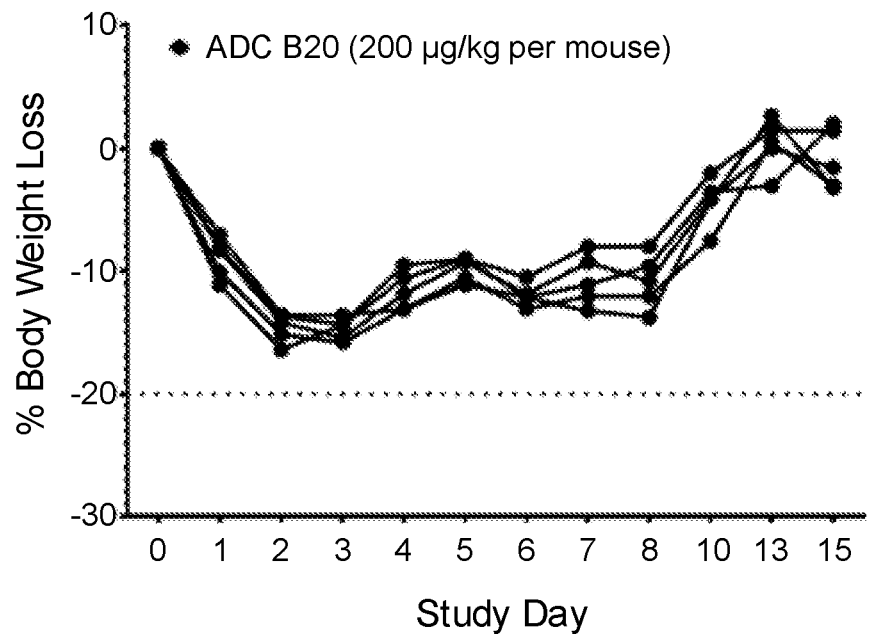
FIG. 10 depicts the change in body weight overtime of mice dosed with ADC B-20.
Figure 10:
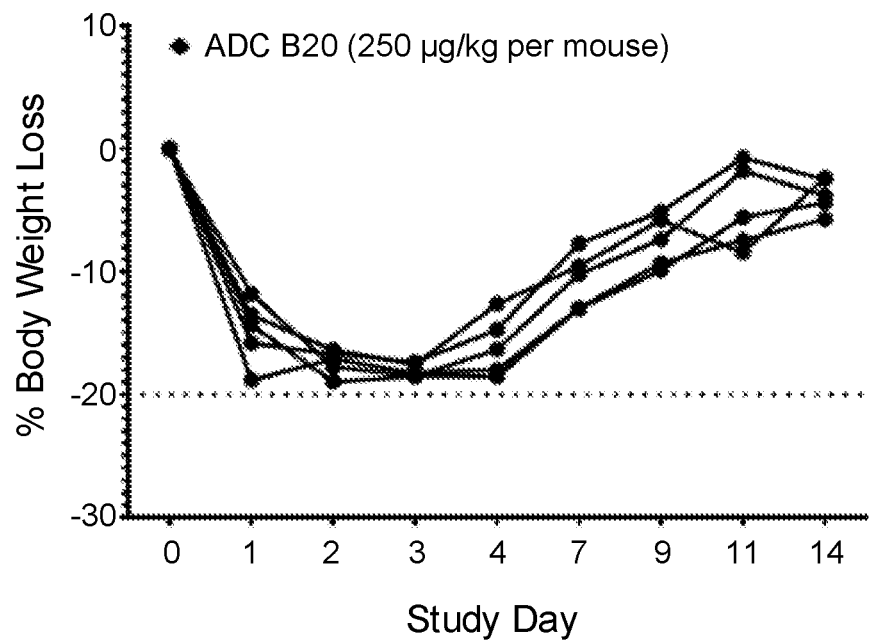

The tolerability of the ADC was evaluated in naïve C57BL/6 mice. On Study Day 0, animals were weighed, and then administered with the indicated amounts of ADC (by payload concentration) intravenously. Animals were then weighed regularly (no more than 3 days between each measurement) for at least 14 days post dosing, and body weight loss was calculated after each measurement based upon the pre-dosing starting weight. Any animals with greater than 20% body weight loss, or which were moribund or otherwise exhibited signs of distress exceeding the humane endpoints of the study, were removed from the study and euthanized according to the guidelines within the IACUC protocol. The maximum tolerated dose (MTD) was calculated as the highest dose (by payload concentration) at which no animals were found dead or needed to be removed from the study, either due to body weight loss greater than 20% or having otherwise exceeded a humane endpoint. The MTD of ADC-B17 was 200 μg/kg (by payload concentration, FIG. 9) and the MTD of ADC-B20 was 250 μg/kg (by payload concentration FIG. 10).

Example 15

Antitumor Activity Evaluation in Mouse

Efficacy of ADC-B21 compared with Compound No. 14 was evaluated in an MC38 (murine colon adenocarcinoma) tumor bearing C57BL/6 mouse model. For tumor implantation, $1 \times 10^6$ MC38 cells were subcutaneously injected into C57BL/6 mice and mice were subsequently monitored for tumor growth. When tumor volumes reached an average of approximately 100 mm$^3$, animals were randomized by tumor volume, and dosed intravenously with 100 µL of either vehicle, Compound No. 14 at 2000 µg/kg, or ADC-B21 at 50 µg/kg. The first day of dosing was considered Study Day 0. Compound No. 14 and vehicle were dosed again on Study Days 3 and 6, while ADC-B21 was administered as a single administration on Study Day 0. Tumor volumes and body weight measurements were taken at least twice a week until the end of study, and animals were removed for body weight loss greater than 20% from starting body weight, or tumor volumes exceeding 2000 mm$^3$. By Study Day 63, Compound No. 14 treated animals had a total of 1 out of 6 complete responses, compared with ADC-B21 treatment, which had a total of 4 out of 6 complete responses.

Figure 11:
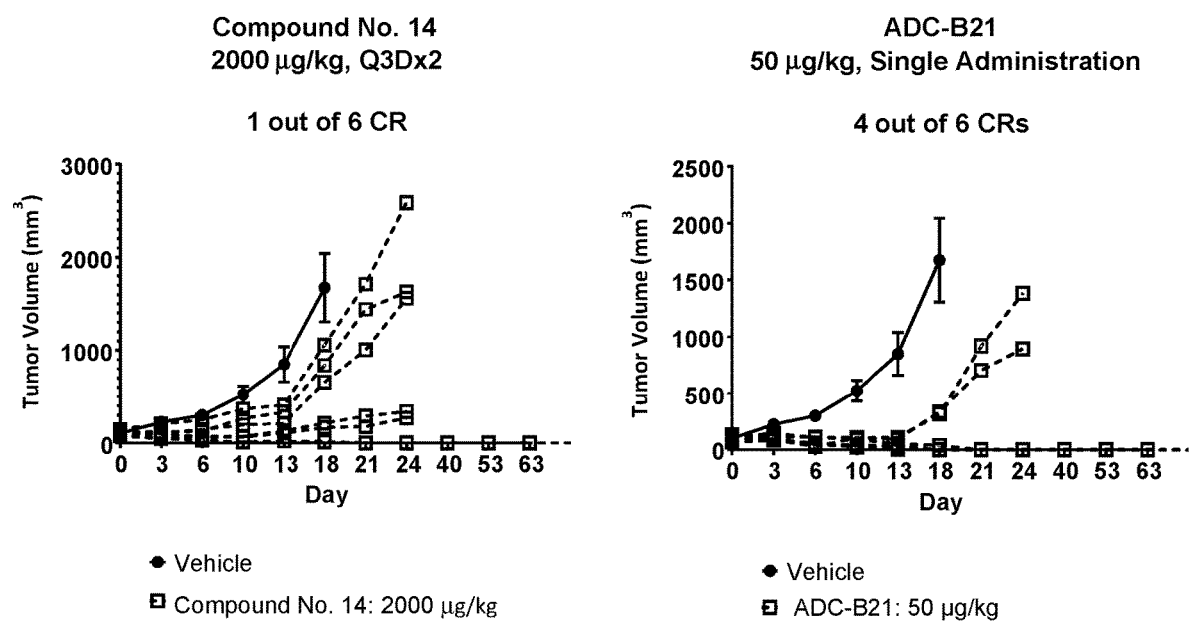
FIG. 11 depicts the antitumor activity of Antibody Drug Conjugate B-21 compared to the antitumor activity of its payload alone.

The graphical representation of the observed antitumor activity is shown in FIG. 11, demonstrating anti-CCR2 ADC's significantly enhanced efficacy at much lower dose level comparing to its payload alone.

Example 16

Toxicity Pharmacodynamics Evaluation in Non-Human Primate

2 ADC variants were evaluated in toxicity studies in the cynomolgus monkey.

A single dose study was performed with intravenous administration of ADC-B2 at 0.15, 0.5, 1.5, or 5 mg/kg (2 monkeys/sex/group) (protein dose). Administration of 5 mg/kg ADC-B2 was associated with early mortality in two animals on Day 2, attributed to pulmonary toxicity that was similar to previous studies with unconjugated payload (Compound No. 14) (clinical signs of decreased body pale mucous membranes, and decreased heart sounds, and histologic findings of mild pulmonary vascular congestion and acute alveolar hemorrhage that correlated to macroscopic red discoloration, intra-alveolar edema and fibrin, increased alveolar macrophages and neutrophilic infiltrates, and in one animal, pleural and pericardial effusion). Other findings unique to these early mortality animals were present in the bone marrow (decreased hematopoietic cellularity, single cell necrosis and increased histiocytes), liver (multifocal random foci of necrosis), and lymphoid tissues (decreased cellularity and/or necrosis of germinal centers in the spleen, and tonsil, and single cell necrosis in the thymus). On clinical pathology and cytokine analysis of one early mortality animal where samples were available was evidence of pro-inflammatory/acute phase response, and elevations in IP-10, IL-6, MCP 1, and TNF-α cytokine levels that were similar to animals surviving to terminal euthasia. Histologic findings in animals surviving to terminal euthanasia were limited to lymph node increased cellularity (due to increases in lymphocytes and histiocytic cells) at ≥1.5 mg/kg, and lymph node germinal center necrosis in one animal at 5 mg/kg. Pharmacologic endpoints added to the study consisted of flow cytometry to evaluate monocyte populations, and identified dose-dependent decreases in relative percentages of classical, intermediate, and non-classical monocytes, and myeloid derived suppressor cells (MDSC) at Day 1: 6 and 24 hours postdose with partial recovery by Day 1: 48 hours postdose.

A repeat dose study was performed with intravenous administration of ADC-B17 scheduled every 2 weeks for a total of 3 doses at 0.3, 1, or 3 mg/kg (protein dose) (2 monkeys/sex/group); however, due to the early death of 2 animals from the 3 mg/kg dose group following the second dose on Day 15, the remaining 2 animals in Group 4 received a reduced dosage of 2 mg/kg on Day 29 (third/final dose). Repeat administration of ≥0.3 mg/kg ADC-B17 was associated with the development of anti-drug antibodies (ADA) in 10 out of 12 animals at 1 or more time points after Day 15 (1 to 3 orders of magnitude increase in signal/noise ratio), directed mostly against the immunostimulatory payload of the ADC, with some ADA also observed at the end of the time course toward the antibody component of the ADC. These ADA were associated with decreases in exposure (Cmax) following the third dose in most ADA-positive animals. ADC-B17-related early mortality was observed at ≥1 mg/kg. One animal at 1 mg/kg was euthanized in moribund condition on Day 29, approximately 7 hours postdose. At 3 mg/kg, 1 animal was found dead approximately 6 hours postdose on Day 15, and 1 animal was euthanized in moribund condition on Day 15, approximately 7 hours postdose. ADC-B17-related clinical signs in these animals preceding death included red skin (face), decreased activity, hunched posture, body weight loss, excessive salivation, eyes partly closed, sunken eyeballs, increased body temperature, heart murmur, and/or elevated heart rate and/or respiration rate. The cause of mortality was attributed to immune-related effects considered likely due to immunogenicity/hypersensitivity reactions, although direct effects of ADC-B17 could not be ruled out. Serum chemistry findings from all 3 early decedents were generally similar to animals that survived to terminal euthanasia and were consistent with systemic pro-inflammatory response and muscle and/or hepatocellular damage. Hematology and coagulation parameters were evaluated in the animal euthanized moribund on Day 29 but not the animals on Day 15; there were minimal decreases in lymphocytes and eosinophils attributed to stress and no changes in coagulation parameters. The observed immunophenotyping changes were similar to that of the surviving animals, described below. Most microscopic findings in early decedent animals on Day 15 were similar to but more severe than animals that survived to terminal euthanasia and consisted of minimal hepatocellular necrosis and systemic findings consistent with immune-mediated effects (immune cell infiltrates in the liver sinusoids, adrenal gland, lung interstitium and spleen; thrombosis of the capillaries of the lung; necrosis/fibrin deposition in the spleen; myocardial degeneration; and micro-hemorrhages in the adrenal gland and epicardial fat). Additional findings unique to early decedents were considered secondary to stress or moribund status (decreased thymus cellularity correlating to decreased thymic weight and pancreas acinar cell degeneration). In the animal euthanized moribund on Day 29, the only finding was minimal adrenal gland hemorrhage.

In animals surviving to terminal euthanasia, clinical pathology findings were observed at ≥0.3 mg/kg on Day 3 consisting of mild to moderate increases in 1 or more of: aspartate aminotransferase, alanine aminotransferase, glutamate dehydrogenase, and creatine kinase. These findings were consistent with a muscle and/or hepatocellular origin and lacked clear histologic correlates. Other findings on Day 3 were consistent with a systemic proinflammatory response/acute phase response (minimal to mild increased globulin and c reactive protein and minimal to mild decreases in total protein, albumin, and albumin/globulin ratio) that correlated histologically to inflammatory cell infiltrates in multiple tissues, or dehydration (mildly increased urea, creatinine, and phosphorus) with no histologic correlates. Each of these changes partially to completely recovered by Day 30. Additional serum chemistry changes on Days 14 and/or 30 in males only consisted of mild increases in globulins, and mildly elevated total bilirubin, both of which were consistent with an ongoing acute phase inflammatory response. Hematology and coagulation findings in individual animals at ≥0.3 mg/kg at terminal euthanasia on Day 30 consisting of mild increases in white blood cell counts, neutrophil counts, fibrinogen, and activated partial thromboplastin time, and mild decreases in red blood cell count, hemoglobin, hematocrit. These findings were consistent with a systemic proinflammatory response/acute phase response.

Figure 12:
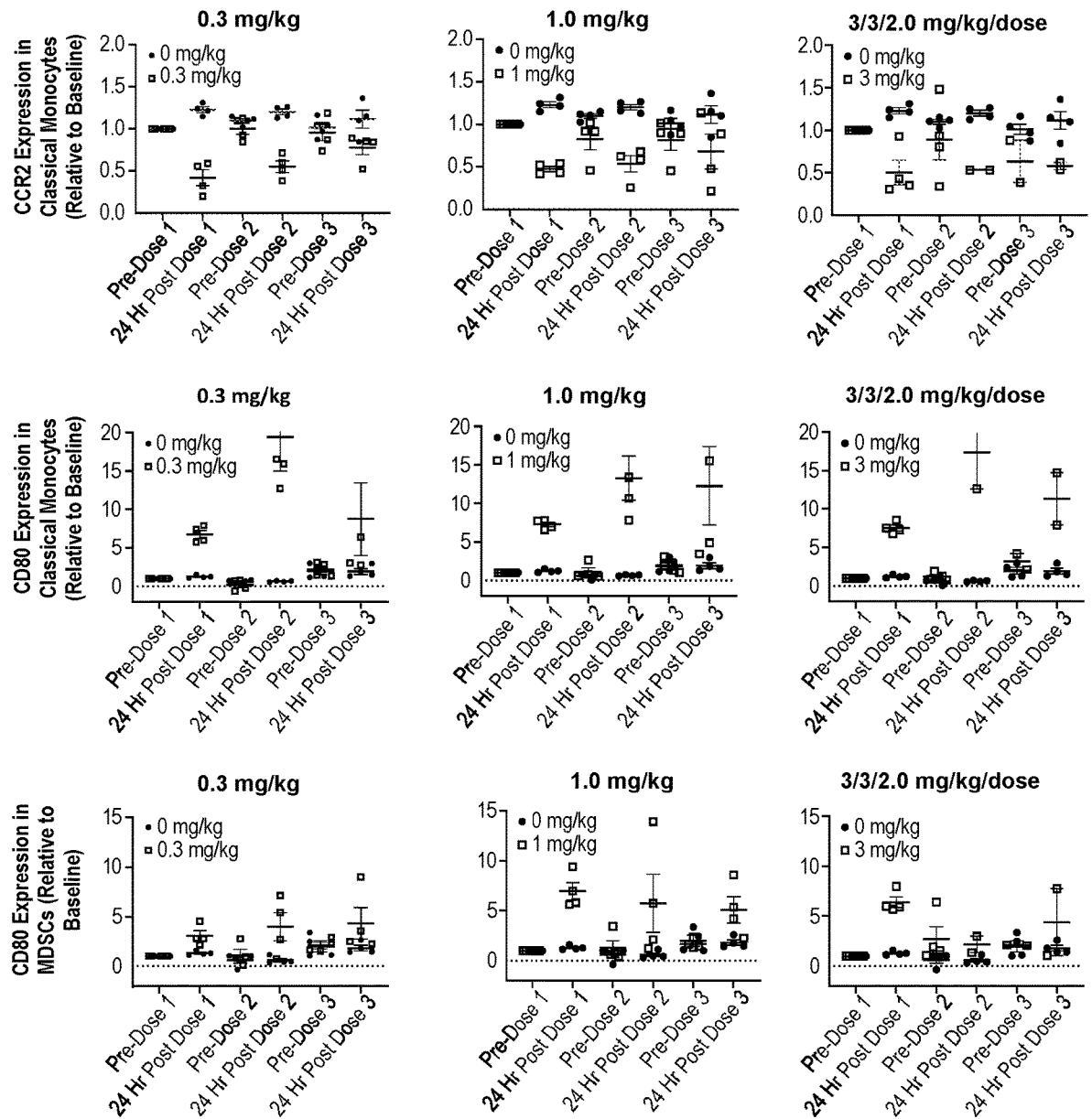
FIG. 12 depicts the change in CCR2 and CD80 expression in monocytes and MDSCs in non-human primates after dosing with Antibody Drug Conjugate B-17.

Changes on monocytes and MDSCs in plasma samples were evaluated using a flow cytometry panel designed to evaluate monocyte and MDSC counts, as well as the CCR2, CD80, and CD86 expression on the monocytes. Findings from this evaluation were consistent with expected pharmacology ≥0.3 mg/kg ADC-B17 and consisted of a dose-responsive mild to severe decrease in absolute counts of classical monocytes, non-classical monocytes, and myeloid derived suppressor cells (MDSC) after each dose at with recovery toward or above baseline prior to each subsequent dose as measured by flow cytometry. CCR2 expression in the classical monocytes was reduced following dosing, with a recovery to near baseline at all doses prior to subsequent doses (FIG. 12, top). In addition, the expression of CD80 in both classical monocytes as well as MDSCs was found to increase following each dose, and then recover to at or below baseline levels prior to subsequent dosing (FIG. 12, middle and bottom, respectively).

Figure 13:
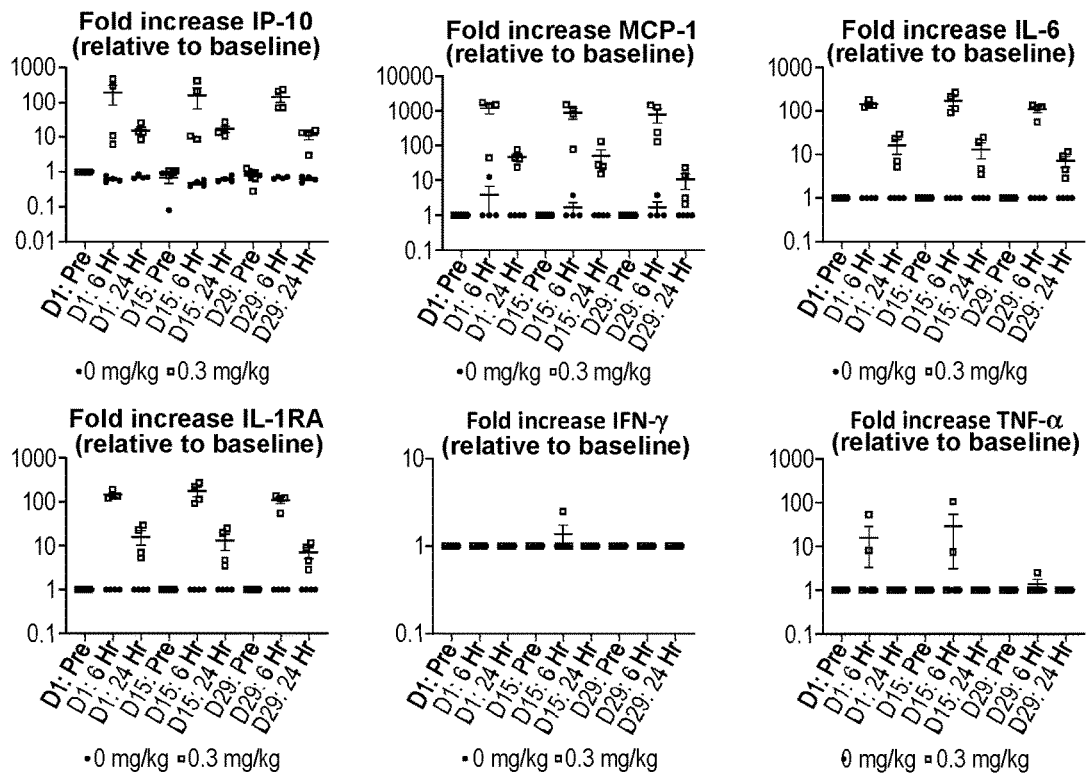
FIG. 13 depicts the change in serum IL-IRA, IL-6, TNF-α, and IFN-γ in non-human primates after dosing with Antibody Drug Conjugate B-17.

Changes in cytokines were also evaluated in plasma samples, and showed at ≥0.3 mg/kg ADC-B17 consisted of large magnitude dose independent increases in serum IP-10 and MCP-1 concentrations, potential biomarkers of pharmacology, which peaked at 6 hours postdose and returned or trended to return to baseline values 24 hours postdose. Additional elevations in serum IL-1RA, IL-6, TNF-α, and IFN-γ were observed that peaked at 6 hours postdose and returned or trended to return to baseline values 24 hours postdose or prior to the following dose (FIG. 13).

Histologic findings in animals at terminal euthanasia consisted of multifocal hepatocellular necrosis without clinical pathology correlates at ≥0.3 mg/kg. At ≥1 mg/kg there was minimal to mild decreased cellularity of both erythroid and myeloid precursors in the bone marrow (correlating to hematology findings of mildly decreased red blood cells and, in 1 animal, markedly decreased lymphocytes), mixed cell infiltrates sporadically observed within the adrenal gland and liver sinusoids, increased cellularity (mixed cells) of the splenic red pulp which correlated to mildly increased spleen weight, and minimal focal hemorrhage in the duidenum or heart. These organs with inflammatory cell infiltrates/hemorrhage were considered likely part of a systemic proinflammatory response and were not considered direct target organ toxicities. Immunohistochemistry for human IgG, monkey IgG and IgM, $C_3$, and/or $C_9$ was performed in order to determine whether immune complex formation and tissue deposition was present in areas of immune cell infiltrates and/or tissue damage. No granular deposits indicative of immune complex formation were detected.

Example 17

Pharmacokinetics Evaluation in Non-Human Primate

Serum samples were taken from non-human primates dosed with ADC-B17 described in example 16 at various time points and stored frozen for analysis. The monkey plasma levels of total antibodies and conjugated payloads were measured by a 2-in-1 immunocapture based LC/MS assay on a Shimadzu UHPLC system interfaced to a Sciex 6500+ QTRAP mass spectrometer. Briefly, monkey plasma samples were incubated with anti-idiotype antibody coated magnetic beads for 60 min at room temperature, then non-specifically bound proteins were removed by washing the magnetic beads three times with PBS buffer. After that, both naked antibodies (DAR=0) and ADCs (DAR≥1) were eluted from the magnetic beads into 0.1% trifluoroacetic acid. After neutralizing the eluents and spiking in stable isotope labeled internal standards, one aliquot of sample was pipetted out and digested with trypsin/lys-C for 1 hour at 60° C., then used for the LC/MS analysis of total antibodies. The remaining samples were subjected to papain digestion for 1 hour at 37° C., then used for the LC/MS analysis of conjugated payloads.

The free payload in the circulation was also measured by LC/MS after performing plasma protein precipitation. In short, monkey plasma was first spiked with stable isotope labeled Compound No. 14 followed by protein precipitation using methanol, then the supernatants were evaporated to dryness under a gentle nitrogen stream. Finally, the residues were reconstituted with ammonium acetate solution prior to LC/MS analysis.

Figure 14:
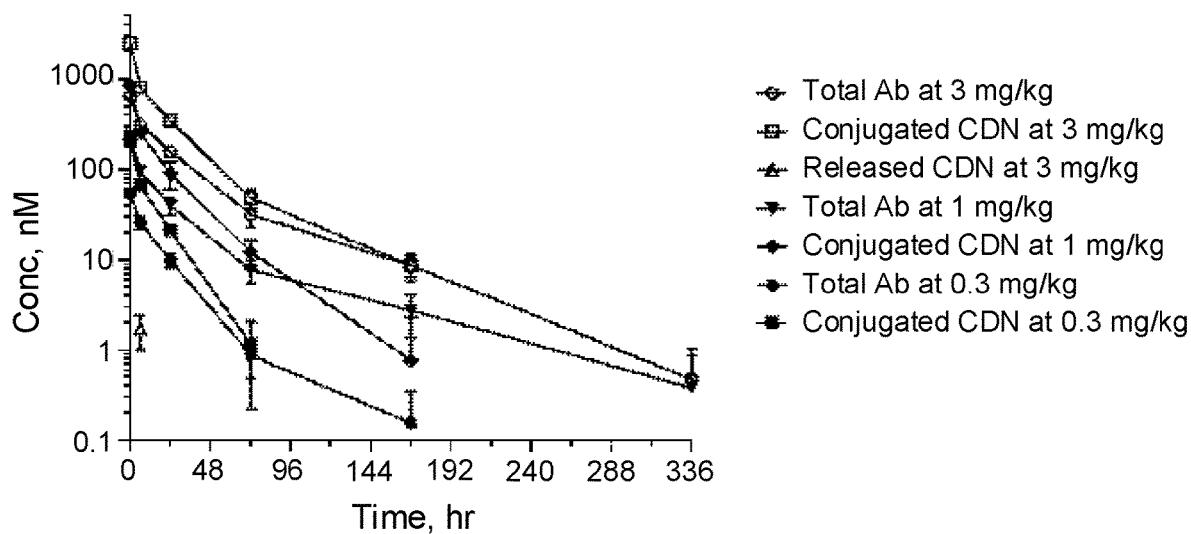
FIG. 14 depicts the non-human primate PK profile of Antibody Drug Conjugate B-17.

The PK profile of ADC-B17 is summarized in Table 11. Graphical representation of the plasma PK is shown in FIG. 14.

TABLE 11

| ADC-B17 protein dose | | Half life (h) | AUC (last) (h * nM) |
| --- | --- | --- | --- |
| 3 mg/kg | Conjugated payload | 25 | 33310 |
| | Antibody | 40 | 14470 |
| 1 mg/kg | Conjugated payload | 17 | 9648 |
| | Antibody | 52 | 4092 |
| 0.3 mg/kg | Conjugated payload | 11 | 2220 |
| | Antibody | 18 | 885 |

Example 18 (Prophetic)

Combination Therapy with PD-1/PD-L1 Antibodies

The tolerability of the ADC in combination with an ant-PD-1 and/or anti-PD-L1 antibody can be evaluated in naïve C57BL/6 mice.

The ADC and anti-PD-1/anti-PD-L1 combinations that can be used are shown in Table 12.

TABLE 12

| ADC product | Linker-Payload Construct | Humanized 1D9 isotype | Payload | Antibody |
|---|---|---|---|---|
| ADC-B2 | C-21 | hIgG4 | Compound No. 14 | PD-1 |
| ADC-B5 | C-4 | hIgG4 | Compound No. 14 | PD-1 |
| ADC-B17 | C-38 | hIgG1 | Compound No. 14 | PD-1 |
| ADC-B4 | C-22 | hIgG4 | Compound No. 14 | PD-1 |
| ADC-B20 | C-38 | hIgG1 | Compound No. 14 | PD-1 |
| ADC-B21 | C-38 | MC-21 | Compound No. 14 | PD-1 |
| ADC-B2 | C-21 | hIgG4 | Compound No. 14 | PD-L1 |
| ADC-B5 | C-4 | hIgG4 | Compound No. 14 | PD-L1 |
| ADC-B17 | C-38 | hIgG1 | Compound No. 14 | PD-L1 |
| ADC-B4 | C-22 | hIgG4 | Compound No. 14 | PD-L1 |
| ADC-B20 | C-38 | hIgG1 | Compound No. 14 | PD-L1 |
| ADC-B21 | C-38 | MC-21 | Compound No. 14 | PD-L1 |

For the tolerability studies, the ADC as shown in Table 12 can be dosed at 0.05 mg/kg and the anti-PD-1 and anti-PD-L1 antibodies can be dosed at 0.5, 5, or 50 mg/kg. Since anti-PD-1 antibody Pembrolizumab does not cross-react with rodent PD-1, mice will receive the rat anti-mouse PD-1 antibody J43 and the rat anti-mouse PD-L1 antibody MIH5, each at 0.5, 5, and 50 mg/kg.

On Study Day 0, animals can be weighed, and then intravenously administered the indicated amounts of ADC in combination with the indicates amounts of anti-PD-1 and/or anti-PD-L1 antibodies. Animals will then be weighed regularly (no more than 3 days between each measurement) for at least 14 days post dosing, and body weight loss can be calculated after each measurement based upon the pre-dosing starting weight. Any animals with greater than 2000 body weight loss, or which appears moribund or otherwise exhibits signs of distress exceeding the humane endpoints of the study, can be removed from the study and euthanized according to the guidelines within the IACUC protocol. The maximum tolerated dose (MTD) can be calculated as the highest dose (by payload concentration+PD-1/PD-L1 antibody concentration) at which no animals can be found dead or needed to be removed from the study, either due to body weight loss greater than 20% or having otherwise exceeded a humane endpoint. If satisfactory tolerability is achieved with the ADCs and either anti-PD-1 or anti-PD-L1 antibodies, combination therapies with ADCs and anti-PD-1 and anti-PD-L1 antibodies can be conducted in a similar way.

Efficacy Study for Combination Therapy in Mice

Efficacy of the ADCs as shown in Table 12 in combination with the anti-PD-1 antibody J43 or the anti-PD-L1 antibody MIH5 can be tested in the MC38 (murine colon adenocarcinoma) tumor bearing C57BL/6 mouse model. For tumor implantation, $1 \times 10^6$ MC38 cells can be subcutaneously injected into C57BL/6 mice and mice can be subsequently monitored for tumor growth. When tumor volumes reach an average of approximately 100 mm³, animals can be randomized by tumor volume, and dosed intravenously with 100 µL of either vehicle, the respective ADC of Table 12 at 50 µg/kg and J43 at 0.5, 5, or 50 mg/kg or MIH5 at 0.5, 5, or 50 mg/kg. The first day of dosing can be considered Study Day 0. Tumor volumes and body weight measurements can be taken at least twice a week until the end of study, and animals can be removed from the study for body weight loss greater than 20% from starting body weight, or tumor volumes exceeding 2000 mm³. The animals can be evaluated at Study Day 63, for complete and partial responses. If satisfactory reduction in tumor volume is not achieved with the combination of ADCs with either anti-PD-1 or anti-PD-L1 antibodies, combination therapies with ADCs and anti-PD-1 and anti-PD-L1 antibodies can be conducted in a similar way.

Efficacy Study for Combination Therapy in Non-Human Primates

The ADC in combination with anti-PD-1 antibody Pembrolizumab or anti-PD-L1 antibody Atezolizumab can be administered intravenously to cynomolgus monkeys every 2 weeks (Day 1 to Day 29) for a total of 3 doses at 0.3, 0.5, or 1 mg/kg (protein dose) (2 monkeys/sex/group). Pembrolizumab can be dosed at 0.5 or 15 mg/kg and Atezolizumab can be dosed at 0.5 or 15 mg/kg. Animals can be evaluated for hematological and coagulation parameters, general serum chemistry, and can be assessed histologically at the end of the study.

Blood samples can be taken from the non-human primates at various time points and monkey plasma levels of total antibodies and conjugated payloads can be measured by a 2-in-1 immunocapture based LC/MS assay on a Shimadzu UHPLC system interfaced to a Sciex 6500+QTRAP mass spectrometer as described above. The free payload in the circulation can also be measured by LC/MS after performing plasma protein precipitation as described above.

Example 19 (Prophetic)

Combination Therapy with Radiation

Tolerability Study

The tolerability of the ADC in combination with an anti-PD-1 and/or anti-PD-L1 antibody and radiation can be evaluated in naïve C57BL/6 mice.

The ADC, anti-PD-1 and/or anti-PD-L1 antibodies and radiation combinations that can be used are shown in Table 13.

TABLE 13

| ADC product | Antibody | Radiation |
|---|---|---|
| ADC-B2 | PD-1 | 0.5 Gy |
| ADC-B5 | PD-1 | 0.5 Gy |
| ADC-B17 | PD-1 | 0.5 Gy |
| ADC-B4 | PD-1 | 0.5 Gy |
| ADC-B20 | PD-1 | 0.5 Gy |
| ADC-B21 | PD-1 | 0.5 Gy |
| ADC-B2 | PD-L1 | 0.5 Gy |
| ADC-B5 | PD-L1 | 0.5 Gy |
| ADC-B17 | PD-L1 | 0.5 Gy |
| ADC-B4 | PD-L1 | 0.5 Gy |
| ADC-B20 | PD-L1 | 0.5 Gy |
| ADC-B21 | PD-L1 | 0.5 Gy |
| ADC-B2 | PD-1 | 1 Gy |
| ADC-B5 | PD-1 | 1 Gy |
| ADC-B17 | PD-1 | 1 Gy |
| ADC-B4 | PD-1 | 1 Gy |
| ADC-B20 | PD-1 | 1 Gy |

TABLE 13-continued

| ADC product | Antibody | Radiation |
|---|---|---|
| ADC-B21 | PD-1 | 1 Gy |
| ADC-B2 | PD-L1 | 1 Gy |
| ADC-B5 | PD-L1 | 1 Gy |
| ADC-B17 | PD-L1 | 1 Gy |
| ADC-B4 | PD-L1 | 1 Gy |
| ADC-B20 | PD-L1 | 1 Gy |
| ADC-B21 | PL-L1 | 1 Gy |

For the tolerability studies, the ADC can be dosed at 0.05 mg/kg, the anti-PD-1 and anti-PD-L1 antibodies can be dosed at 0.5, 5, or 50 mg/kg and the radiation can be dosed at 0.5 Gy and 1 Gy.

On Study Day 0, animals can be weighed, the radiation administered about 5 h before the intravenously administration of the indicated amounts of ADC in combination with the indicated amounts of anti-PD-1 J43 and/or anti-PD-L1 MIH5 antibodies. Animals will then be weighed regularly (no more than 3 days between each measurement) for at least 14 days post dosing, and body weight loss can be calculated after each measurement based upon the pre-dosing starting weight. Any animals with greater than 20% body weight loss, or which appears moribund or otherwise exhibits signs of distress exceeding the humane endpoints of the study, can be removed from the study and euthanized according to the guidelines within the IACUC protocol. The maximum tolerated dose (MTD) can be calculated as the highest dose of radiation in the combination therapy regimen at which no animals can be found dead or needed to be removed from the study, either due to body weight loss greater than 20% or having otherwise exceeded a humane endpoint. If satisfactory tolerability is achieved with the ADCs, anti-PD-1 or anti-PD-L1 antibodies and radiation, combination therapies with ADCs and anti-PD-1 and anti-PD-L1 antibodies and radiation can be conducted in a similar way.

Efficacy Study for Combination with Radiation Therapy in Mice

Efficacy of the ADCs in combination with anti-PD-1 and/or anti-PD-L1 antibodies and radiation as shown in Table 13 can be tested in the MC38 (murine colon adenocarcinoma) tumor bearing C57BL/6 mouse model. For tumor implantation, $1 \times 10^6$ MC38 cells can be subcutaneously injected into C57BL/6 mice and mice can be subsequently monitored for tumor growth. When tumor volumes reach an average of approximately 100 mm$^3$, animals can be randomized by tumor volume, and irradiated with either 0.5 Gy or 1 Gy radiation and intravenously dosed with 100 μL of either vehicle, the respective ADC of Table 13 at 50 μg/kg and anti-PD1 antibody J43 at 0.5, 5, or 50 mg/kg or anti-PD-L1 antibody MIH5 at 0.5, 5, or 50 mg/kg. The first day of dosing can be considered Study Day 0. Tumor volumes and body weight measurements can be taken at least twice a week until the end of study, and animals can be removed from the study for body weight loss greater than 20% from starting body weight, or tumor volumes exceeding 2000 mm$^3$. The animals can be evaluated at Study Day 63, for complete and partial responses. If satisfactory reduction in tumor volume is not achieved with the combination of ADCs with radiation and either anti-PD-1 or anti-PD-L1 antibodies, combination therapies with ADCs and radiation and anti-PD-1 and anti-PD-L1 antibodies can be conducted in a similar way.

Efficacy Study for Combination with Radiation Therapy in Non-Human Primates

Cynomolgus monkeys can be treated with 0.8 Gy and 1.2 Gy prior to administration of ADC and anti-PD-1 and/or anti-PD-L1 antibodies. The ADC in combination with anti-PD-1 antibody Pembrolizumab or anti-PD-L1 antibody Atezolizumab can be administered following radiation therapy intravenously to cynomolgus monkeys every 2 weeks (Day 1 to Day 29) for a total of 3 doses at 0.3, 0.5, or 1 mg/kg (protein dose) (2 monkeys/sex/group). Pembrolizumab can be dosed at 0.5 or 15 mg/kg and Atezolizumab can be dosed at 0.5 or 15 mg/kg. Animals can be evaluated for hematological and coagulation parameters, general serum chemistry, and can be assessed histologically at the end of the study.

Blood samples can be taken from the non-human primates at various time points and monkey plasma levels of total antibodies and conjugated payloads can be measured by a 2-in-1 immunocapture based LC/MS assay on a Shimadzu UHPLC system interfaced to a Sciex 6500+ QTRAP mass spectrometer as described above. The free payload in the circulation can also be measured by LC/MS after performing plasma protein precipitation as described above. Hematological recovery after radiation and extramedullary toxicity can be assessed in the animals.

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

What is claimed is:

1. A compound of the formula:

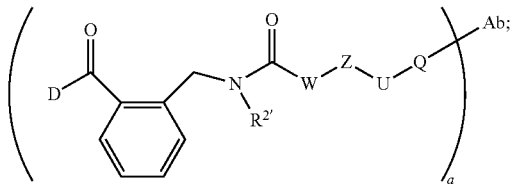

or a pharmaceutically acceptable salt thereof, wherein:
a is an integer from 1 to 8;
Ab is an anti-CCR2 antibody or an anti-CCR2 antigen-binding fragment;
$R^{2'}$ is $C_1$-$C_4$alkyl;
W is selected from:

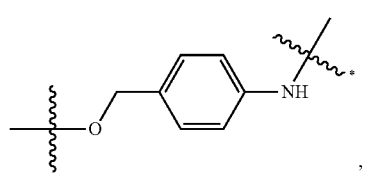

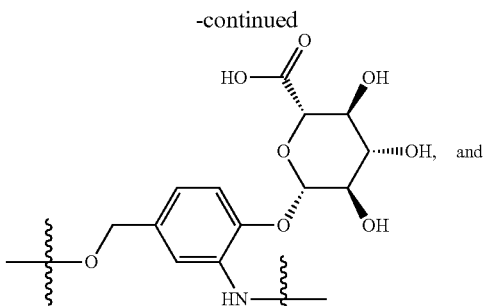

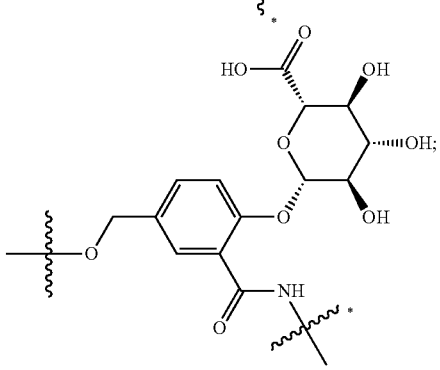

wherein

～ is the point of attachment to the carbonyl group; and

～* is the point of attachment to Z;

Z is Ala-Val or Val-Ala;

U is

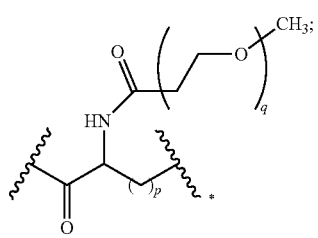

wherein p is an integer from 1 to 6;

q is an integer from 1 to 20;

～ is the point of attachment to Z;

～* is the point of attachment to Q;

Q is selected from

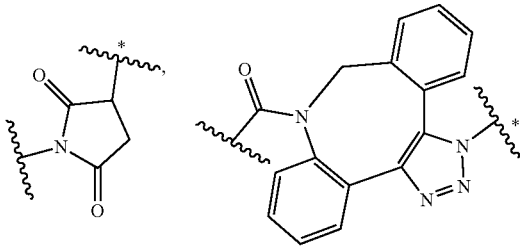

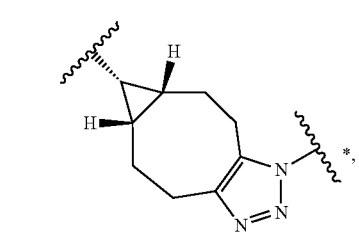

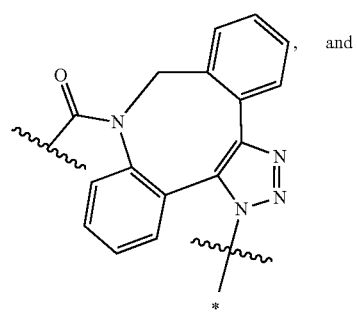

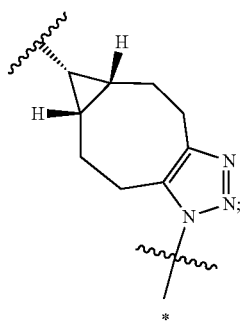

wherein

～ is the point of attachment to U;

～* is the point of attachment to Ab;

and

D is

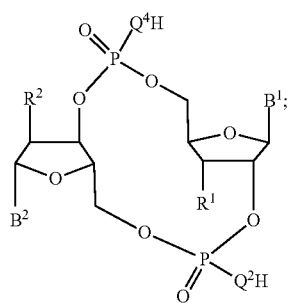

wherein:

$R^1$ and $R^2$ are each independently a hydroxy group or a halogen atom;

$B^1$ is:

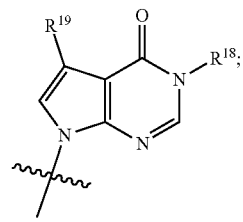

wherein $R^{18}$ is hydrogen or $C_{1-6}$ alkyl;

$R^{19}$ is a halogen atom; and

～ is the point of attachment to D; and $B^2$ is:

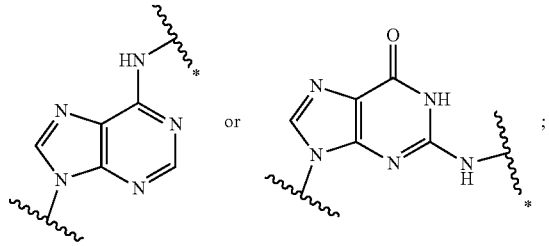
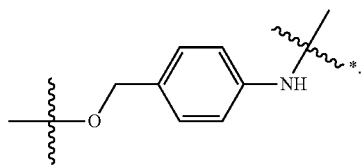

wherein
～ is the point of attachment to D; and
～* is the point of attachment to the parent molecular moiety; and
$Q^2$ and $Q^4$ are each independently an oxygen atom or a sulfur atom.

2. A compound of claim 1, or a pharmaceutically acceptable salt thereof, wherein Q is

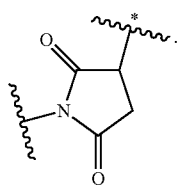 [SMILES: *C1CC(=O)N(*)C1=O]

3. A compound of claim 2, or a pharmaceutically acceptable salt thereof, wherein W is 4. A compound of claim 3, or a pharmaceutically acceptable salt thereof, wherein $R^2$ is —$CH_3$.

5. A compound of claim 4, or a pharmaceutically acceptable salt thereof, wherein a is an integer from 2 to 6.

6. A compound of claim 1, or a pharmaceutically acceptable salt thereof, wherein D is:

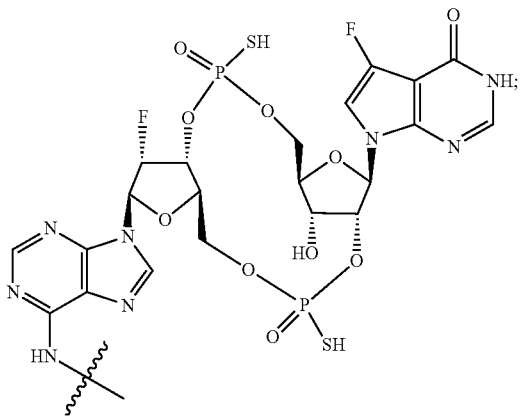 [SMILES: *Nc1ncnc2c1ncn2[C@@H]1O[C@@H]2COP(=O)(S)O[C@@H]3[C@H](O)[C@@H](COP(=O)(S)O[C@H]2[C@H]1F)O[C@H]3n1cc(F)c2c(=O)[nH]cnc21]

or a pharmaceutically acceptable salt thereof, wherein ～ is the point of attachment to the parent molecular moiety.

7. A compound of claim 1, or a pharmaceutically acceptable salt thereof, of formula (VI):

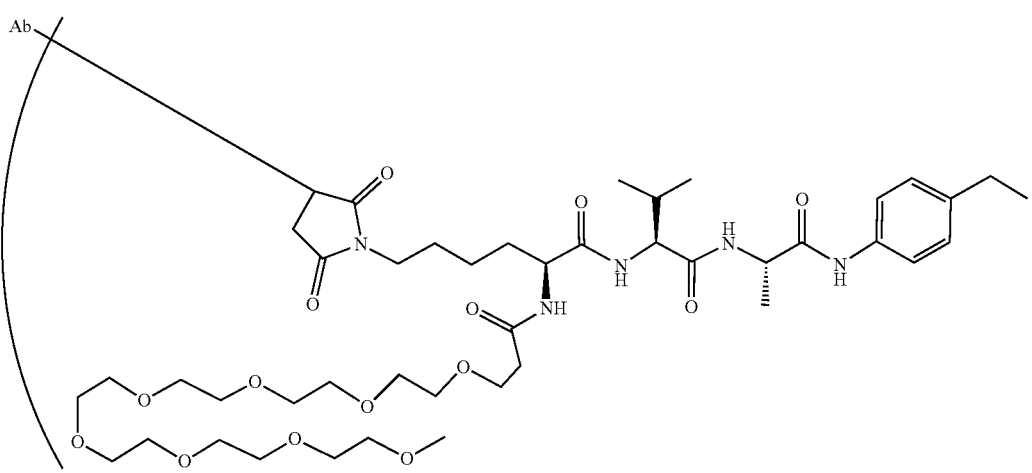

(VI)

-continued

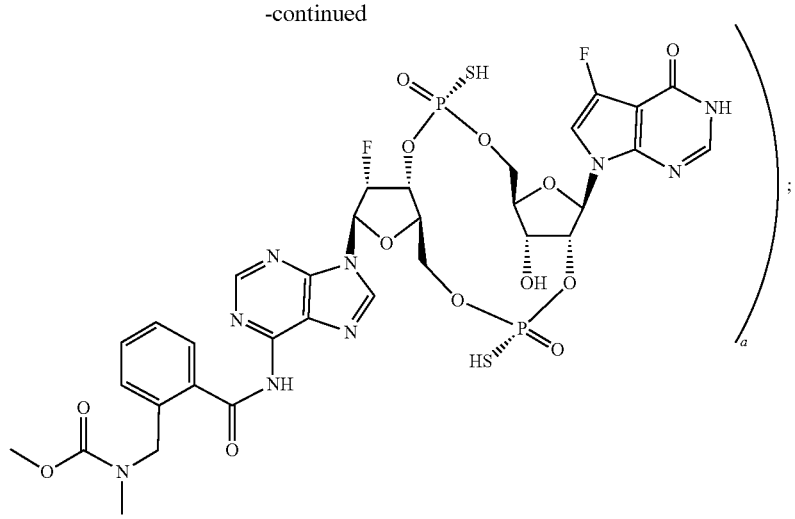

wherein a is an integer from 1 to 8.

8. A compound of claim 7, or a pharmaceutically acceptable salt thereof, wherein the antibody is monoclonal antibody 1D9 or an antibody which can compete with 1D9 for binding to human CCR2 or a portion of CCR2.

9. A compound of claim 7, or a pharmaceutically acceptable salt thereof, wherein the anti-CCR2 antibody or anti-CCR2 antigen-binding fragment comprises a light chain CDR1 comprising amino acids 24-39 of SEQ ID NO: 1; a light chain CDR2 comprising amino acids 55-61 of SEQ ID NO: 1; a light chain CDR3 comprising amino acids 94-102 of SEQ ID NO: 1; a heavy chain CDR1 comprising amino acids 31-35 of SEQ ID NO:2; a heavy chain CDR2 comprising amino acids 50-68 of SEQ ID NO:2; and a heavy chain CDR3 comprising amino acids 101-106 of SEQ ID NO:2.

10. A compound of claim 7, or a pharmaceutically acceptable salt thereof, wherein the anti-CCR2 antibody, or anti-CCR2 antigen-binding fragment comprises a heavy chain variable region comprising the amino acid sequence of SEQ ID NO: 2 and a light chain variable region, wherein the light chain variable region comprises the amino acid sequence of SEQ ID NO: 1.

11. A compound of claim 9, or a pharmaceutically acceptable salt thereof, wherein the anti-CCR2 antibody or anti-CCR2 antigen-binding fragment further comprises a heavy chain constant region selected from human immunoglobulins $IgG_1$, $IgG_2$, $IgG_3$, $IgG_4$, $IgA_1$, and $IgA_2$ heavy chain constant regions and a light chain constant region selected from the group consisting of human immunoglobulins IgGκ and IgGλ light chain constant regions.

12. A compound of claim 10, or a pharmaceutically acceptable salt thereof, wherein the anti-CCR2 antibody or anti-CCR2 antigen-binding fragment further comprises a heavy chain constant region selected from human immunoglobulins $IgG_1$, $IgG_2$, $IgG_3$, $IgG_4$, $IgA_1$, and $IgA_2$ heavy chain constant regions and a light chain constant region selected from the group consisting of human immunoglobulins IgGκ and IgGλ light chain constant regions.

13. A compound of claim 7, or a pharmaceutically acceptable salt thereof, wherein the anti-CCR2 antibody comprises a heavy chain region of SEQ ID NO: 3 and a light chain region of SEQ ID NO: 4.

14. A pharmaceutical composition comprising a compound of claim 1, or a pharmaceutically acceptable salt thereof, and one or more pharmaceutically acceptable carriers.

* * * * *

SEQUENCE LISTING

<160> NUMBER OF SEQ ID NOS: 6

<210> SEQ ID NO 1
<211> LENGTH: 112
<212> TYPE: PRT
<213> ORGANISM: Artificial Sequence
<220> FEATURE:
<223> OTHER INFORMATION: Kappa Light Chain Variable Region VL of
      humanided antibody 1D9

<400> SEQUENCE: 1

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Phe Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Arg Leu Glu Ile Lys
            100                 105                 110

<210> SEQ ID NO 2
<211> LENGTH: 117
<212> TYPE: PRT
<213> ORGANISM: Artificial Sequence
<220> FEATURE:
<223> OTHER INFORMATION: Kappa Heavy Chain Variable Region VH of
      humanided antibody 1D9

<400> SEQUENCE: 2

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Asn Trp Val Arg Gln Ala Pro Gly Lys Gly Leu Glu Trp Val
        35                  40                  45

Gly Arg Ile Arg Thr Lys Asn Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Phe Tyr Gly Asn Gly Val Trp Gly Gln Gly Thr Leu
            100                 105                 110

Val Thr Val Ser Ser
        115

<210> SEQ ID NO 3
<211> LENGTH: 447
<212> TYPE: PRT
<213> ORGANISM: Artificial Sequence
<220> FEATURE:
<223> OTHER INFORMATION: Sequence of humanized 1D9 Heavy Chain

<400> SEQUENCE: 3

-continued

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Asn Trp Val Arg Gln Ala Pro Gly Lys Gly Leu Glu Trp Val
        35                  40                  45

Gly Arg Ile Arg Thr Lys Asn Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Phe Tyr Gly Asn Gly Val Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
```

-continued

```
                420             425             430
His Asn His Tyr Thr Gln Lys Ser Leu Ser Leu Ser Pro Gly Lys
        435                 440                 445

<210> SEQ ID NO 4
<211> LENGTH: 219
<212> TYPE: PRT
<213> ORGANISM: Artificial Sequence
<220> FEATURE:
<223> OTHER INFORMATION: Sequence of humanized 1D9 Light Chain

<400> SEQUENCE: 4

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Phe Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 5
<211> LENGTH: 443
<212> TYPE: PRT
<213> ORGANISM: Artificial Sequence
<220> FEATURE:
<223> OTHER INFORMATION: Sequence of humanized 1D9 hIG4 isotype

<400> SEQUENCE: 5

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Asn Trp Val Arg Gln Ala Pro Gly Lys Gly Leu Glu Trp Val
        35                  40                  45

Gly Arg Ile Arg Thr Lys Asn Asn Asn Tyr Ala Thr Tyr Tyr Ala Asp
    50                  55                  60
```

-continued

Ser Val Lys Asp Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Phe Tyr Gly Asn Gly Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440

<210> SEQ ID NO 6
<211> LENGTH: 219
<212> TYPE: PRT
<213> ORGANISM: Artificial Sequence
<220> FEATURE:
<223> OTHER INFORMATION: Sequence of humanized 1D9 hIG4 isotype

<400> SEQUENCE: 6

```
Asp Val Val Met Thr Gln Ser Pro Leu Ser Leu Pro Val Thr Leu Gly
1               5                   10                  15
Gln Pro Ala Ser Ile Ser Cys Lys Ser Ser Gln Ser Leu Leu Asp Ser
            20                  25                  30
Asp Gly Lys Thr Phe Leu Asn Trp Phe Gln Gln Arg Pro Gly Gln Ser
        35                  40                  45
Pro Arg Arg Leu Ile Tyr Leu Val Ser Lys Leu Asp Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Trp Gln Gly
                85                  90                  95
Thr His Phe Pro Tyr Thr Phe Gly Gln Gly Thr Arg Leu Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215
```